(12) United States Patent
Odunsi et al.

(10) Patent No.: US 11,020,431 B2
(45) Date of Patent: Jun. 1, 2021

(54) COMPOSITIONS AND LIBRARIES COMPRISING RECOMBINANT T-CELL RECEPTORS AND METHODS OF USING RECOMBINANT T-CELL RECEPTORS

(71) Applicant: Health Research, Inc., Buffalo, NY (US)

(72) Inventors: Adekunle Odunsi, Williamsville, NY (US); Takemasa Tsuji, Williamsville, NY (US); Junko Matsuzaki, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 263 days.

(21) Appl. No.: 16/066,180

(22) PCT Filed: Jan. 6, 2017

(86) PCT No.: PCT/US2017/012464
§ 371 (c)(1),
(2) Date: Jun. 26, 2018

(87) PCT Pub. No.: WO2017/120428
PCT Pub. Date: Jul. 13, 2017

(65) Prior Publication Data
US 2019/0275081 A1    Sep. 12, 2019

Related U.S. Application Data

(60) Provisional application No. 62/275,600, filed on Jan. 6, 2016.

(51) Int. Cl.
| | | |
|---|---|---|
| *A61K 35/17* | (2015.01) | |
| *A61P 35/00* | (2006.01) | |
| *C07K 14/725* | (2006.01) | |
| *C12N 15/86* | (2006.01) | |
| *G01N 33/574* | (2006.01) | |
| *A61K 35/26* | (2015.01) | |
| *A61K 38/00* | (2006.01) | |

(52) U.S. Cl.
CPC .............. *A61K 35/17* (2013.01); *A61K 35/26* (2013.01); *A61P 35/00* (2018.01); *C07K 14/7051* (2013.01); *C12N 15/86* (2013.01); *G01N 33/57484* (2013.01); *A61K 38/00* (2013.01)

(58) Field of Classification Search
CPC ........ A61K 35/17; A61K 35/26; A61K 38/00; A61P 35/00; C07K 14/7051; C12N 15/86; G01N 33/57484
See application file for complete search history.

(56) References Cited

U.S. PATENT DOCUMENTS

| 2009/0053184 A1* | 2/2009 | Morgan | ............... C12N 5/0636 424/93.21 |
|---|---|---|---|
| 2011/0070208 A1 | 3/2011 | Bertoletti et al. | |
| 2013/0273647 A1 | 10/2013 | Sahin et al. | |

FOREIGN PATENT DOCUMENTS

| CN | 1306572 A | | 8/2001 |
|---|---|---|---|
| CN | 1639323 A | | 7/2005 |
| CN | 101287831 A | | 10/2008 |
| CN | 101415827 A | | 4/2009 |
| JP | 2008/263950 A | | 11/2008 |
| WO | 2014/160030 | * | 10/2014 |
| WO | WO 2014160030 A2 | | 10/2014 |
| WO | 2017/120428 A2 | | 7/2017 |

OTHER PUBLICATIONS

Han A, Glanville J, Hansmann L, Davis MM. Linking T-cell receptor sequence to functional phenotype at the single-cell level. Nat Biotechnol. Jul. 2014;32(7):684-92. Epub Jun. 22, 2014. Erratum in: Nat Biotechnol. Feb. 2015;33(2):210. (Year: 2014).*

Zhao, Y., et al., Primary Human Lymphocytes Transduced with NY-ESO-1 Antigen-Specific TCR Genes Recognize and Kill Diverse Human Tumor Cell Lines, The Journal of Immunology, Apr. 1, 2005, vol. 174, No. 7, pp. 4415-4423.

Lefranc, M., et al., The T Cell Receptor, Factbooks, Academic Press. 2001, pp. 76-77, 136, 181-182, 188, 277, 312, 377.

Baldueva, I.A., et al., Successes and perspectives of cellular immunotherapy for metastatic melanoma, Malignant Tumors, 2015, No. 4, special issue 2, pp. 16-19.

(Continued)

*Primary Examiner* — Scott Long
*Assistant Examiner* — Anjeanette Roberts
(74) *Attorney, Agent, or Firm* — Hodgson Russ LLP

(57) ABSTRACT

Provided are recombinant polynucleotides, including expression vectors encoding an alpha chain and/or a beta chain of a TCR having amino acid sequences from any of novel the AL, KQ, PP, 19305CD8, BB, KB, ST, JD, 19305DP, PB-P, PB-T, and PB 13.2 T Cell Receptors (TCRs) that are embodiments of the invention. Cells comprising the polynucleotides are provided, as are libraries of the recombinant polynucleotides and expression vectors. Methods are provided and involve administering to an individual modified human T cells that express a novel recombinant TCR. The methods are for prophylaxis and/or therapy of an individual diagnosed with, suspected of having or at risk for developing or recurrence of a cancer, wherein the cancer includes cancer cells which express NY-ESO-1 and/or its highly homologous LAGE-1 antigen.

19 Claims, 13 Drawing Sheets

Specification includes a Sequence Listing.

(56) References Cited

OTHER PUBLICATIONS

Database, UniProtKB, A0A0B4J275 (TVA17_HUMAN), T cell receptor alpha variable 17, Apr. 3, 2015, 3 pages. www.uniprot.org/uniprot/A0A0B4J275.

Yarilin, A. A., Basics of Immunology, Moscow: "Meditsina" Publishing House, 1999, pp. 184-185.

Stepanov, V. M., Molecular Biology: Structure and Function of Proteins, Moscow: Nauka Publishing House, 2005, pp. 61-62.

Patel, K. et al., Combination immunotherapy with NY-ESO-1-specific CAR+ T cells with T cell vaccine improves anti-myeloma effect, Blood, 2016, vol. 128, No. 22, p. 3366.

Chervin, A.S. et al., Design of T-cell receptor libraries with diverse binding properties to examine adoptive T-cell responses, Gene Therapy, Oct. 11, 2012, pp. 634-644, vol. 20 No. 6.

Robbins, P. F. et al., A pilot trial using lymphocytes genetically engineered with an NY-ESO-1-reactive T-cell receptor: Long-term follow up and correlates with response, Clinical Cancer Research, Mar. 1, 2015, pp. 1019-1027, vol. 21, No. 5.

Rapoport, A. P. et al., NY-ESO-1 specific TCR-engineered T-cells mediate sustained antigen-specific antitumor effects in myeloma, Nature Medicine, Jul. 20, 2015, vol. 21(8), pp. 914-921.

\* cited by examiner

Plasmids used to create TCR-expressing backbone vectors

(A) Classical retroviral vectors

(B) A recent retroviral vector

Cloning of 5'-LTR to Splice Acceptor fragment into pMIG vectors

(A) Attachment of restriction enzyme sites by PCR (B) Cloning of the PCR fragment into pMIG vectors

Introduction of a stuffer fragment and the PacI restriction enzyme site

(A) Attachment of restriction enzyme sites by PCR (B) Cloning of the stuffer fragment

Cloning of TCR expressing cassettes into vectors

(A) Attachment of restriction enzyme sites by PCR

(B) Cloning of the TCR expressing cassette

(A) Retroviral vector (B) TCR expression cassette

A

B

COMPOSITIONS AND LIBRARIES COMPRISING RECOMBINANT T-CELL RECEPTORS AND METHODS OF USING RECOMBINANT T-CELL RECEPTORS

CROSS REFERENCE TO RELATED APPLICATIONS

This application claims priority to U.S. provisional patent application no. 62/275,600, filed Jan. 6, 2016, the disclosure of which is incorporated herein by reference.

FIELD

The present disclosure relates generally to immunotherapy and more specifically to recombinant T cell receptors that can impart direct tumor recognition capability to T cells.

BACKGROUND

Tumor antigen-specific T cells recognize and kill cancer cells by using unique T cell receptor (TCR) alpha and beta chain complex which is specific against tumor antigen peptide/HLA complex. Extremely diverse TCR alpha/beta sequence alone determines peptide-specificity, HLA restriction, and strength of recognition. Gene-engineering of polyclonally expanded peripheral T cells with tumor antigen-specific TCR generates large numbers of tumor antigen-specific T cells that can be used in adoptive T cell therapy of cancer patients using autologous gene-engineered T cells. Currently, only a few therapeutic TCR gene products has been tested in clinical trials, which significantly restricts applicability of this powerful therapeutic strategy to limited patients by their HLA types as well as antigen expression in cancer cells. There is thus an ongoing and unmet need for improved compositions and methods for use in adoptive immune therapy involving recombinant TCRs. The present disclosure meets this need.

BRIEF SUMMARY

The present disclosure provides in one aspect a modified human T cell comprising a recombinant polynucleotide encoding an alpha chain and/or a beta chain of a TCR, wherein the TCR is one of the TCRs referred to herein as AL, KQ, PP, 19305CD8, BB, KB, ST, JD, 19305DP, PB-P, PB-T, or PB13.2, as described further below. In another aspect the disclosure comprises a method for prophylaxis and/or therapy of an individual diagnosed with, suspected of having or at risk for developing or recurrence of a cancer, wherein the cancer comprises cancer cells which express NY-ESO-1 and/or its highly homologous LAGE-1 antigen, the method comprising administering to the individual modified human T cells that express a recombinant TCR of this disclosure.

In another aspect the disclosure comprises an expression vector encoding a TCR, wherein the TCR comprises an alpha chain and/or a beta chain having the sequence of 19305DP AL, KQ, PP, 19305CD8, BB, KB, ST, JD, PB-P, PB-T, or PB13.2 as further described below.

In another aspect the disclosure provides a library comprising a plurality of expression vectors, wherein the expression vectors encode at least one alpha chain or a beta chain or a combination thereof selected from the group of TCR alpha and beta chains described herein for TCRs 19305DP, AL, KQ, PP, 19305CD8, BB, KB, ST, JD, PB-P, PB-T, or PB13.2 as further described below. In one example, the library can further comprise at least one expression vector encoding the alpha chain, the beta chain, or a combination thereof for the JM, 5B8, SB95 TCRs which are also further described below.

In another aspect the disclosure provides a method comprising selecting an expression vector from a library of this disclosure, wherein the selection is based at least in part on the HLA type of an individual diagnosed with or suspecting of having a NY-ESO-1/LAGE-1 positive cancer, and distributing the selected expression vector to a party for use in introducing the expression vector into immune cells of the diagnosed individual.

In another aspect the disclosure provides a method comprising selecting an expression vector from an expression vector library of this disclosure, and introducing the expression vector into immune cells obtained from an individual diagnosed with a NY-ESO-1/LAGE-1 positive cancer, wherein the HLA type of the TCR encoded by the expression vector is matched to the HLA type of the individual, the method optionally comprising introducing the immune cells comprising the expression vector into an individual in need thereof.

In another aspect the disclosure provides a method comprising testing a sample from an individual to determine whether or not the individual has a NY-ESO-1/LAGE-1 positive cancer, and subsequent to a determination that the individual has the NY-ESO-1/LAGE-1 positive cancer, selecting an expression vector from a library of this disclosure based at least in part on the HLA type of the individual, and introducing the expression vector into immune cells of the individual, the method optionally further comprising introducing the immune cells comprising the expression vector into the individual.

In another aspect the disclosure provides computer-based methods for selecting and/or retrieving a TCR from a library of this disclosure for use in an immunotherapy. In embodiments the disclosure includes a database comprising nucleotide and/or amino acid sequences of the TCRs, or other indicia of the TCRs. In certain embodiments the disclosure includes a system that comprises a processor programmed to match a TCR of a library of this disclosure with the HLA type of a sample.

BRIEF DESCRIPTION OF THE FIGURES

FIG. 1A. For transduction of T cells, murine stem cell virus (MSCV)-derived vectors have been widely used because of strong promoter activity by MSCV long terminal repeats (LTR) and in vivo stability of transgene expression in hematopoietic cells. As 3'-LTR is copied to 5'-LTR during integration to host cells (T cells) and responsible for the transcription of transgenes, 3'-LTR in the plasmids is important in the expression. On the other hand, 5'-LTR is responsible for transcription for virus production. A Schematic representation for classical MSCV-derived vectors (pMIG-II and pMIG-w) is shown in FIG. 1A. Both vectors have MSCV-derived LTR at 5' and 3' sites, packaging signal (w), multiple cloning sites (MCS). A transgene is cloned in the multiple cloning site (MCS), which is followed by the internal ribosomal entry site (IRES) and the green fluorescent protein gene (GFP) to efficiently detect transduced cells. pMIG-w vector has additional woodchuck hepatitis virus post-transcriptional regulatory element (WRE), which enhances expression of the transgene.

Further modifications can be introduced, such as those found in the commercial retroviral vector, pDON-5 (Clontech). pDON-5, which is derived from a murine leukemia virus (MLV) vector, and replaces the 5'-LTR with the CMV/MLV hybrid LTR for enhanced virus production through strong CMV promoter activity in virus packaging cell lines. Additionally, a partial intron from the human elongation factor 1a gene can be introduced to provide a splice acceptor site (SA), which together with an endogenous splice donor site (SD) induces splicing and enhances transcription.

Figure 1A:
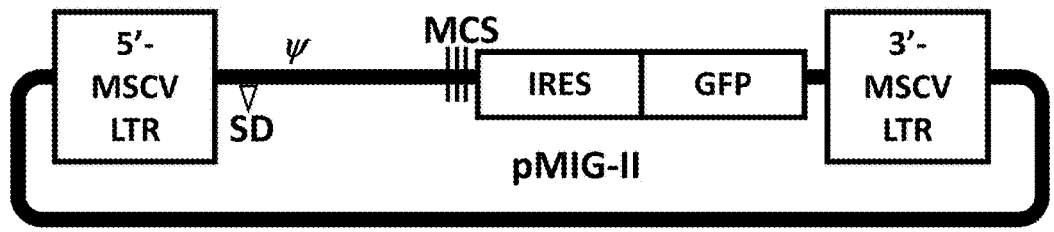
FIGS. 1A-1D provide graphical depictions of vectors of this disclosure.
Figure 1A:
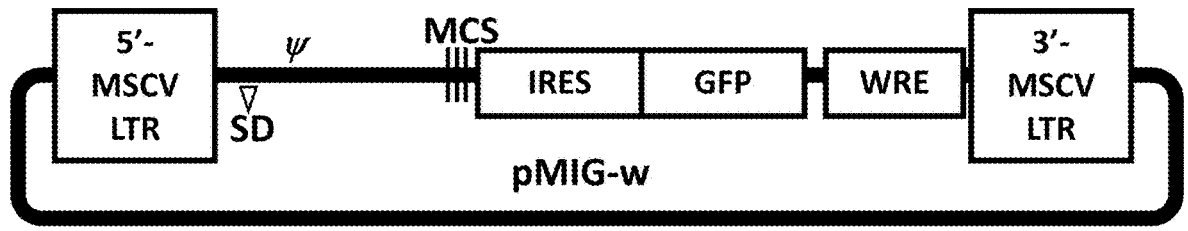
Figure 1A:
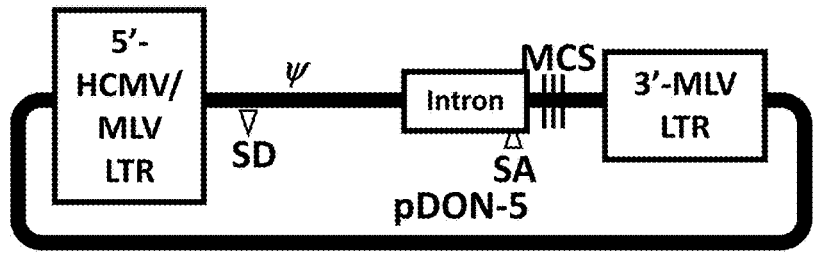
Figure 1B:
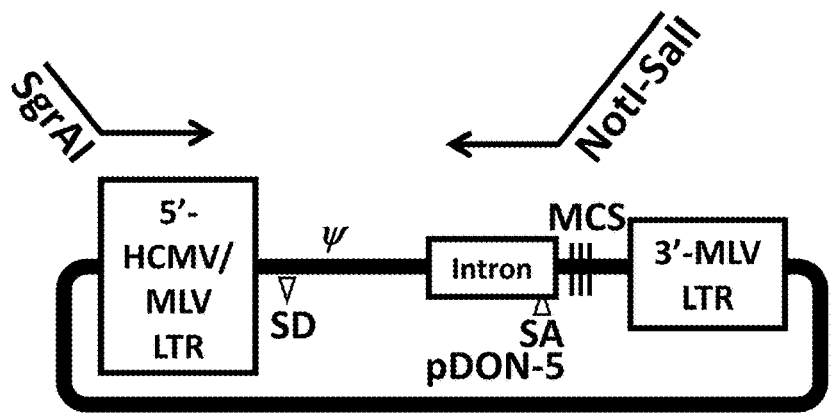
Figure 1B:
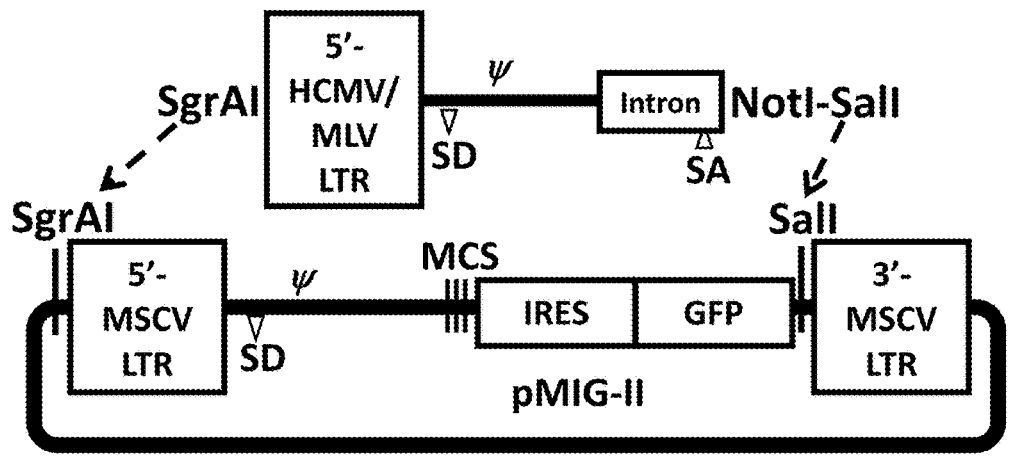
Figure 1B:
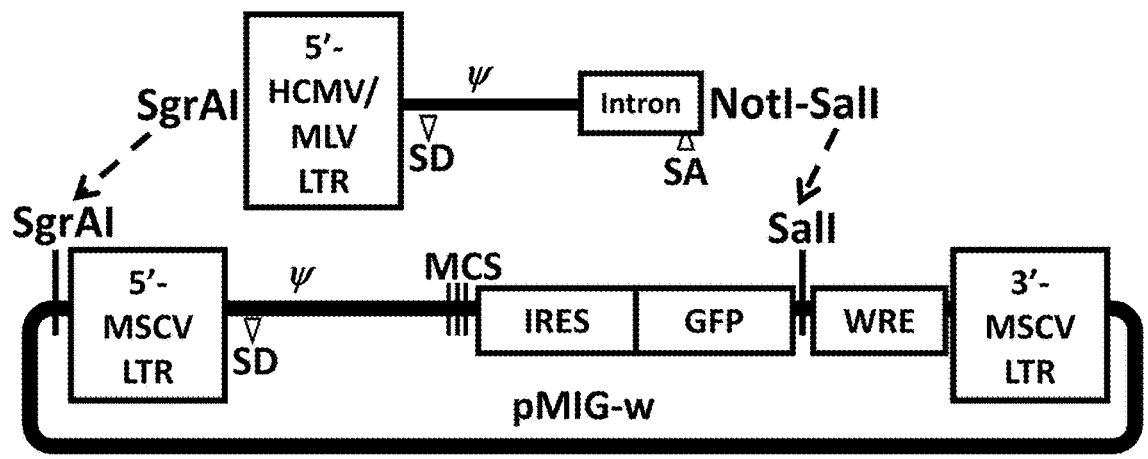

FIG. 1B. To create a retrovirus vector which can produce high-titer retrovirus that induces high level transgene (TCR) expression in T cells, we amplified a DNA fragment from 5'-LTR to the intron containing a splice acceptor site in the pDON-5 plasmid.

The forward primer was designed to append SgrAI restriction enzyme recognition site before 5'-LTR and the reverse primer was designed to append NotI and SalI sites after the intron. PCR-amplified fragment was treated with SgrAI and SalI and inserted into pMIG-II and pMIG-w plasmids so that 5'-LTR to GFP is replaced.

Figure 1C:
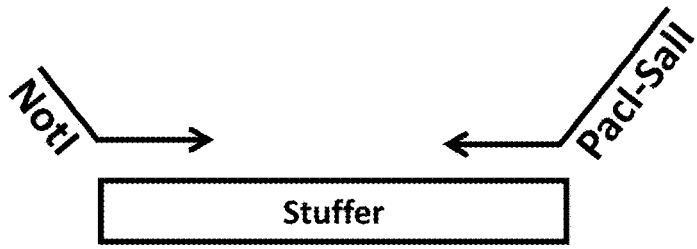
Figure 1C:
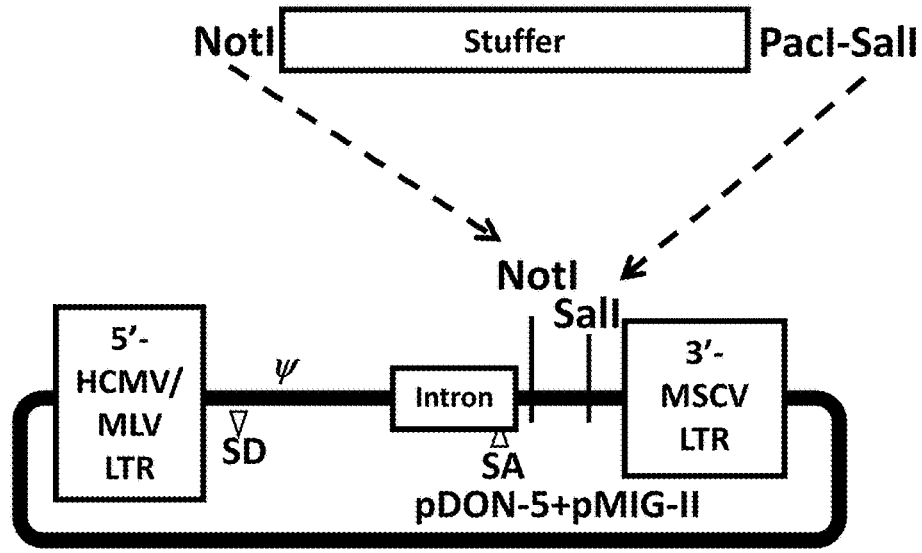
Figure 1C:
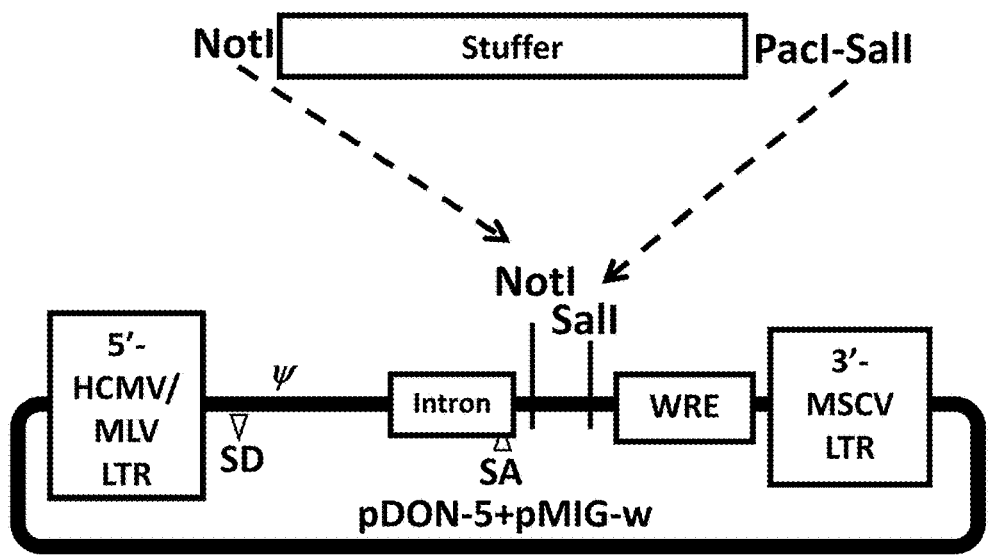

FIG. 1C. The depicted plasmids only have NotI and SalI recognition sites for cloning. The use of SalI a known 6-mer sequence is not preferred as this short recognition sequence may appear in the transgene. To provide additional restriction enzyme recognition site which is believed to be absent from most transgenes that are pertinent to this disclosure, we amplified a 1.8 kb DNA fragment (stuffer) with a forward primer with a NotI restriction site, and a reverse primer with PacI-SalI sites. The amplified fragment was treated with NotI and SalI restriction enzymes and inserted into new plasmids.

Figure 1D:
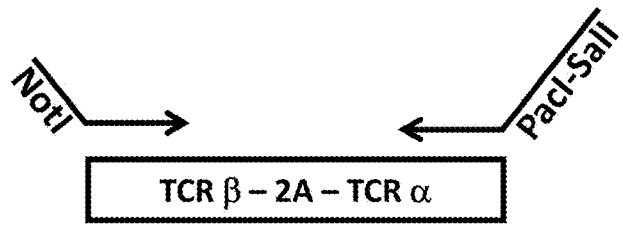
Figure 1D:
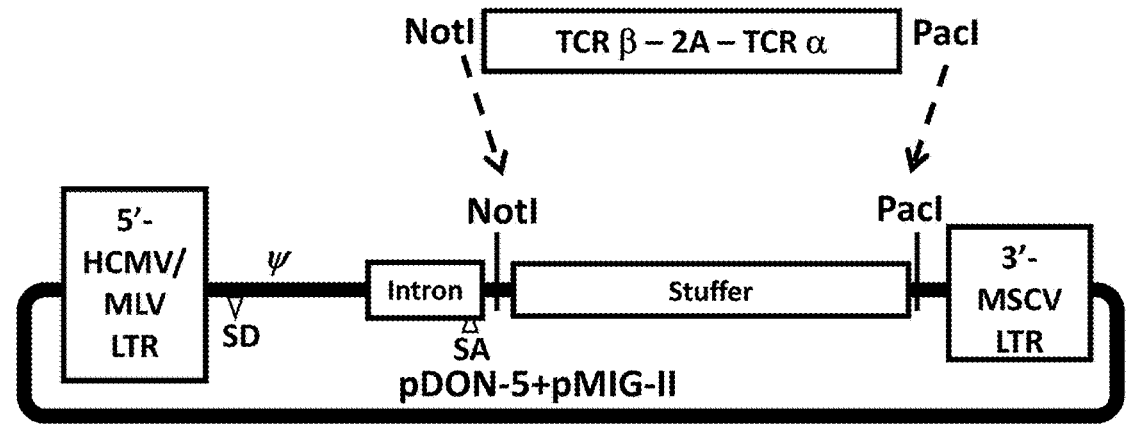
Figure 1D:
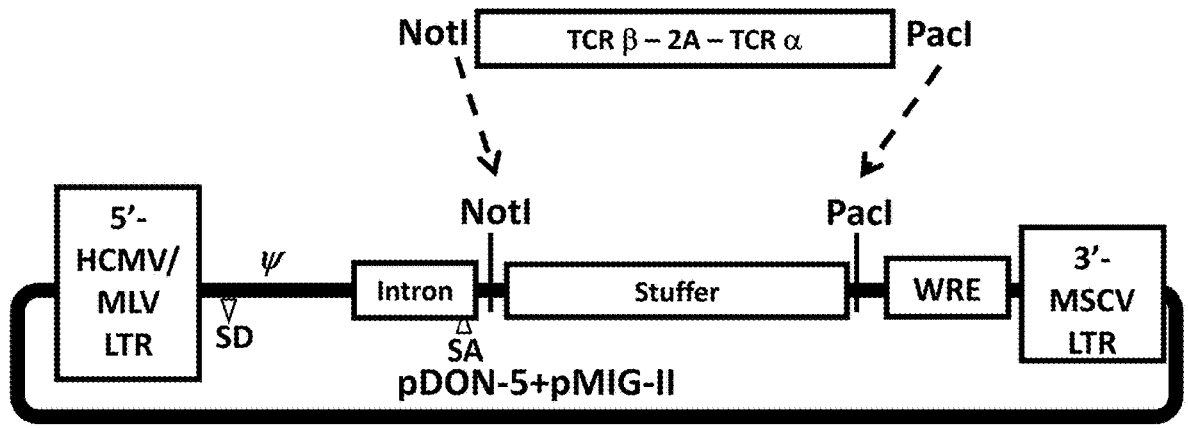

FIG. 1D. The TCR expression cassette was amplified with the forward primer with the NotI restriction site and the reverse primer with the PacI restriction enzyme site. The amplified expression cassette was treated with NotI and PacI restriction enzymes and inserted into the new plasmids.

Figure 2:
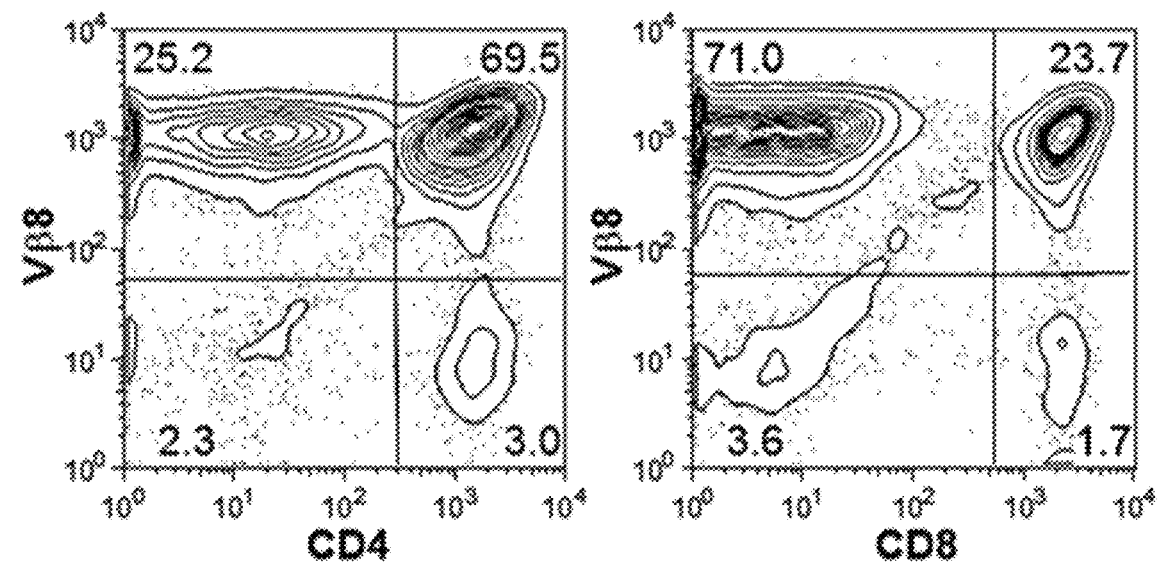
Figure 2:
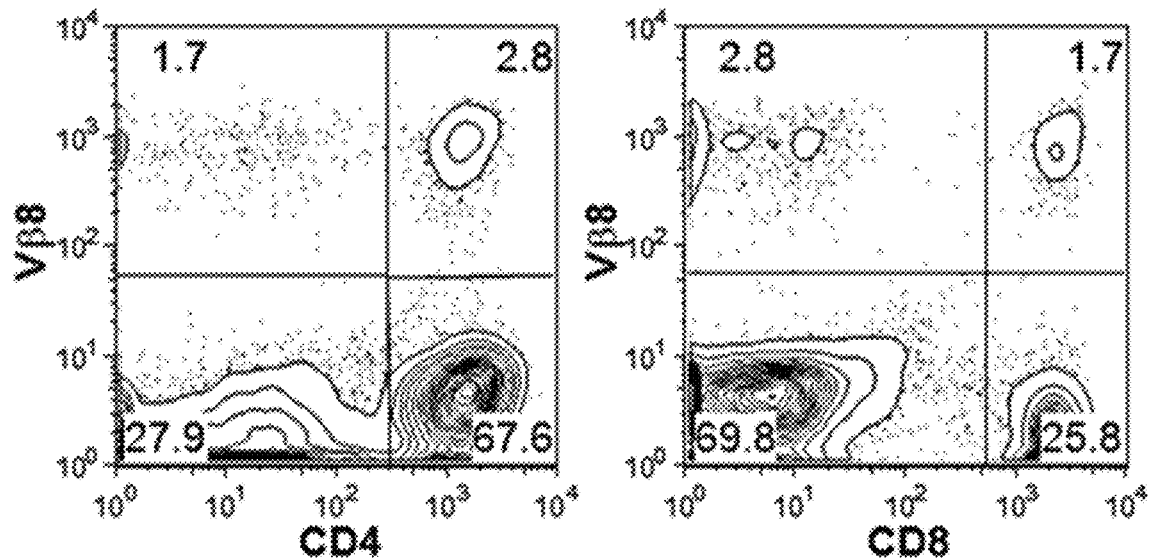

FIG. 2. Expression of 19305DP-TCR on polyclonally activated T cells. Polyclonally activated T cells from peripheral blood mononuclear cells were transduced twice with retroviral vector encoding 19305DP-TCR, whose beta chain variable region was a
Vb8 subtype. Expression was measured by staining with anti-TCR Vb8 antibody together with anti-CD4 and anti-CD8 antibodies.

Figure 3:
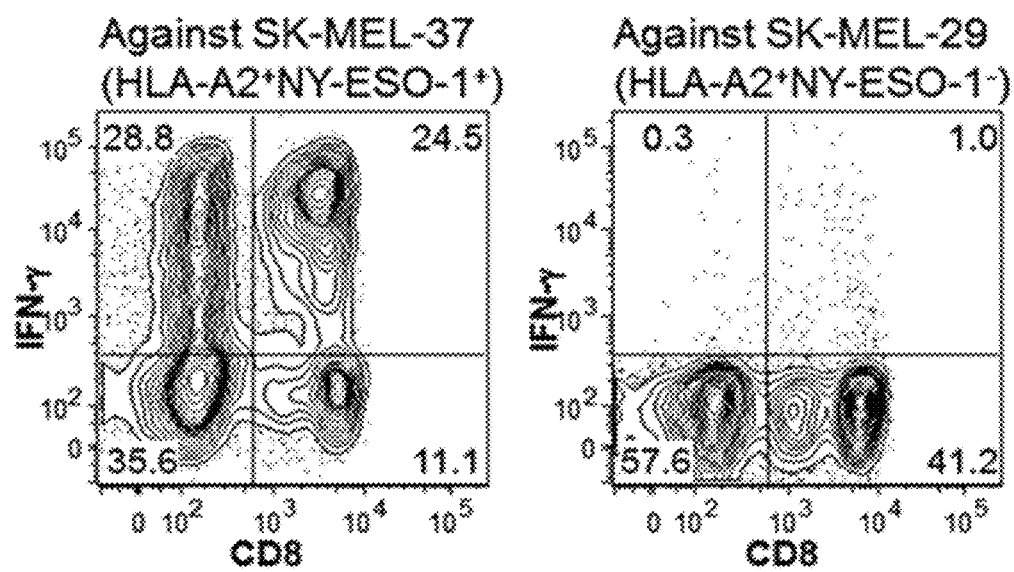
Figure 3:
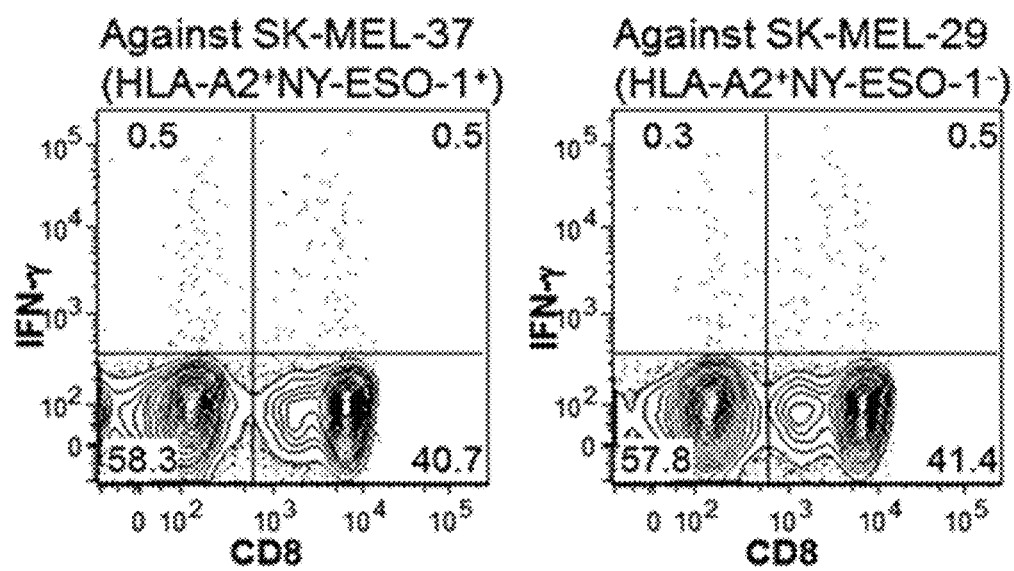

FIG. 3. Cancer cell recognition by 19305DP-TCR-transduced T cells. 19305DP-TCR transduced T cells were co-cultured with NY-ESO-1+SK-MEL-37 and NY-ESO1-SK−MEL-29 melanoma cells lines for 6 hours in the presence of Golgi Stop and IFN-g production was measured by intracellular IFN-g staining in combination with cell surface CD8 staining.

Figure 4:
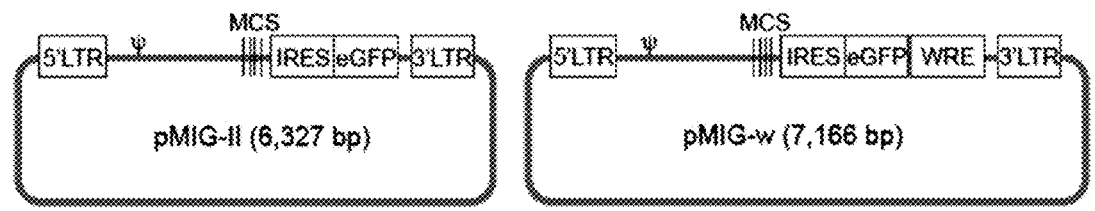
Figure 4:
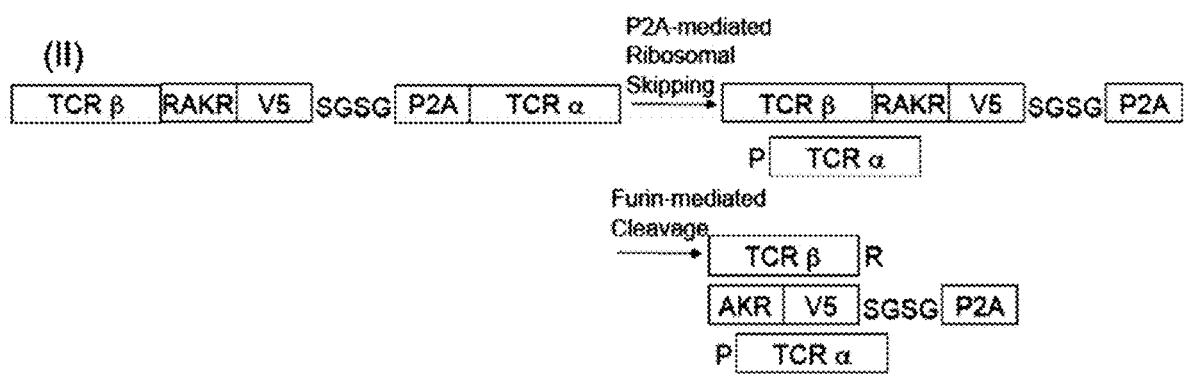

FIG. 4, panel A. Retrovirus vector used to express TCRs. LTR: long-terminal repeat; ψ: packaging signal; MCS: multiple cloning site; IRES: internal ribosome entry site; eGFP: enhanced green fluorescent protein. FIG. 4 panel B. TCR expressing cassette. (I) TCR β and α chain-coding cDNA sequences are connected by a GSG (Gly-Ser-Gly) linker and a P2A ribosomal skipping sequence. (II) TCR β and α chain-coding cDNA sequences are connected by a furin protease recognition site (RAKR (Arg-Ala-Lys-Arg) ((SEQ ID NO:59)), a SGSG (Ser-Gly-Ser-Gly) (SEQ ID NO:60) linker, V5 epitope, and a P2A ribosomal skipping sequence.

Figure 5:
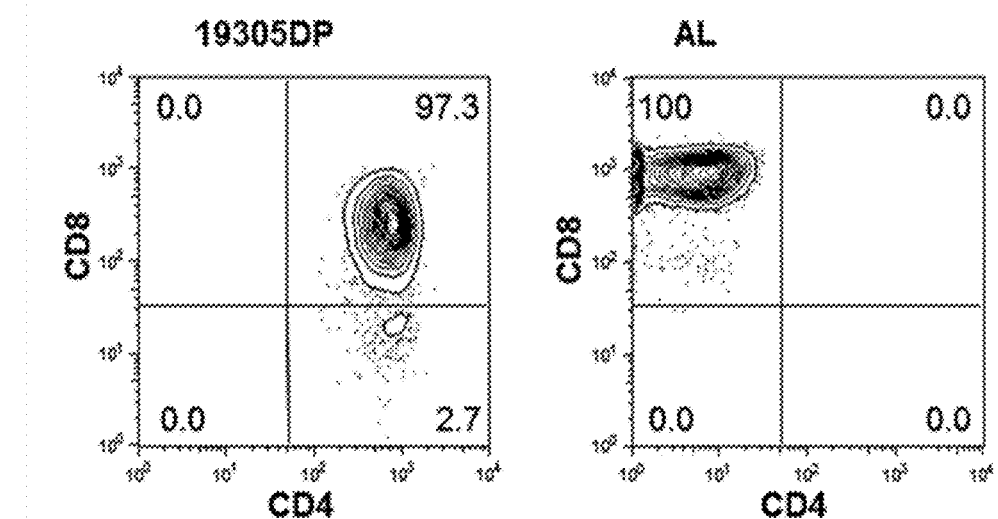

FIG. 5. Cell surface expression of CD4 and CD8 molecules on HLA-A*02-restricted T cell clones. 19305DP-TCR CD4/CD8 double positive T cell clone and AL CD8 single positive T cell clone were stained by anti-CD4 and anti-CD8 monoclonal antibodies and analyzed by flow cytometry.

Figure 6:
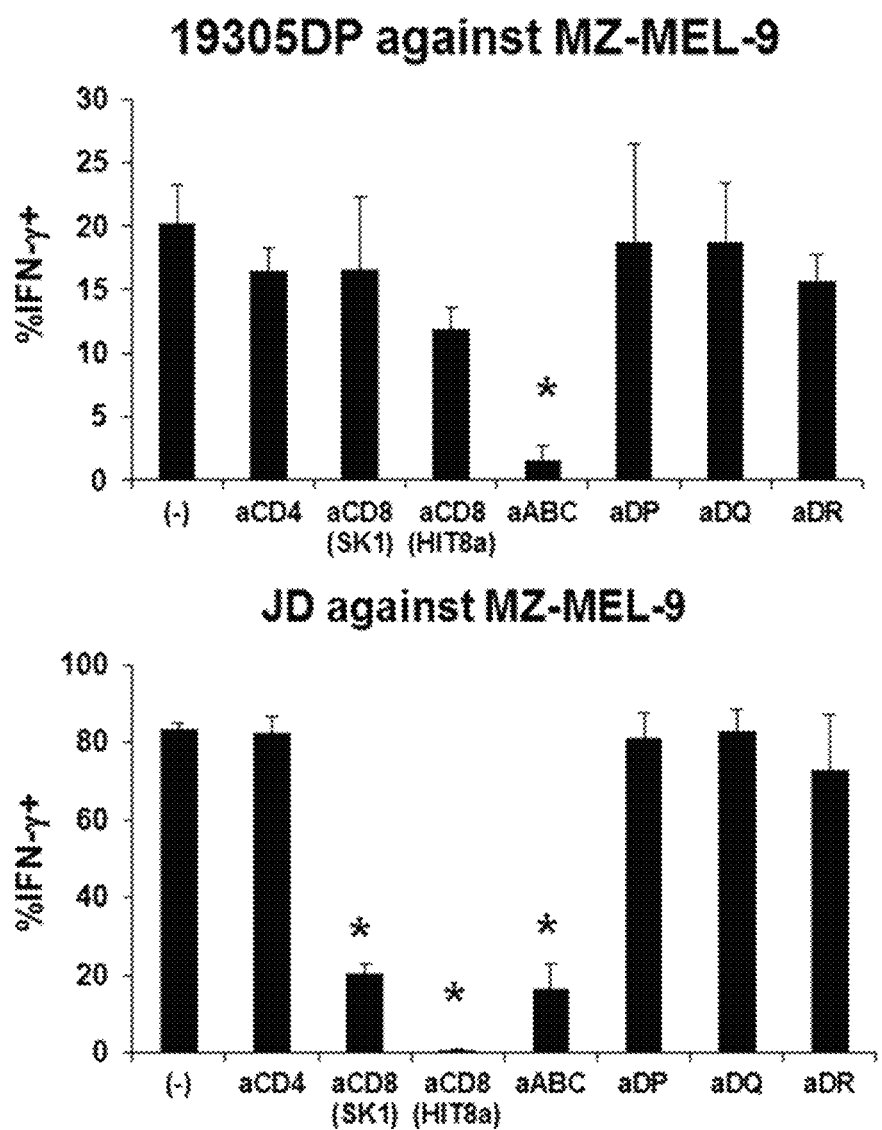

FIG. 6. Effect of blocking antibodies on recognition of cancer targets. 19305DP-TCR CD4/CD8 double positive T cell clone and JD CD8 single-positive T cell clone were co-cultured with HLA-A*02+NY-ESO-1+ melanoma cell line MZ-MEL-9 in the presence or absence of the indicated antibodies. Anti-HLA class I antibody (aABC) inhibited recognition by both 19305DP and JD. Although two anti-CD8 antibodies significantly inhibited recognition by JD, recognition by 19305DP was not inhibited, indicating CD8-independent recognition of cancer targets. * indicates significant ($p<0.05$) inhibition.

Figure 7:
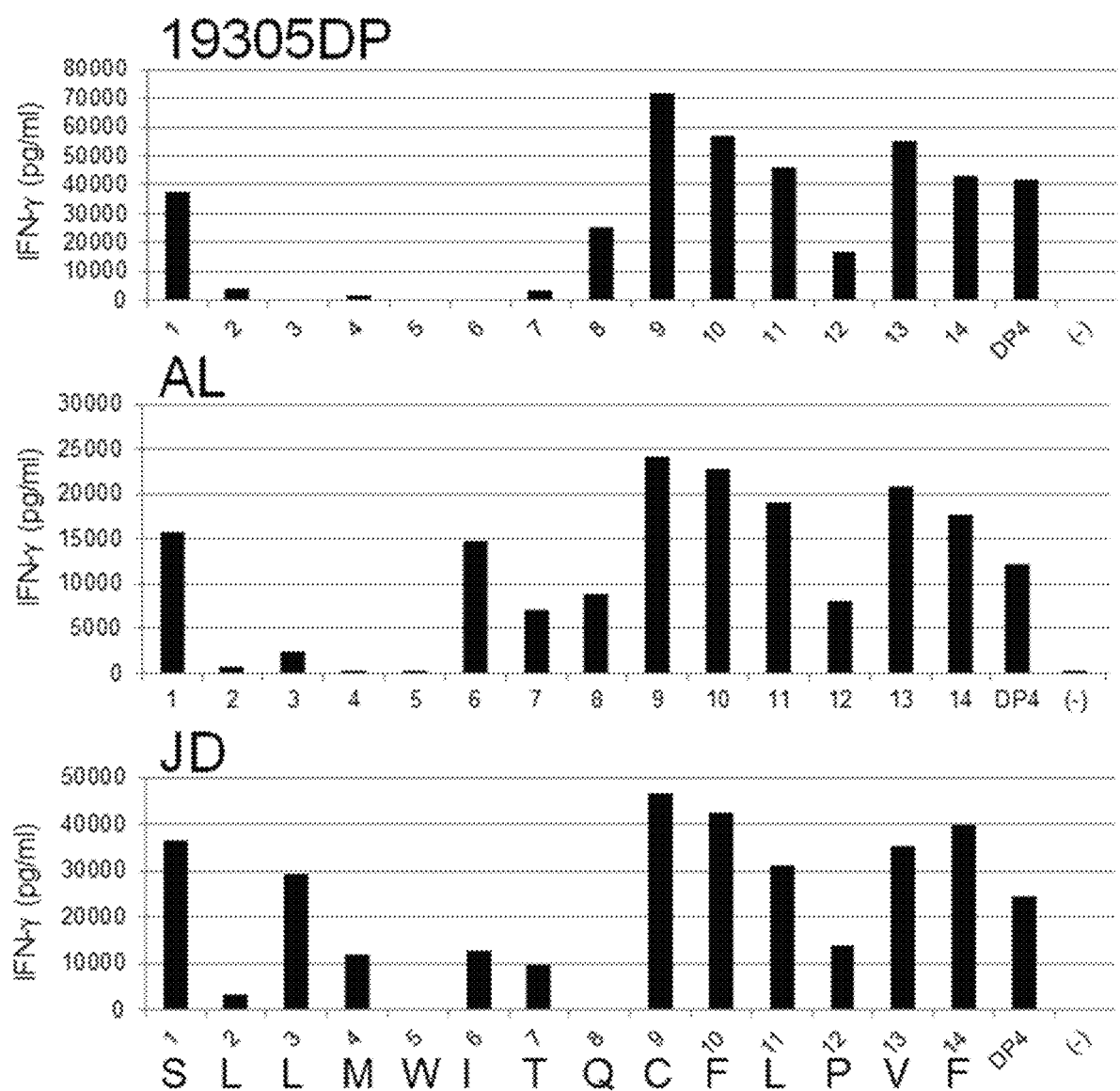

FIG. 7. Effect of alanine substitution on NY-ESO-1 peptide recognition. Each amino acid residue in NY-ESO-1 (157-170) peptide (DP4 peptide SLLMWITQCFLPVF (SEQ ID NO:61) was substituted with alanine residue. HLA-A*02-positive and NY-ESO-1-negative cancer cell was pulsed or un-pulsed (−) with alanine substituted (1-14) or natural DP4 peptide (DP4). Recognition by 19305DP CD4/CD8 double -positive T cell clone, AL CD8 single -positive T cell clone and JD CD8 single positive T cell clone was investigated by measuring IFN-g in the supernatant. Alanine substitution of amino acids at positions 2, 3, 4, 5, 6, and 7 (LLMWIT-SEQ ID NO: 62) significantly decreased the recognition by 19305DP, indicating that these residues are important for T cell recognition. In silico analysis showed that there is no known proteins with LLMWIT sequence, except for NY-ESO-1 and LAGE-1.

Figure 8:
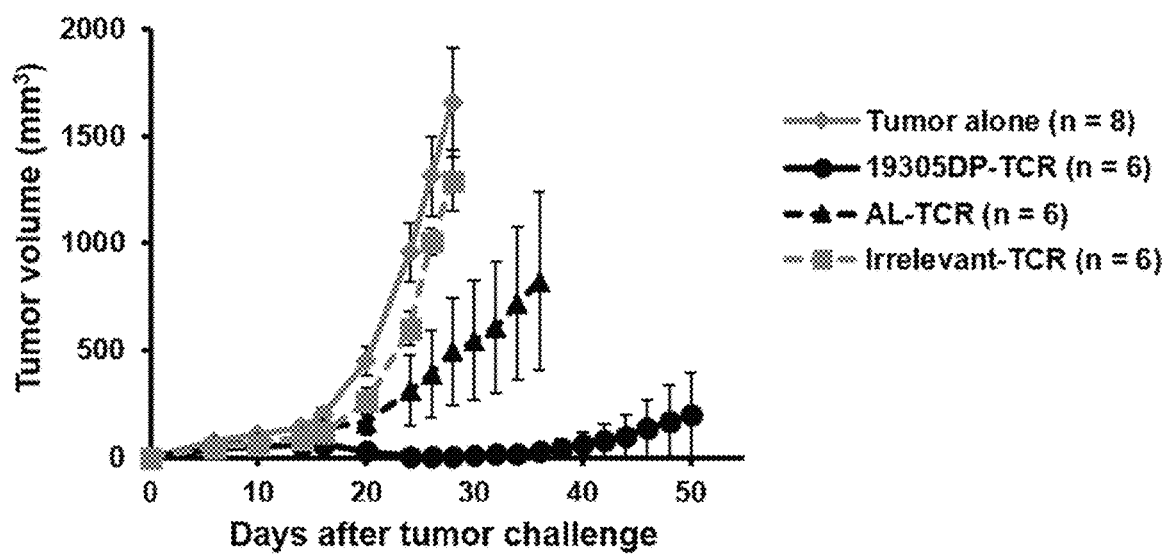
Figure 8:
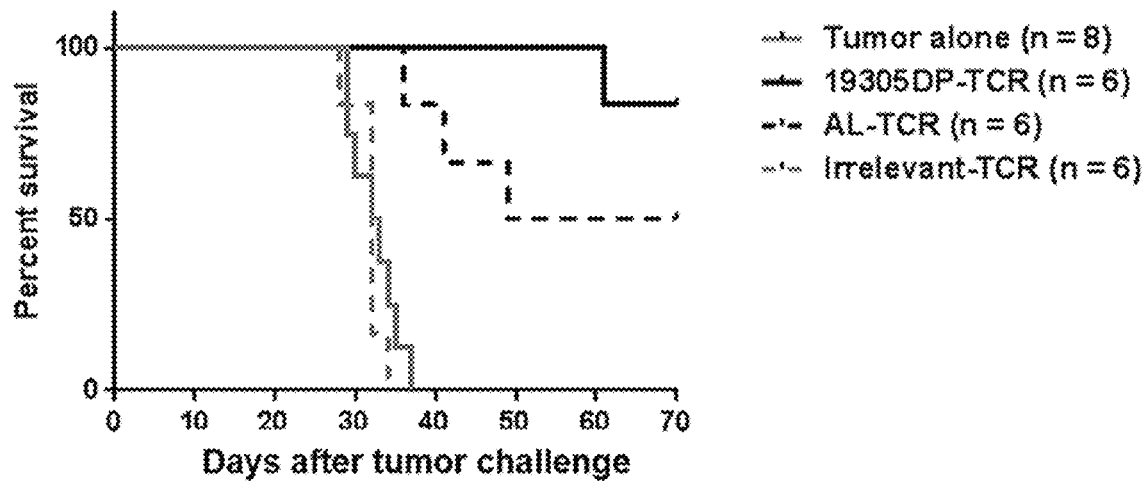

FIG. 8. In vivo anti-tumor activity of 19305DP-TCR-transduced T cells. NOD/Scid/IL-2Rg-chain-deficient (NSG) mice were subcutaneously injected with $1\times10^6$ HLA-A2+NY-ESO-1+ A375 cell line. Peripheral blood mononuclear cells (PBMCs) were polyclonally activated and transduced with 19305DP-TCR, AL-TCR or irrelevant-TCR by retroviral vectors. On day 11, $2.5\times10^5$ TCR transduced T cells were intravenously injected. Tumor volume was measured every other days after T-cell injection by digital caliper. 19305-TCR-transduced T cells significantly inhibited tumor growth (Panel A) and prolonged survival (Panel B). Five out of 6 mice treated with 19305DP-TCR-transduced T cells were tumor free at day 40, while 4 out of 6 mice injected with AL-TCR-transduced T cells had tumor at this time point.

Figure 9:
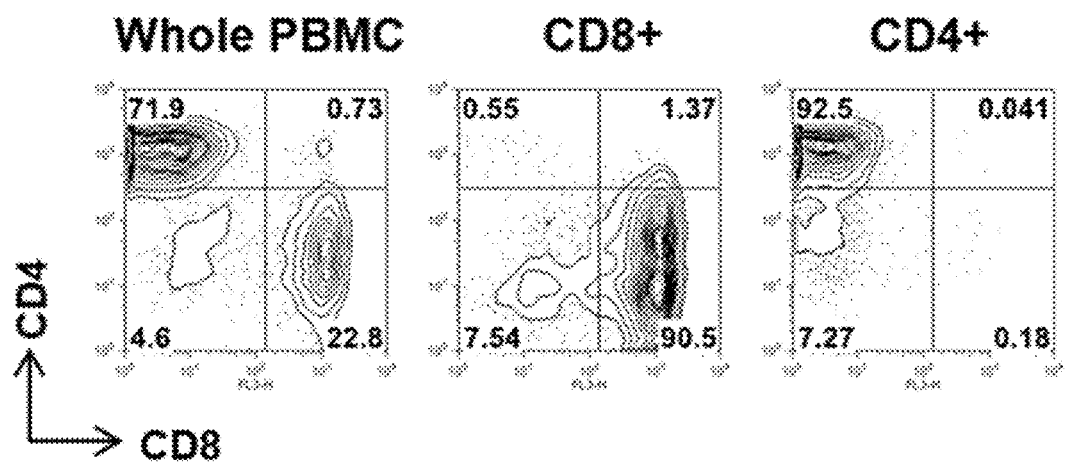
Figure 9:
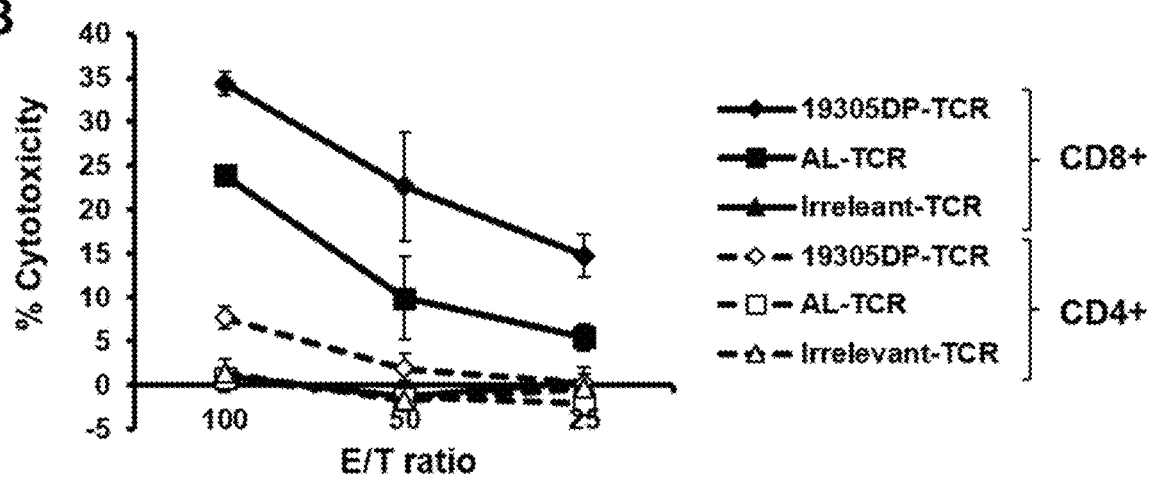
Figure 9:
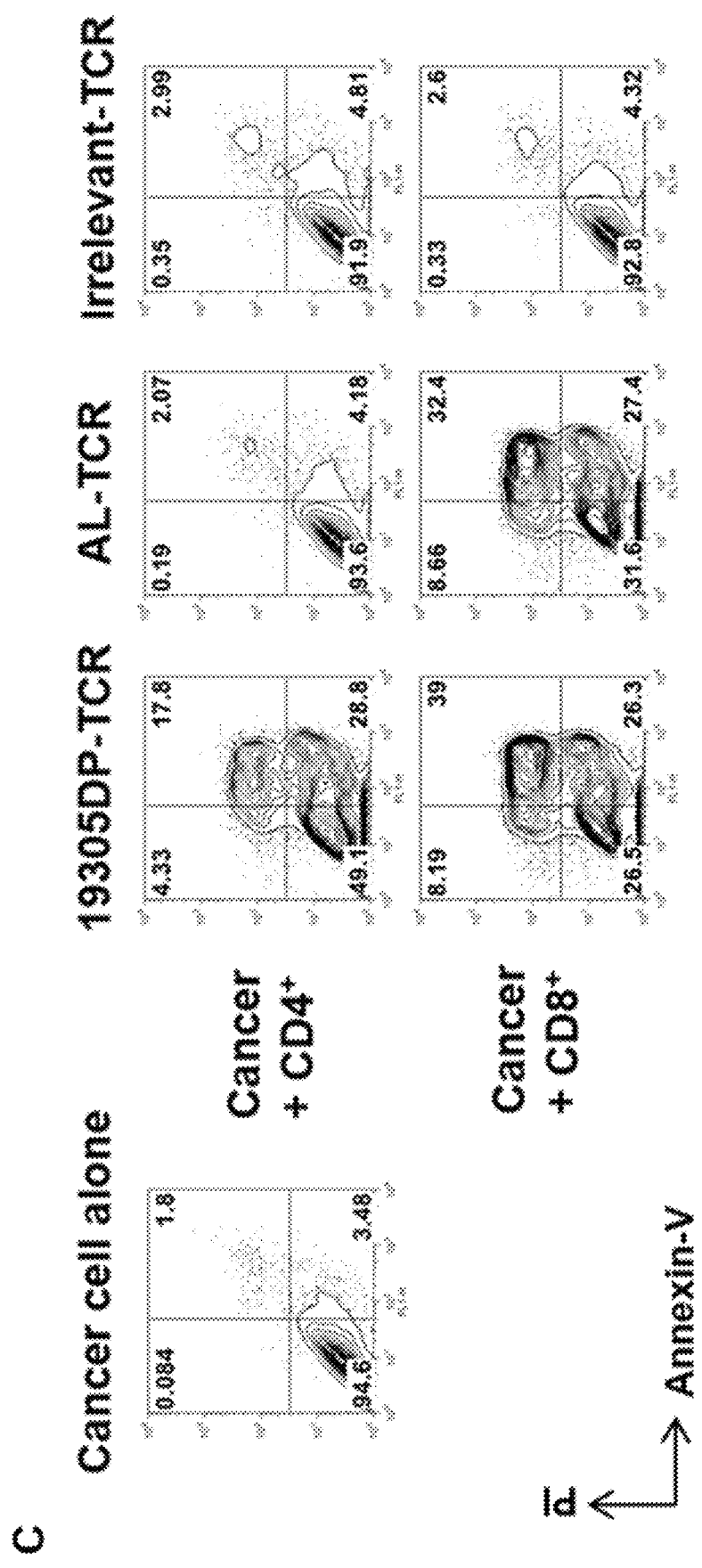

FIG. 9. In vitro CTL activity of CD8+ and CD4+ T cells transduced with 19305DP-TCR. CD4+ or CD8+ T cells were depleted from PBMC using biotin-conjugated anti-CD4 or anti-CD8 antibody followed by anti-biotin Dynabeads. CD4-depleted and CD8-depleted PBMC were polyclonally activated and transduced with 19305DP-TCR, AL-TCR or irrelevant-TCR by retrovial vectors. (Panel A) The purity of CD8− (CD4-depleted cells) and CD4+ (CD8-depleted cells) T cells transduced with TCR were determined by flow cytometry prior to in vivo experiment. (Panel B) Cytotoxic activity of CD8+ or CD4+ T cells transduced with indicated TCR against HLA-A2+NY-ESO-1+ Me1624.38 cell line was tested by Calcein-AM assay after 4 hours incubation. (Panel C) Cancer cell apoptotic cell death after cocultured with CD4− or CD8− T cells transduced with indicated TCR. HLA-A2+NY-ESO-1+ A375 cell line ($2.5\times10^5$) was cocultured with $5\times10^5$ T cells for 20 hours. Apoptotic cell death was determined by annexin-V and PI staining. Whereas 19305DP-TCR-transduced CD4− T cells showed week cytotoxic activity compared with CD8− T cells by short-term cytotoxic assay Panel B), the CD4+ T cells induced apoptotic cell death (Panel C). Cancer cell death was not observed when cocultured with AL-TCR-transduced CD4+ T cells.

Figure 10:
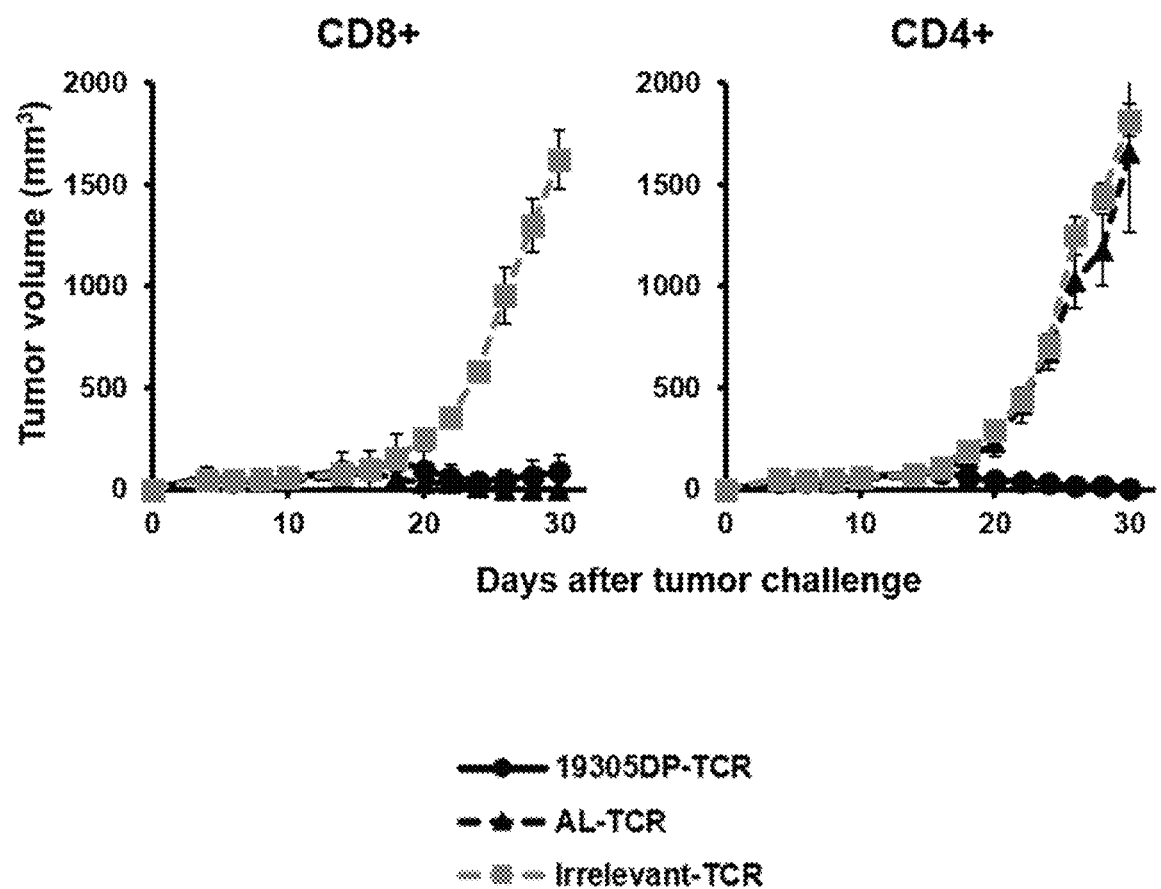

FIG. 10. Anti-tumor activity of CD8+ and CD4+ T cells transduced with 19305DP-TCR. CD4+ or CD8+ T cells were depleted from PBMC using biotin-conjugated anti-CD4 or anti-CD8 antibody followed by anti-biotin Dynabeads. CD4-depleted and CD8-depleted PBMC were polyclonally activated and transduced with 19305DP-TCR, AL-TCR or irrelevant-TCR by retroviral vectors. NOD/Scid/IL-2Rg-chain-deficient (NSG) mice were subcutaneously injected with 1×10$^6$ HLA-A2$^+$NY-ESO-1$^+$ A375 cell line. On day 11, 0.6×10$^5$ TCR transduced CD8$^+$ T cells (25% of whole PBMC) and 1.9×10$^5$ TCR transduced CD4$^+$ T cells (75% of whole PBMC) were intravenously injected. Tumor volume was measured every other days after T-cell injection by digital caliper. Both 19305DP-TCR and AL-TCR-transduced CD8$^+$ T cells controlled tumor growth (left), while only 19305DP-TCR transduced CD4$^+$ T cells showed tumor regression (right).

DETAILED DESCRIPTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

Each polynucleotide described herein includes its complementary sequence and its reverse complementary sequence, as well as RNA equivalents of DNA sequences wherein each T in a DNA sequence is replace with U. All polynucleotide sequences encoding the amino acid sequences described herein are included within the scope of this disclosure.

The present disclosure provides compositions and methods for prophylaxis and/or therapy of a variety of cancers. In general, the cancers are those which express the well-known NY-ESO-1/LAGE-1 antigen.

The disclosure includes each of the recombinant TCRs described herein, polynucleotides encoding them, expression vectors comprising the polynucleotides, cells into which the polynucleotides have been introduced, including but not necessarily limited CD4$^+$ T cells, CD8$^+$ T cells, natural killer T cells, γδ T cells, and progenitor cells, such as hematopoietic stem cells. As used in this disclosure, a "recombinant TCR" means a TCR that is expressed from a polynucleotide that was introduced into the cell, meaning prior to the initial introduction of the polynucleotide the TCR was not encoded by a chromosomal sequence or other polynucleotide in the cell.

In embodiments, the cells into which the polynucleotides are introduced are lymphoid progenitor cells, immature thymocytes (double-negative CD4-CD8-) cells, or double-positive thymocytes (CD4+CD8+). In embodiments, the progenitor cells comprise markers, such as CD34, CD117 (c-kit) and CD90 (Thy-1). The disclosure includes methods of making the TCRs, methods of modifying cells so that they express the TCRs, the modified cells, and methods of using the modified cells for anti-cancer approaches. Libraries of distinct TCRs are also included.

In particular embodiments, the disclosure includes a method for prophylaxis and/or therapy of an individual diagnosed with, suspected of having or at risk for developing or recurrence of a cancer, wherein the cancer comprises cancer cells which express NY-ESO-1/LAGE-1 antigen. This approach comprises in one aspect administering to the individual modified human cells comprising a recombinant polynucleotide encoding a TCR of this disclosure. The modified human cells, such as modified T cells, are enhanced relative to their unmodified T cell counterparts in their ability to fight cancer. Thus, in embodiments practicing a method of this disclosure results in a therapeutic response which can include but is not necessarily limited to slowing the growth rate of cancer cells and/or tumors, reducing tumor volume and/or reducing an increase in the rate of tumor volume increase, killing cancer cells, extending life span of an individual who has been diagnosed with a cancer as more fully described herein, and other parameters that will be apparent to those skilled in cancer treatment.

The effect of practicing embodiments of this disclosure can be compared to any suitable reference, such as a positive or negative control. In embodiments an effect can be compared to a reference value obtained, for example, from a control cells expressing a TCR with known effects, or a TCR that is not specific for the particular antigen in question, or a TCR that is mismatched with respect to HLA type and/or T lymphocyte type, or any other suitable reference value that will be apparent to those skilled in the art when provided the benefit of this disclosure. In embodiments a suitable reference comprises a known value or range of values. In embodiments, the reference comprises a statistical value, such as an area under a curve, or another area or plot on a graph, and/or is obtained from repeated measurements.

Various and non-limiting embodiments of the disclosure are demonstrated using HLA-I and HLA-II restricted TCRs.

HLA-I Restricted TCRs

In one aspect the disclosure encompasses novel TCRs that are specific for the NY-ESO-1 antigen as presented in an HLA class I context. Specific examples of the α chain and β chain of HLA-I restricted TCRs and polynucleotide sequences encoding them are described further below as "19305DP", "AL", "KQ", "PP", "19305CD8", "BB", "KB", "ST", and "JD". These TCRs are specific for NY-ESO-1/LAGE-1-derived peptides presented by different HLA class I types, including HLA-A*02; B*27; B*35; Cw*03; and Cw*15.

HLA-II Restricted TCRs

In another aspect the disclosure encompasses novel TCRs that are specific for the NY-ESO-1 antigen as presented in an HLA class II context. Specific examples of the α chain and β chain of HLA-II restricted TCRs and polynucleotide sequences encoding them are described further below as "PB-P", "PB-T", and "PB13.2". These TCRs are specific for NY-ESO-1/LAGE-1-derived peptides presented by different HLA class II types, including HLA-DRB1*04 and DRB1*07. In certain embodiments these TCRs impart to T cells that express them the capability of direct recognition of tumors and/or cancer cells that express the NY-ESO-1/LAGE-1 antigen.

In certain aspects, the cells comprising a recombinant TCR of this disclosure that are administered to an individual are allogeneic, syngeneic, or autologous cells. Thus, in one embodiment, the cells are obtained from a first individual, modified, and administered to a second individual who is in need thereof. In another embodiment, the cells are removed from the individual prior to modification, are modified to express the recombinant TCR, and administered back to the same individual. In certain embodiments, the cells that are modified according to this disclosure comprise an immune cell population that is enriched for, comprises or consists of a particular immune cell type. In certain aspects the cells are CD4+ T cells, or are CD8+ T cells. In one aspect, the cells into which one or more expression vectors of this disclosure is introduced comprise a mixture of immune cells, such CD4+ and CD8+ T cells, and/or can comprise peripheral blood mononuclear cells (PBMCs). In one approach, one or more expression vectors which alone or together encode the 19305DP TCR is/are introduced into a mixture of immune cells. In certain embodiments, the T cells are capable of direct recognition of the cancer cells expressing the NY-ESO-1/LAGE-1 antigen. In embodiments the direct recognition comprises HLA class II-restricted binding of the TCR to the NY-ESO-1/LAGE-1 antigen expressed by the cancer cells.

With respect to 19305DP TCR, the present disclosure demonstrates certain characterizations of its expression and function. For example, FIGS. 5-7 provide characteristics of parental 19305DP clone. In particular, FIG. 5 provides evidence of the CD4/CD8 double positive characteristics. FIG. 6 provides a demonstration of CD8-independent recognition which indicates high affinity recognition by the TCR. FIG. 7 provides a demonstration of strict NY-ESO-1/LAGE-1 sequence-specificity which supports no cross-reactivity to other human antigens. FIGS. 8-10 present results demonstrating anti-tumor effects of human T cells transduced by the 19305DP-TCR, in comparison with AL-TCR, which has the same HLA-A*02:01-restriction and NY-ESO-1-specificity but is derived from a CD8 single-positive T-cell clone. FIG. 8 provides a demonstration of in vivo growth inhibition of NY-ESO-1 and HLA-A*02:01-expressing human melanoma by human peripheral blood mononuclear cells containing both CD4+ and CD8+ T cells, that were transduced by 19305DP or AL TCR-expressing retroviral vectors, demonstrating superior anti-tumor effect by 19305DP-TCR-transduced PBMCs. FIG. 9 provides a demonstration of in vitro tumor-killing ability of 19305DP and AL TCR-expressing CD4+ and CD8+ T cells, demonstrating that both CD4+ and CD8+ T cells efficiently kill NY-ESO-1+HLA-A*02:01+ cancer target when they were transduced by 19305DP-TCR, while only CD8+ T cells killed the target when they were transduced by AL-TCR. FIG. 10 provides data demonstrating in vivo tumor growth inhibition of 19305DP and AL TCR-expressing CD4+ and CD8+ T cells, demonstrating that both CD4+ and CD8+ T cells attack NY-ESO-1+ HLA-A*02:01+cancer targets when they were transduced by 19305DP-TCR, while only CD8+ T cells showed tumor growth inhibition when they were transduced by AL-TCR. Thus, in certain embodiments the disclosure relates to the ability to transduce either CD4+ T cells, or CD8+ T cells, or so-called double positive ("DP") T cells using recombinant TCRs and modified cells of this disclosure, such as cells modified to express the 19305DP TCR. With respect to DP T cells, it is known in the art that they exist at a developmental stage in the thymus. CD4+/CD8+ double positive T cells are differentiated into the CD4 lineage or the CD8 lineage by the process known as thymic positive selection, and CD4 and CD8 differentiation paths are believed to be generally mutually exclusive fates. Nevertheless, mature CD4+/CD8+ DP T cells have been described in the blood and peripheral lymphoid tissues, and have been observed in certain disorders, including cancer—although at low frequency. Without intending to be constrained by any particular theory, it is believed the present disclosure provides the first description of a TCR obtained from a DP T cell, and producing such TCR recombinantly to demonstrate its utility in adoptive immunological approaches, as demonstrated in the Examples and Figures of this disclosure. In certain embodiments, the invention provides mixtures of cells expressing TCRs, or cells expressing more than one TCR described herein, that are specific for distinct cancer antigens, thus providing cell populations that can be considered polyvalent with respect to the TCRs.

The TCRs provided by the invention are in certain examples capable of recognizing NY-ESO-1;157-170 which is an antigen that consists of the amino acid sequence SLLMWITQCFLPVF (SEQ ID NO:63), or are capable of recognizing NY-ESO-1; 95-106, which is an antigen that consists of the amino acid sequence PFATPMEAELAR (SEQ ID NO:64).

In certain embodiments, the cells provided by the invention are engineered CD8+ T cells expressing a TCR of this disclosure that can directly recognize NY-ESO-1/LAGE-1+ cancer cells, and CD4+ T cells that are capable of recognizing these NY-ESO-1/LAGE-1 antigens via TCRs which interact with the antigen in association with HLA class II molecules, wherein the HLA class II molecules are displayed by tumor cells.

The invention includes each and every polynucleotide sequence that encodes one or more TCR polypeptides of the invention and disclosed herein, including DNA and RNA sequences, and including isolated and/or recombinant polynucleotides comprising and/or consisting of such sequences. The invention also includes cells which comprise the recombinant polynucleotides. The cells can be isolated cells, cells grown and/or expanded and/or maintained in culture, and can be prokaryotic or eukaryotic cells. Prokaryotic and eukaryotic cell cultures can be used, for example, to propagate or amplify the TCR expression vectors of the invention. In embodiments, the cells can comprise packaging plasmids, which, for example, provide some or all of the proteins used for transcription and packaging of an RNA copy of the expression construct into recombinant viral particles, such as pseudoviral particles. In embodiments, the expression vectors are transiently or stably introduced into cells. In embodiments, the expression vectors are integrated into the chromosome of cells used for their production. In embodiments, polynucleotides encoding the TCRs which are introduced into cells by way of an expression vector, such as a viral particle, are integrated into one or more chromosomes of the cells. Such cells can be used for propagation, or they can be cells that are used for therapeutic and/or prophylactic approaches. The eukaryotic cells include CD4+ T cells, CD8+ T cells, natural killer T cells, γδ T cells, and their progenitor cells into which a TCR expression construct of the invention has been introduced. The CD4+ T cells can be from any source, including but not limited to a human subject who may or may not be the eventual recipient of the CD4+ T cells, CD8+ T cells, or combinations thereof, once they have been engineered to express a novel TCR according to this disclosure.

Expression vectors for use with embodiments of this disclosure can be any suitable expression vector. In embodiments, the expression vector comprises a modified viral polynucleotide, such as from an adenovirus, a herpesvirus, or a retrovirus, such as a lentiviral vector. The expression vector is not restricted to recombinant viruses and includes non-viral vectors such as DNA plasmids and in vitro transcribed mRNA.

With respect to the polypeptides that are encoded by the polynucleotides/expression vectors described above, in certain aspects the invention provides functional TCRs and expression vectors encoding them, wherein the functional TCR which comprises a TCR α and a TCR β chain, wherein the two chains are present in a physical association with one another (e.g., in a complex) and are non-covalently joined to one another, or wherein the two chains are distinct polypeptides but are covalently joined to one another, such as by a disulfide or other covalent linkage that is not a peptide bond. Other suitable linkages can comprise, for example, substituted or unsubstituted polyalkylene glycol, and combinations of ethylene glycol and propylene glycol in the form of, for example, copolymers. In other embodiments, two polypeptides that constitute the TCR α and a TCR β chain can both be included in a single polypeptide, such as a fusion protein. In certain embodiments, the fusion protein comprises a TCR α chain amino acid sequence and a TCR β chain amino acid sequence that have been translated from the same open reading frame (ORF), or distinct ORFs, or an ORF that contain a signal that results in non-continuous translation. In one embodiment, the ORF comprises a P2A-mediated translation skipping site positioned between the TCR α and TCR β chain. Constructs for making P2A containing proteins (also referred to as 2A Peptide-Linked multicistronic vectors) are known in the art. (See, for example, *Gene Transfer: Delivery and Expression of DNA and RNA, A Laboratory Manual,* (2007), Friedman et al., International Standard Book Number (ISBN) 978-087969765-5. Briefly, 2A peptide sequences, when included between coding regions, allow for stoichiometric production of discrete protein products within a single vector through a novel cleavage event that occurs in the 2A peptide sequence. 2A peptide sequences are generally short sequence comprising 18-22 amino acids and can comprise distinct amino-terminal sequences. Thus, in one embodiment, a fusion protein of the invention includes a P2A amino acid sequence. In embodiments, a fusion protein of the invention can comprise a linker sequence between the TCR α and TCR β chains. In certain embodiments, the linker sequence can comprise a GSG (Gly-Ser-Gly) linker or an SGSG (Ser-Gly-Ser-Gly) (SEQ ID NO:59) linker. In certain embodiments, the TCR α and TCR β chains are connected to one another by an amino acid sequence that comprises a furin protease recognition site, such as an RAKR (Arg-Ala-Lys-Arg) (SEQ ID NO:60) site.

In one embodiment, the expression construct that encodes the TCR can also encode additional polynucleotides. The additional polynucleotide can be such that it enables identification of TCR expressing cells, such as by encoding a detectable marker, such as a fluorescent or luminescent protein. The additional polynucleotide can be such that it encodes an element that allows for selective elimination of TCR expressing cells, such as thymidine kinase gene. In embodiments the additional polynucleotides can be such that they facilitate inhibition of expression of endogenously encoded TCRs. In an embodiment, the expression construct that encodes the TCR also encodes a polynucleotide which can facilitate RNAi-mediated down-regulation of one or more endogenous TCRs. For example, see Okamoto S, et al. (2009) Cancer Research, 69:9003-9011, and Okamoto S, et al. (2012). Molecular Therapy-Nucleic Acids, 1, e63. In an embodiment, the expression construct that encodes the TCR can encode an shRNA or an siRNA targeted to an endogenously encoded TCR. In an alternative embodiment, a second, distinct expression construct that encodes the polynucleotide for use in downregulating endogenous TCR production can be used.

In certain approaches distinct TCR chains can be expressed from an expression construct such that the β chain is oriented N-terminally in relation to the α chain, and thus TCRs of the invention can also comprise this chain orientation, or other orientations. In alternative embodiments, the TCR α and β chain proteins can be expressed from distinct expression vectors introduced into the same cell. In certain embodiments, mRNA encoding TCRs can be used as an alternative to expression vectors.

With respect to use of the engineered CD4⁻ T cells, CD8+ T cells, and combinations thereof, the method generally comprises administering an effective amount (typically $10^{10}$ cells by intravenous or intraperitoneal injections) of a composition comprising the CD4⁺ T cells to an individual in need thereof. An individual in need thereof, in various embodiments, is an individual who has or is suspected of having, or is at risk for developing a cancer which is characterized by malignant cells that express NY-ESO-1/LAGE-1. As is well known in the art, NY-ESO-1/LAGE-1 is expressed by a variety of cancer cells and tumor types. In particular and non-limiting examples, such cancers include cancers of the bladder, brain, breast, ovary, non-small cell lung cancer, myeloma, prostate, sarcoma and melanoma. Specific embodiments include but are not limited to liposarcomas and intrahepatic cholagiocarcinoma. The individual may have early-stage or advanced forms of any of these cancers, or may be in remission from any of these cancers. In one embodiment, the individual to whom a composition of the invention is administered is at risk for recurrence for any cancer type that expresses NY-ESO-1. In certain embodiments, the individual has or is suspected of having, or is at risk for developing or recurrence of a tumor comprising cells which express a protein comprising the amino acid sequences defined by NY-ESO-1:157-170 and/or NY-ESO-1:95-106. In embodiments, the disclosure includes recombinant TCRs that are specific for peptide fragments of NY-ESO-1 that are between 15 and 24 amino acid residues long, wherein such peptides are presented in a complex with HLA-II. In embodiments, the disclosure includes recombinant TCRs that are specific for peptides that are in a complex with HLA-I, or HLA-II, wherein the peptides comprise or consist of the amino acid sequences of NY-ESO-1:157-170 and/or NY-ESO-1:95-106.

The nucleotide and amino acid sequences presented below represent those used to demonstrate the invention. As described above, the invention includes any and all polynucleotide sequences encoding the amino acid sequences of the TCR constructs described herein. Further, variations in amino acid sequences in the TCRs are contemplated, so long as they do not adversely affect the function of the TCR. In various embodiments, a TCR comprising one or more amino acid changes as compared to the sequences presented herein will comprise conservative amino acid substitutions or other substitutions, additions or deletions, so long as the cells expressing the recombinant TCRs of the invention can directly and specifically recognize tumor cells that express NY-ESO-1/LAGE-1, wherein that recognition is dependent on expression of NY-ESO-1/LAGE-1 and presentation of peptides processed from it in an HLA class II restricted manner by the tumor cells. In embodiments, a TCR of the present invention comprises any amino acid sequence that facilitates direct recognition of the tumor antigen on the tumor cells, without participation of an antigen presenting cells. In embodiments, the amino acid sequence of a TCR provided by this disclosure is at least 95%, 96%, 97%, 98% or 99% similar to an amino acid sequences provided in the sequence listing that is part of this disclosure. In various embodiments, any TCR of the invention can have a $K_{off}$ value for its cognate epitope as defined herein that is essentially the same as the $K_{off}$ for the cognate epitope exhibited by a TCR of a naturally occurring TCR for the same epitope. In embodiments, the TCR amino acid sequences can comprise changes in their constant region. In this regard, it is known in the art that in general, the constant region of a TCR does not substantially contribute to antigen recognition. For example, it is possible to replace a portion of the human constant region of a TCR with a murine sequence and retain function of the TCR. (See, for example, Goff S L et al. (2010) Cancer Immunology, Immunotherapy, 59: 1551-1560). Thus, various modifications to the TCR sequences disclosed herein are contemplated, and can include but are not limited to changes that improve specific chain pairing, or facilitate stronger association with T cell signaling proteins of the CD3 complex, or inhibit formation of dimers between the endogenous and introduced TCRs. In embodiments, the amino acid changes can be present in the CDR region, such as the CDR3 region, including but not necessarily limited to substitutions of one, two, three, or more amino acids in the CDR3 sequence. In embodiments, the amino acid changes have no effect on the function of the TCR. The mature TCR proteins are preceded by the amino acid sequences termed a signal peptide or a leader peptide, which direct newly synthesized TCR proteins to the secretory pathway. A signal peptide is removed from the mature TCR protein before cell surface expression. Therefore, replacement of the signal peptide with other natural or artificial sequence does not alter function of mature TCR. Thus, various modifications to the signal peptide sequences disclosed herein are contemplated, including but not limited to deleting or changing some or all of the amino acids is in the signal peptide, or replacing all or some of the amino acids with other amino acids and/or polypeptide sequences, examples of which will be apparent to those skilled in the art given the benefit of the present disclosure. In certain aspects, the disclosure includes expression vectors and other polynucleotides encoding one or more TCR hypervariable, or complementarity determining regions (CDRs) from the TCR alpha chain, beta chain, or a combination thereof. In certain embodiments only one CDR is encoded, or only two CDRs are encoded, or only three CDRs are encoded, or a combination of only certain CDRs from the TCR alpha and beta chains are encoded, and all such combinations of TCR CDR segments and polynucleotides encoding them from the TCR alpha and beta chains described herein are encompassed by this disclosure. Those skilled in the art will be able to recognize TCR CDR segments of each of the TCR amino acid sequence presented herein.

Libraries

The disclosure includes a plurality of expression vectors encoding TCRs, i.e., a library comprising a plurality of distinct expression vectors encoding distinct TCRs, wherein at least one member of the library encodes a novel α-chain, and/or a novel β-chain of a TCR of this disclosure. Thus, at least one member of the library can be selected from expression vectors that encode the a chain and/or chain of at least one of the HLA-I restricted TCRs referred to herein as AL, KQ, PP, 19305CD8, BB, KB, ST, JD, and 19305DP, and at least member of the library can be selected from expression vectors that encode the a chain and/or 13 chain of at least one of the novel HLA-II restricted TCRs described herein PB-P, PB-T, PB13.2. Combinations of distinct expression vectors encoding these HLA-I and HLA-II restricted TCRs are included in the disclosure.

In one non-limiting example a library of this disclosure comprises an expression vector encoding the TCR described herein as 19305DP, which is an HLA-A*02-restricted TCR and is functional in both CD4+ and CD8+ T cells. This TCR was initially obtained from a unique tumor antigen-specific T cells that were CD4+CD8+ double-positive, and this is believed to be the first description of such a TCR. The AL, KQ, PP, 19305CD8, BB, KB, ST, and JD TCR genes were initially obtained from CD8+ single-positive T cells, and PB-P, PB-T and PB13.2 were from CD4+ single-positive T cells.

In certain aspects, in addition at least one novel TCR/expression vector described herein, a library provided by this disclosure can further comprise expression vectors encoding HLA class II restricted TCRs selected from the TCRs described below as "JM", "5B8" that are HLA DPB1*04-restricted and DRB1*01-restricted "SB95". These constructs are described in PCT/US14/25673, published as WO/2014/160030, from which the description of the TCRs, expression vectors encoding the TCRs, and methods of making and using the TCRs and expression vectors are incorporated herein by reference. The JM, 5B8 and SB95 TCRs were obtained from NY-ESO-1 positive individuals, and these TCRs confer onto T cells, including CD4+ T cells, the ability to directly recognize NY-ESO-1+ cancer cells, as described further below, including but not necessarily limited to PB-P, PB-T and PB13.2. Thus, these TCRs impart to T cells the capability to directly recognize a cancer cell expressing a NY-ESO-1/LAGE-1 antigen, wherein the direct recognition of the cancer cell comprises human leukocyte antigen HLA class II-restricted binding of the TCR to the NY-ESO-1/LAGE-1 antigen expressed by the cancer cell.

In various embodiments an expression vector library of this disclosure encodes a diversity of TCRs. In certain aspects, the expression vectors do not comprise any phage or phagemid DNA, and/or none of the TCR polypeptide(s) comprises any phage or phagemid protein. In embodiments the TCRs do not comprise any phage or phagemid protein and thus are not components of, for example, a TCR phage display library.

In certain examples expression vectors in a TCR expression vector library of this disclosure encode a plurality of TCRs such that cells expressing the TCRs can function in a diversity of patients with distinct HLA class I types, HLA class II types, and/or combinations thereof.

In certain embodiments HLA class I-restricted TCRs encoded by an expression vector library of this disclosure are capable of functioning in patients with an HLA class I type selected from an allele encompassed by HLA-A, -B, -C, and combinations thereof. In certain embodiments, the library is sufficiently diverse to be suitable for use in cancer therapy in at least 50% of the U.S. Caucasian population at the time of the filing of this application or patent. In certain aspects, a library of this disclosure is suitable for use in cancer therapy on the basis of HLA-class I (A*02/B*35/C*04) restricted TCRs, which without intending to be bound by any particular theory is believed to comprise 67% of the HLA types of the U.S Caucasian population at the time of the filing of this application or patent, and HLA class II (DR*01/DR*04/DR*07/DP*04) restricted TCRs, which also without intending to be bound by any particular theory is believed to comprise 87% of the HLA types of U.S Caucasian population at the time of the filing of this application or patent. In certain embodiments a TCR library of this disclosure comprises TCRs specific for the 10 most frequently occurring HLA types in the U.S Caucasian population at the time of the filing of this application or patent, and thus may be suitable for use in cancer therapy at least 90%, 91%, 92%, 93%, 94%, 95%, 96%, 97%, 98%, 99%, or more of the human population. In certain embodiments, the disclosure provides a TCR library that is restricted to a plurality of NY-ESO-1 specify TCRs that are restricted by HLA types set forth in Table 1. In embodiments, the library comprises TCRs that are restricted by one or a combination of the underlined HLA types in Table 1. In certain aspects the disclosure includes a library of 2 -3,000 distinct expression vectors encoding distinct TCRs.

In certain embodiments, expression vectors in a TCR expression vector library of this disclosure encode a range of TCRs such that cells expressing the TCRs can function in a diversity of patients with an HLA class II type selected from an allele encompassed by HLA-DP, -DM, -DOA, -DOB, -DQ, -DR, and combinations thereof.

In embodiments, an expression vector library of this disclosure comprises at least two expression vectors encoding at least two distinct TCRs, at least one of which is selected from 19305DP, AL, KQ, PP, 19305CD8, BB, KB, ST, JD, PB-P, PB-T, and PB13.2. In an embodiment an expression vector library of this disclosure includes an expression vector encoding the alpha chain, the beta chain, or both alpha and beta chains of 19305DP.

In certain embodiments, the disclosure comprises a library of distinct expression vectors. In one example, each expression vector can be contained as an isolated DNA preparation, or can be maintained, for example, in a cell culture. Such compositions can be preserved in, for example, separately sealed containers, such as glass or plastic vials, Eppendorf tubes, etc., and can be kept under a reduced temperature, such as a temperature of zero degrees C., or lower. Each separate container or location where a container is kept can comprise indicia of the expression vector(s) in the container. Such indicia can include but are not limited to human or machine perceptible material, such a printed label, a bar code a QR code, and the like, or any other indicia that is useful for identifying the contents/location of the expression vector, and which can be used for retrieving a TCR for use in a method of this disclosure. In certain aspects, the disclosure includes a plurality of distinct containers comprising distinct TCRs, wherein each container is indexed, and wherein the indicia of the containers is maintained in a database. The database can be digitized and can be adapted such that it is integrated with software. In certain aspects, the disclosure provides a computer based method for selecting a TCR from a library of this disclosure, the method comprising using a processor to match an input HLA type of an individual or sample or other HLA information with a TCR in the library that is compatible with said HLA type. In certain implementations, the disclosure can exclude computer based approaches that include signals, carrier waves, or transitory signals.

In one aspect the disclosure includes a system comprising a library of TCRs, and a database comprising indicia of the nucleotide and/or sequences and/or HLA type of the TCRs, the database in communication with a processor, wherein the processor is programmed to select and/or designate a suitable TCR in the library that is matched with the HLA type of a sample. The system may further comprise an apparatus for retrieval of a container that contains the matched TCR, including but not necessarily a robotized apparatus that can, for example, be directed to the indicia of the suitable TCR, and can select and/or retrieve the indicated TCR from the library. In another aspect the disclosure provides a computer readable medium comprising a database of populated with information about a TCR library of this disclosure. In an embodiment, the disclosure include a computer-readable medium comprising a set of instructions for a computer to select a TCR from a TCR library of this disclosure, wherein the TCR is matched to the HLA type of a sample.

In one aspect the disclosure comprises receiving an indication of the HLA type of an individual diagnosed with a NY-ESO-1/LAGE-1 positive cancer, selecting an expression vector from a library of this disclosure based on the HLA type, and distributing the expression vector to a party for use in introducing the expression vector into immune cells of the diagnosed individual. The distributing the expression vector can comprise transporting the expression vector using any suitable approach.

In one aspect the disclosure comprises selecting an expression vector from a library of this disclosure and introducing the expression vector into immune cells obtained from an individual diagnosed with a NY-ESO-/LAGE-11 positive cancer, wherein the HLA type of the TCR encoded by the expression vector is matched to the HLA type of the individual. In embodiments the disclosure further comprises introducing the immune cells into an individual in need thereof, which may be the individual who was diagnosed with the NY-ESO-1/LAGE-1 positive cancer, or may be an individual with the same HLA type as the diagnosed individual.

In one aspect the disclosure comprises testing a sample from an individual to determine whether or not the individual has a NY-ESO-1/LAGE-1 positive cancer, and subsequent to a determination that the individual has the NY-ESO-1/LAGE-1 positive cancer, selecting an expression vector from a library of this disclosure based on the HLA type of the individual, and introducing the expression vector into immune cells of the individual.

The following examples are intended to illustrate but not limit the invention.

EXAMPLE 1

In specific and illustrative embodiments, the polynucleotide sequences encoding the TCRs of the invention, and the amino acid sequences of the TCR α and TCR β chains encoded by the polynucleotides are as follows. Representative and non-limiting examples demonstrating cloning and use of the TCRs is presented in FIGS. 1-4.

HLA-A*02-Restricted NY-ESO-1$_{157-165}$-Specific T-Cell Clone "AL"

1. Nucleotide Sequence

TCR α chain (SEQ ID NO: 65)
ATGATGAAATCCTTGAGAGTTTTACTAGTGATCCTGTGGCTTCAGTT

GAGCTGGGTTTGGAGCCAACAGAAGGAGGTGGAGCAGAATTCTGGAC

CCCTCAGTGTTCCAGAGGGAGCCATTGCCTCTCTCAACTGCACTTAC

AGTGACCGAGGTTCCCAGTCCTTCTTCTGGTACAGACAATATTCTGG

GAAAAGCCCTGAGTTGATAATGTCCATATACTCCAATGGTGACAAAG

AAGATGGAAGGTTTACAGCACAGCTCAATAAAGCCAGCCAGTATGTT

TCTCTGCTCATCAGAGACTCCCAGCCCAGTGATTCAGCCACCTACCT

CTGTGCCGTGGGGGGACTTACCTCTAGCAACACAGGCAAACTAATCT

TTGGGCAAGGGACAACTTTACAAGTAAAACCAGATATCCAGAACCCT

GACCCTGCCGTGTACCAGCTGAGAGACTCTAAATCCAGTGACAAGTC

TGTCTGCCTATTCACCGATTTTGATTCTCAAACAAATGTGTCACAAA

GTAAGGATTCTGATGTGTATATCACAGACAAAACTGTGCTAGACATG

-continued

```
AGGTCTATGGACTTCAAGAGCAACAGTGCTGTGGCCTGGAGCAACAA
ATCTGACTTTGCATGTGCAAACGCCTTCAACAACAGCATTATTCCAG
AAGACACCTTCTTCCCCAGCCCAGAAAGTTCCTGTGATGTCAAGCTG
GTCGAGAAAAGCTTTGAAACAGATACGAACCTAAACTTTCAAAACCT
GTCAGTGATTGGGTTCCGAATCCTCCTCCTGAAAGTGGCCGGGTTTA
ATCTGCTCATGACGCTGCGGCTGTGGTCCAGCTGA
```

TCR β chain
(SEQ ID NO: 66)
```
ATGGGAATCAGGCTCCTCTGTCGTGTGGCCTTTTGTTTCCTGGCTGT
AGGCCTCGTAGATGTGAAAGTAACCCAGAGCTCGAGATATCTAGTCA
AAAGGACGGGAGAGAAAGTTTTTCTGGAATGTGTCCAGGATATGGAC
CATGAAAATATGTTCTGGTATCGACAAGACCCAGGTCTGGGGCTACG
GCTGATCTATTTCTCATATGATGTTAAAATGAAAGAAAAAGGAGATA
TTCCTGAGGGGTACAGTGTCTCTAGAGAGAAGGAGCGCTTCTCC
CTGATTCTGGAGTCCGCCAGCACCAACCAGACATCTATGTACCTCTG
TGCCAGCAGTAACCAGATCTATGGCTACACCTTCGGTTCGGGGACCA
GGTTAACCGTTGTAGAGGACCTGAACAAGGTGTTCCCACCCGAGGTC
GCTGTGTTTGAGCCATCAGAAGCAGAGATCTCCCACACCCAAAAGGC
CACACTGGTGTGCCTGGCCACAGGCTTCTTCCCTGACCACGTGGAGC
TGAGCTGGTGGGTGAATGGGAAGGAGGTGCACAGTGGGGTCAGCACG
GACCCGCAGCCCCTCAAGGAGCAGCCCGCCCTCAATGACTCCAGATA
CTGCCTGAGCAGCCGCCTGAGGGTCTCGGCCACCTTCTGGCAGAACC
CCCGCAACCACTTCCGCTGTCAAGTCCAGTTCTACGGGCTCTCGGAG
AATGACGAGTGGACCCAGGATAGGGCCAAACCCGTCACCCAGATCGT
CAGCGCCGAGGCCTGGGGTAGAGCAGACTGTGGCTTTACCTCGGTGT
CCTACCAGCAAGGGGTCCTGTCTGCCACCATCCTCTATGAGATCCTG
CTAGGGAAGGCCACCCTGTATGCTGTGCTGGTCAGCGCCCTTGTGTT
GATGGCCATGGTCAAGAGAAAGGATTTCTGA
```

2. Amino Acid Sequence of AL (Starting From Start Codon-Coding Methionine to Stop Codon-Coding Termination (*))

TCR α chain
(SEQ ID NO: 5)
MMKSLRVLLVILWLQLSWVWSQQKEVEQNSGPLSVPEGAIASLNCTY
SDRGSQSFFWYRQYSGKSPELIMSIYSNGDKEDGRFTAQLNKASQYV
SLLIRDSQPSDSATYLCAVGGLTSSNTGKLIFGQGTTLQVKPDIQNP
DPAVYQLRDSKSSDKSVCLFTDFDSQTNVSQSKDSDVYITDKTVLDM
RSMDFKSNSAVAWSNKSDFACANAFNNSIIPEDTFFPSPESSCDVKL
VEKSFETDTNLNFQNLSVIGFRILLLKVAGFNLLMTLRLWSS*

TCR β chain
(SEQ ID NO: 6)
MGIRLLCRVAFCFLAVGLVDVKVTQSSRYLVKRTGEKVFLECVQDMD
HENMFWYRQDPGLGLRLIYFSYDVKMKEKGDIPEGYSVSREKKERFS
LILESASTNQTSMYLCASSNQIYGYTFGSGTRLTVVEDLNKVFPPEV
AVFEPSEAEISHTQKATLVCLATGFFPDHVELSWWVNGKEVHSGVST
DPQPLKEQPALNDSRYCLSSRLRVSATFWQNPRNHFRCQVQFYGLSE
NDEWTQDRAKPVTQIVSAEAWGRADCGFTSVSYQQGVLSATILYEIL
LGKATLYAVLVSALVLMAMVKRKDF*

HLA-B*35-Restricted NY-ESO-1$_{94-102}$-Specific T-Cell Clone "KQ"

1. Nucleotide Sequence

TCR α chain
(SEQ ID NO: 7)
```
ATGATGGCAGGCATTCGAGCTTTATTTATGTACTTGTGGCTGCAGCT
GGACTGGGTGAGCAGAGGAGAGTGTGGGGCTGCATCTTCCTACCC
TGAGTGTCCAGGAGGGTGACAACTCTATTATCAACTGTGCTTATTCA
AACAGCGCCTCAGACTACTTCATTTGGTACAAGCAAGAATCTGGAAA
AGGTCCTCAATTCATTATAGACATTCGTTCAAATATGGACAAAAGGC
AAGGCCAAAGAGTCACCGTTTTATTGAATAAGACAGTGAAACATCTC
TCTCTGCAAATTGCAGCTACTCAACCTGGAGACTCAGCTGTCTACTT
TTGTGCAGAGAATACCGCCCCACATAATGCAGGCAACATGCTCACCT
TTGGAGGGGAACAAGGTTAATGGTCAAACCCCATATCCAGAACCCT
GACCCTGCCGTGTACCAGCTGAGAGACTCTAAATCCAGTGACAAGTC
TGTCTGCCTATTCACCGATTTTGATTCTCAAACAAATGTGTCACAAA
GTAAGGATTCTGATGTGTATATCACAGACAAAACTGTGCTAGACATG
AGGTCTATGGACTTCAAGAGCAACAGTGCTGTGGCCTGGAGCAACAA
ATCTGACTTTGCATGTGCAAACGCCTTCAACAACAGCATTATTCCAG
AAGACACCTTCTTCCCCAGCCCAGAAAGTTCCTGTGATGTCAAGCTG
GTCGAGAAAAGCTTTGAAACAGATACGAACCTAAACTTTCAAAACCT
GTCAGTGATTGGGTTCCGAATCCTCCTCCTGAAAGTGGCCGGGTTTA
ATCTGCTCATGACGCTGCGGCTGTGGTCCAGCTGA
```

TCR β chain
(SEQ ID NO: 8)
```
ATGGGCCCTGGCTCCTCTGCTGGGTGCTGCTTTGTCTCCTGGGAGC
AGGCCCAGTGGACGCTGGAGTCACCCAAAGTCCCACACACCTGATCA
AAACGAGAGGACAGCAAGTGACTCTGAGATGCTCTCCTATCTCTGGG
CACAAGAGTGTGTCCTGGTACCAACAGGTCCTGGGTCAGGGGCCCCA
GTTTATCTTTCAGTATTATGAGAAAGAAGAGAGAGGAAGAGGAAACT
TCCCTGATCGATTCTCAGCTCGCCAGTTCCCTAACTATAGCTCTGAG
CTGAATGTGAACGCCTTGTTGCTGGGGGACTCGGCCCTGTATCTCTG
TGCCAGCAGCTACGACAGGGGATAAACTATGGCTACACCTTCGGTT
CGGGGACCAGGTTAACCGTTGTAGAGGACCTGAACAAGGTGTTCCCA
CCCGAGGTCGCTGTGTTTGAGCCATCAGAAGCAGAGATCTCCCACAC
CCAAAAGGCCACACTGGTGTGCCTGGCCACAGGCTTCTTCCCTGACC
ACGTGGAGCTGAGCTGGTGGGTGAATGGGAAGGAGGTGCACAGTGGG
GTCAGCACGGACCCGCAGCCCCTCAAGGAGCAGCCCGCCCTCAATGA
```

-continued
```
CTCCAGATACTGCCTGAGCAGCCGCCTGAGGGTCTCGGCCACCTTCT
GGCAGAACCCCCGCAACCACTTCCGCTGTCAAGTCCAGTTCTACGGG
CTCTCGGAGAATGACGAGTGGACCCAGGATAGGGCCAAACCCGTCAC
CCAGATCGTCAGCGCCGAGGCCTGGGGTAGAGCAGACTGTGGCTTTA
CCTCGGTGTCCTACCAGCAAGGGGTCCTGTCTGCCACCATCCTCTAT
GAGATCCTGCTAGGGAAGGCCACCCTGTATGCGTGCTGGTCAGCGC
CCTTGTGTTGATGGCCATGGTCAAGAGAAAGGATTTCTGA
```

2. Amino Acid Sequence For KQ (Starting From Start Codon-Coding Methionine to Stop Codon-Coding Termination (*))

TCR α chain
(SEQ ID NO: 9)
```
MMAGIRALFMYLWLQLDWVSRGESVGLHLPTLSVQEGDNSIINCAYS
NSASDYFIWYKQESGKGPQFIIDIRSNMDKRQGQRVTVLLNKTVKHL
SLQIAATQPGDSAVYFCAENTAPHNAGNMLTFGGGTRLMVKPHIQNP
DPAVYQLRDSKSSDKSVCLFTDFDSQTNVSQSKDSDVYITDKTVLDM
RSMDFKSNSAVAWSNKSDFACANAFNNSIIPEDTFFPSPESSCDVKL
VEKSFETDTNLNFQNLSVIGFRILLLKVAGFNLLMTLRLWSS*
```

TCR β chain
(SEQ ID NO: 10)
```
MGPGLLCWVLLCLLGAGPVDAGVTQSPTHLIKTRGQQVTLRCSPISG
HKSVSWYQQVLGQGPQFIFQYYEKEERGRGNFPDRFSARQFPNYSSE
LNVNALLLGDSALYLCASSYDRGINYGYTFGSGTRLTVVEDLNKVFP
PEVAVFEPSEAEISHTQKATLVCLATGFFPDHVELSWWVNGKEVHSG
VSTDPQPLKEQPALNDSRYCLSSRLRVSATFWQNPRNHFRCQVQFYG
LSENDEWTQDRAKPVTQIVSAEAWGRADCGFTSVSYQQGVLSATILY
EILLGKATLYAVLVSALVLMAMVKRKDF*
```

HLA-B*35-Restricted NY-ESO-1₉₄₋₁₀₄-Specific T-Cell Clone "PP"

1. Nucleotide Sequence

TCR α chain
(SEQ ID NO: 11)
```
ATGGCCTCTGCACCCATCTCGATGCTTGCGATGCTCTTCACATTGAG
TGGGCTGAGAGCTCAGTCAGTGGCTCAGCCGGAAGATCAGGTCAACG
TTGCTGAAGGGAATCCTCTGACTGTGAAATGCACCTATTCAGTCTCT
GGAAACCCTTATCTTTTTTGGTATGTTCAATACCCCAACCGAGGCCT
CCAGTTCCTTCTGAAATACATCACAGGGGATAACCTGGTTAAAGGCA
GCTATGGCTTTGAAGCTGAATTTAACAAGAGCCAAACCTCCTTCCAC
CTGAAGAAACCATCTGCCCTTGTGAGCGACTCCGCTTTGTACTTCTG
TGCTGTGAGAGATGTTGTGGAGGGGAAATTGCAGTTTGGAGCAGGGA
CCCAGGTTGTGGTCACCCCAGATATCCAGAACCCTGACCCTGCCGTG
TACCAGCTGAGAGACTCTAAATCCAGTGACAAGTCTGTCTGCCTATT
CACCGATTTTGATTCTCAAACAAATGTGTCACAAAGTAAGGATTCTG
ATGTGTATATCACAGACAAAACTGTGCTAGACATGAGGTCTATGGAC
TTCAAGAGCAACAGTGCTGTGGCCTGGAGCAACAAATCTGACTTTGC
ATGTGCAAACGCCTTCAACAACAGCATTATTCCAGAAGACACCTTCT
TCCCCAGCCCAGAAAGTTCCTGTGATGTCAAGCTGGTCGAGAAAAGC
TTTGAAACAGATACGAACCTAAACTTTCAAAACCTGTCAGTGATTGG
GTTCCGAATCCTCCTCCTGAAAGTGGCCGGGTTTAATCTGCTCATGA
CGCTGCGGCTGTGGTCCAGCTGA
```

TCR β chain
(SEQ ID NO: 12)
```
ATGGGCACCAGCCTCCTCTGCTGGATGGCCCTGTGTCTCCTGGGGGC
AGATCACGCAGATACTGGAGTCTCCCAGGACCCCAGACACAAGATCA
CAAAGAGGGGACAGAATGTAACTTTCAGGTGTGATCCAATTTCTGAA
CACAACCGCCTTTATTGGTACCGACAGACCCTGGGGCAGGGCCCAGA
GTTTCTGACTTACTTCCAGAATGAAGCTCAACTAGAAAAATCAAGGC
TGCTCAGTGATCGGTTCTCTGCAGAGAGGCCTAAGGGATCTTTCTCC
ACCTTGGAGATCCAGCGCACAGAGCAGGGGGACTCGGCCATGTATCT
CTGTGCCAGCAGCACCACAAGCTCCTACGAGCAGTACTTCGGGCCGG
GCACCAGGCTCACGGTCACAGAGGACCTGAAAAACGTGTTCCCACCC
GAGGTCGCTGTGTTTGAGCCATCAGAAGCAGAGATCTCCCACACCCA
AAAGGCCACACTGGTGTGCCTGGCCACAGGCTTCTACCCCGACCACG
TGGAGCTGAGCTGGTGGGTGAATGGGAAGGAGGTGCACAGTGGGGTC
AGCACAGACCCGCAGCCCCTCAAGGAGCAGCCCGCCCTCAATGACTC
CAGATACTGCCTGAGCAGCCGCCTGAGGGTCTCGGCCACCTTCTGGC
AGAACCCCGCAACCACTTCCGCTGTCAAGTCCAGTTCTACGGGCTC
TCGGAGAATGACGAGTGGACCCAGGATAGGGCCAAACCTGTCACCCA
GATCGTCAGCGCCGAGGCCTGGGGTAGAGCAGACTGTGGCTTCACCT
CCGAGTCTTACCAGCAAGGGGTCCTGTCTGCCACCATCCTCTATGAG
ATCTTGCTAGGGAAGGCCACCTTGTATGCCGTGCTGGTCAGTGCCCT
CGTGCTGATGGCCATGGTCAAGAGAAAGGATTCCAGAGGCTAG
```

2. Amino Acid Sequence for PP (Starting From Start Codon-Coding Methionine to Stop Codon-Coding Termination (*))

TCR α chain
(SEQ ID NO: 13)
```
MASAPISMLAMLFTLSGLRAQSVAQPEDQVNVAEGNPLTVKCTYSVS
GNPYLFWYVQYPNRGLQFLLKYITGDNLVKGSYGFEAEFNKSQTSFH
LKKPSALVSDSALYFCAVRDVVEGKLQFGAGTQVVVTPDIQNPDPAV
YQLRDSKSSDKSVCLFTDFDSQTNVSQSKDSDVYITDKTVLDMRSMD
FKSNSAVAWSNKSDFACANAFNNSIIPEDTFFPSPESSCDVKLVEKS
FETDTNLNFQNLSVIGFRILLLKVAGFNLLMTLRLWSS*
```

TCR β chain
(SEQ ID NO: 14)
```
MGTSLLCWMALCLLGADHADTGVSQDPRHKITKRGQNVTFRCDPISE
HNRLYWYRQTLGQGPEFLTYFQNEAQLEKSRLLSDRFSAERPKGSFS
```

```
TLEIQRTEQGDSAMYLCASSTTSSYEQYFGPGTRLTVTEDLKNVFPP
EVAVFEPSEAEISHTQKATLVCLATGFYPDHVELSWWVNGKEVHSGV
STDPQPLKEQPALNDSRYCLSSRLRVSATFWQNPRNHFRCQVQFYGL
SENDEWTQDRAKPVTQIVSAEAWGRADCGFTSESYQQGVLSATILYE
ILLGKATLYAVLVSALVLMAMVKRKDSRG*
```

HLA-B*27-Restricted NY-ESO-1$_{51-70}$-Specific T-Cell Clone "19305CD8"

1. Nucleotide Sequence
TCR α Chain

```
                                      (SEQ ID NO: 43)
ATGGAAACTCTCCTGGGAGTGTCTTTGGTGATTCTATGGCTTCAACT
GGCTAGGGTGAACAGTCAACAGGGAGAAGAGGATCCTCAGGCCTTGA
GCATCCAGGAGGGTGAAAATGCCACCATGAACTGCAGTTACAAAACT
AGTATAAACAATTTACAGTGGTATAGACAAAATTCAGGTAGAGGCCT
TGTCCACCTAATTTTAATACGTTCAAATGAAAGAGAGAAACACAGTG
GAAGATTAAGAGTCACGCTTGACACTTCCAAGAAAAGCAGTTCCTTG
TTGATCACGGCTTCCCGGGCAGCAGACACTGCTTCTTACTTCTGTGC
TACGGACGCCGTCGTGGGTGCTGACGGACTCACCTTTGGCAAAGGGA
CTCATCTAATCATCCAGCCCTATATCCAGAACCCTGACCCTGCCGTG
TACCAGCTGAGAGACTCTAAATCCAGTGACAAGTCTGTCTGCCTATT
CACCGATTTTGATTCTCAAACAAATGTGTCACAAAGTAAGGATTCTG
ATGTGTATATCACAGACAAAACTGTGCTAGACATGAGGTCTATGGAC
TTCAAGAGCAACAGTGCTGTGGCCTGGAGCAACAAATCTGACTTTGC
ATGTGCAAACGCCTTCAACAACAGCATTATTCCAGAAGACACCTTCT
TCCCCAGCCCAGAAAGTTCCTGTGATGTCAAGCTGGTCGAGAAAGC
TTTGAAACAGATACGAACCTAAACTTTCAAAACCTGTCAGTGATTGG
GTTCCGAATCCTCCTCCTGAAAGTGGCCGGGTTTAATCTGCTCATGA
CGCTGCGGCTGTGGTCCAGCTGA
TCR β chain
                                      (SEQ ID NO: 44)
ATGCTGCTGCTTCTGCTGCTTCTGGGGCCAGGCTCCGGGCTTGGTGC
TGTCGTCTCTCAACATCCGAGCTGGGTTATCTGTAAGAGTGGAACCT
CTGTGAAGATCGAGTGCCGTTCCCTGGACTTTCAGGCCACAACTATG
TTTTGGTATCGTCAGTTCCCGAAACAGAGTCTCATGCTGATGGCAAC
TTCCAATGAGGGCTCCAAGGCACATACGAGCAAGGCGTCGAGAAGG
ACAAGTTTCTCATCAACCATGCAAGCCTGACCTTGTCCACTCTGACA
GTGACCAGTGCCCATCCTGAAGACAGCAGCTTCTACATCTGCAGTGC
TAGAGACCGGGACATAGGACCCTTAGATACGCAGTATTTTGGCCCAG
GCACCCGGCTGACAGTGCTCGAGGACCTGAAAAACGTGTTCCCACCC
GAGGTCGCTGTGTTTGAGCCATCAGAAGCAGAGATCTCCCACACCCA
AAAGGCCACACTGGTGTGCCTGGCCACAGGCTTCTACCCCGACCACG
TGGAGCTGAGCTGGTGGGTGAATGGGAAGGAGGTGCACAGTGGGGTC
AGCACAGACCCGCAGCCCCTCAAGGAGCAGCCCGCCCTCAATGACTC
CAGATACTGCCTGAGCAGCCGCCTGAGGGTCTCGGCCACCTTCTGGC
AGAACCCCCGCAACCACTTCCGCTGTCAAGTCCAGTTCTACGGGCTC
TCGGAGAATGACGAGTGGACCCAGGATAGGGCCAAACCTGTCACCCA
GATCGTCAGCGCCGAGGCCTGGGGTAGAGCAGACTGTGGCTTCACCT
CCGAGTCTTACCAGCAAGGGGTCCTGTCTGCCACCATCCTCTATGAG
ATCTTGCTAGGGAAGGCCACCTTGTATGCCGTGCTGGTCAGTGCCCT
CGTGCTGATGGCCATGGTCAAGAGAAAGGATTCCAGAGGCTAG
```

2. Amino Acid Sequence for 19305CD8 (Starting From Start Codon-Coding Methionine to Stop Codon-Coding Termination (*))

TCR α chain
```
                                      (SEQ ID NO: 45)
METLLGVSLVILWLQLARVNSQQGEEDPQALSIQEGENATMNCSYKT
SINNLQWYRQNSGRGLVHLILIRSNEREKHSGRLRVTLDTSKKSSSL
LITASRAADTASYFCATDAVVGADGLTFGKGTHLIIQPYIQNPDPAV
YQLRDSKSSDKSVCLFTDFDSQTNVSQSKDSDVYITDKTVLDMRSMD
FKSNSAVAWSNKSDFACANAFNNSIIPEDTFFPSPESSCDVKLVEKS
FETDTNLNFQNLSVIGFRILLLKVAGFNLLMTLRLWSS*
```

TCR β chain
```
                                      (SEQ ID NO: 46)
MLLLLLLLGPGSGLGAVVSQHPSWVICKSGTSVKIECRSLDFQATTM
FWYRQFPKQSLMLMATSNEGSKATYEQGVEKDKFLINHASLTLSTLT
VTSAHPEDSSFYICSARDRDIGPLDTQYFGPGTRLTVLEDLKNVFPP
EVAVFEPSEAEISHTQKATLVCLATGFYPDHVELSWWVNGKEVHSGV
STDPQPLKEQPALNDSRYCLSSRLRVSATFWQNPRNHFRCQVQFYGL
SENDEWTQDRAKPVTQIVSAEAWGRADCGFTSESYQQGVLSATILYE
ILLGKATLYAVLVSALVLMAMVKRKDSRG*
```

HLA-Cw*15-Restricted NY-ESO-1$_{127-135}$-Specific T-Cell Clone "BB"

1. Nucleotide Sequence

TCR α chain
>BBA-2
```
                                      (SEQ ID NO: 15)
ATGATGGCAGGCATTCGAGCTTTATTTATGTACTTGTGGCTGCAGCT
GGACTGGGTGAGCAGAGGAGAGAGTGTGGGGCTGCATCTTCCTACCC
TGAGTGTCCAGGAGGTGACAACTCTATTATCAACTGTGCTTATTCA
AACAGCGCCTCAGACTACTTCATTTGGTACAAGCAAGAATCTGGAAA
AGGTCCTCAATTCATTATAGACATTCGTTCAAATATGGACAAAAGGC
AAGGCCAAAGAGTCACCGTTTTATTGAATAAGACAGTGAAACATCTC
TCTCTGCAAATTGCAGCTACTCAACCTGGAGACTCAGCTGTCTACTT
TTGTGCAGAGGCGGGAGGAAGCCAAGGAAATCTCATCTTTGGAAAAG
GCACTAAACTCTCTGTTAAACCAAATATCCAGAACCCTGACCCTGCC
GTGTACCAGCTGAGAGACTCTAAATCCAGTGACAAGTCTGTCTGCCT
ATTCACCGATTTTGATTCTCAAACAAATGTGTCACAAAGTAAGGATT
```

-continued

```
CTGATGTGTATATCACAGACAAAACTGTGCTAGACATGAGGTCTATG

GACTTCAAGAGCAACAGTGCTGTGGCCTGGAGCAACAAATCTGACTT

TGCATGTGCAAACGCCTTCAACAACAGCATTATTCCAGAAGACACCT

TCTTCCCCAGCCCAGAAAGTTCCTGTGATGTCAAGCTGGTCGAGAAA

AGCTTTGAAACAGATACGAACCTAAACTTTCAAAACCTGTCAGTGAT

TGGGTTCCGAATCCTCCTCCTGAAAGTGGCCGGGTTTAATCTGCTCA

TGACGCTGCGGCTGTGGTCCAGCTGA
```

TCR β chain (SEQ ID NO: 16)

```
ATGGGCCCCGGGCTCCTCTGCTGGGCACTGCTTTGTCTCCTGGGAGC

AGGCTTAGTGGACGCTGGAGTCACCCAAAGTCCCACACACCTGATCA

AAACGAGAGGACAGCAAGTGACTCTGAGATGCTCTCCTAAGTCTGGG

CATGACACTGTGTCCTGGTACCAACAGGCCCTGGGTCAGGGGCCCCA

GTTTATCTTTCAGTATTATGAGGAGGAAGAGAGACAGAGAGGCAACT

TCCCTGATCGATTCTCAGGTCACCAGTTCCCTAACTATAGCTCTGAG

CTGAATGTGAACGCCTTGTTGCTGGGGGACTCGGCCCTCTATCTCTG

TGCCAGCAGCTTTTGGGGTCGTTCTCACCCTTCAAACTATGGCTACA

CCTTCGGTTCGGGGACCAGGTTAACCGTTGTAGAGGACCTGAACAAG

GTGTTCCCACCCGAGGTCGCTGTGTTTGAGCCATCAGAAGCAGAGAT

CTCCCACACCCAAAAGGCCACACTGGTGTGCCTGGCCACAGGCTTCT

TCCCTGACCACGTGGAGCTGAGCTGGTGGGTGAATGGGAAGGAGGTG

CACAGTGGGGTCAGCACGGACCCGCAGCCCCTCAAGGAGCAGCCCGC

CCTCAATGACTCCAGATACTGCCTGAGCAGCCGCCTGAGGGTCTCGG

CCACCTTCTGGCAGAACCCCGCCAACCACTTCCGCTGTCAAGTCCAG

TTCTACGGGCTCTCGGAGAATGACGAGTGGACCCAGGATAGGGCCAA

ACCCGTCACCCAGATCGTCAGCGCCGAGGCCTGGGGTAGAGCAGACT

GTGGCTTTACCTCGGTGTCCTACCAGCAAGGGGTCCTGTCTGCCACC

ATCCTCTATGAGATCCTGCTAGGGAAGGCCACCCTGTATGCTGTGCT

GGTCAGCGCCCTTGTGTTGATGGCCATGGTCAAGAGAAAGGATTTCT

GA
```

2. Amino Acid Sequence for BB (Starting From Start Codon-Coding Methionine to Stop Codon-Coding Termination (*))

TCR α chain (SEQ ID NO: 17)

MMAGIRALFMYLWLQLDWVSRGESVGLHLPTLSVQEGDNSIINCAYS
NSASDYFIWYKQESGKGPQFIIDIRSNMDKRQGQRVTVLLNKTVKHL
SLQIAATQPGDSAVYFCAEAGGSQGNLIFGKGTKLSVKPNIQNPDPA
VYQLRDSKSSDKSVCLFTDFDSQTNVSQSKDSDVYITDKTVLDMRSM
DFKSNSAVAWSNKSDFACANAFNNSIIPEDTFFPSPESSCDVKLVEK
SFETDTNLNFQNLSVIGFRILLLKVAGFNLLMTLRLWSS*

TCR β chain (SEQ ID NO: 18)

MGPGLLCWALLCLLGAGLVDAGVTQSPTHLIKTRGQQVTLRCSPKSG
HDTVSWYQQALGQGPQFIFQYYEEEERQRGNFPDRFSGHQFPNYSSE
LNVNALLLGDSALYLCASSFWGRSHPSNYGYTFGSGTRLTVVEDLNK
VFPPEVAVFEPSEAEISHTQKATLVCLATGFFPDHVELSWWVNGKEV
HSGVSTDPQPLKEQPALNDSRYCLSSRLRVSATFWQNPRNHFRCQVQ
FYGLSENDEWTQDRAKPVTQIVSAEAWGRADCGFTSVSYQQGVLSAT
ILYEILLGKATLYAVLVSALVLMAMVKRKDF*

HLA-Cw*03-Restricted NY-ESO-1$_{92-100}$-Specific T-Cell Clone "KB"

1. Nucleotide Sequence

TCR α chain (SEQ ID NO: 19)

```
ATGAACATGCTGACTGCCAGCCTGTTGAGGGCAGTCATAGCCTCCAT

CTGTGTTGTATCCAGCATGGCTCAGAAGGTAACTCAAGCGCAGACTG

AAATTTCTGTGGTGGAGAAGGAGGATGTGACCTTGGACTGTGTGTAT

GAAACCCGTGATACTACTTATTACTTATTCTGGTACAAGCAACCACC

AAGTGGAGAATTGGTTTTCCTTATTCGTCGGAACTCTTTTGATGAGC

AAAATGAAATAAGTGGTCGGTATTCTTGGAACTTCCAGAAATCCACC

AGTTCCTTCAACTTCACCATCACAGCCTCACAAGTCGTGGACTCAGC

AGTATACTTCTGTGCTCTGAGTGAGGCAAGCGGGAGAGATGACAAGA

TCATCTTTGGAAAAGGGACACGACTTCATATTCTCCCCAATATCCAG

AACCCTGACCCTGCCGTGTACCAGCTGAGAGACTCTAAATCCAGTGA

CAAGTCTGTCTGCCTATTCACCGATTTTGATTCTCAAACAAATGTGT

CACAAAGTAAGGATTCTGATGTGTATATCACAGACAAAACTGTGCTA

GACATGAGGTCTATGGACTTCAAGAGCAACAGTGCTGTGGCCTGGAG

CAACAAATCTGACTTTGCATGTGCAAACGCCTTCAACAACAGCATTA

TTCCAGAAGACACCTTCTTCCCCAGCCCAGAAAGTTCCTGTGATGTC

AAGCTGGTCGAGAAAAGCTTTGAAACAGATACGAACCTAAACTTTCA

AAACCTGTCAGTGATTGGGTTCCGAATCCTCCTCCTGAAAGTGGCCG

GGTTTAATCTGCTCATGACGCTGCGGCTGTGGTCCAGCTGA
```

TCR β chain (SEQ ID NO: 20)

```
ATGCTGCTGCTTCTGCTGCTTCTGGGGCCAGGCTCCGGGCTTGGTGC

TGTCGTCTCTCAACATCCGAGCTGGGTTATCTGTAAGAGTGGAACCT

CTGTGAAGATCGAGTGCCGTTCCCTGGACTTTCAGGCCACAACTATG

TTTTGGTATCGTCAGTTCCCGAAACAGAGTCTCATGCTGATGGCAAC

TTCCAATGAGGGCTCCAAGGCCACATACGAGCAAGGCGTCGAGAAGG

ACAAGTTTCTCATCAACCATGCAAGCCTGACCTTGTCCACTCTGACA

GTGACCAGTGCCCATCCTGAAGACAGCAGCTTCTACATCTGCAGTGC

TAGAGTCGACTTTGACCGTGACGAGCAGTTCTTCGGGCCAGGGACAC

GGCTCACCGTGCTAGAGGACCTGAAAAACGTGTTCCCACCCGAGGTC
```

```
GCTGTGTTTGAGCCATCAGAAGCAGAGATCTCCCACACCCAAAGGC

CACACTGGTGTGCCTGGCCACAGGCTTCTACCCCGACCACGTGGAGC

TGAGCTGGTGGGTGAATGGGAAGGAGGTGCACAGTGGGGTCAGCACA

GACCCGCAGCCCCTCAAGGAGCAGCCCGCCCTCAATGACTCCAGATA

CTGCCTGAGCAGCCGCCTGAGGGTCTCGGCCACCTTCTGGCAGAACC

CCCGCAACCACTTCCGCTGTCAAGTCCAGTTCTACGGGCTCTCGGAG

AATGACGAGTGGACCCAGGATAGGGCCAAACCTGTCACCCAGATCGT

CAGCGCCGAGGCCTGGGGTAGAGCAGACTGTGGCTTCACCTCCGAGT

CTTACCAGCAAGGGGTCCTGTCTGCCACCATCCTCTATGAGATCTTG

CTAGGGAAGGCCACCTTGTATGCCGTGCTGGTCAGTGCCCTCGTGCT

GATGGCCATGGTCAAGAGAAAGGATTCCAGAGGCTAG
```

2. Amino Acid Sequence for KB (Starting From Start Codon-Coding Methionine to Stop Codon-Coding Termination (*))

TCR α Chain (SEQ ID NO: 21)
```
MNMLTASLLRAVIASICVVSSMAQKVTQAQTEISVVEKEDVTLDCVY

ETRDTTYYLFWYKQPPSGELVFLIRRNSFDEQNEISGRYSWNFQKST

SSFNFTITASQVVDSAVYFCALSEASGRDDKIIFGKGTRLHILPNIQ

NPDPAVYQLRDSKSSDKSVCLFTDFDSQTNVSQSKDSDVYITDKTVL

DMRSMDFKSNSAVAWSNKSDFACANAFNNSIIPEDTFFPSPESSCDV

KLVEKSFETDTNLNFQNLSVIGFRILLLLKVAGFNLLMTLRLWSS*
```

TCR β chain (SEQ ID NO: 22)
```
MLLLLLLLGPGSGLGAVVSQHPSWVICKSGTSVKIECRSLDFQATTM

FWYRQFPKQSLMLMATSNEGSKATYEQGVEKDKFLINHASLTLSTLT

VTSAHPEDSSFYICSARVDFDRDEQFFGPGTRLTVLEDLKNVFPPEV

AVFEPSEAEISHTQKATLVCLATGFYPDHVELSWWVNGKEVHSGVST

DPQPLKEQPALNDSRYCLSSRLRVSATFWQNPRNHFRCQVQFYGLSE

NDEWTQDRAKPVTQIVSAEAWGRADCGFTSESYQQGVLSATILYEIL

LGKATLYAVLVSALVLMAMVKRKDSRG*
```

HLA-Cw*03-Restricted NY-ESO-1$_{96-104}$-Specific T-Cell Clone "ST"

1. Nucleotide Sequence

TCR α chain (SEQ ID NO: 23)
```
ATGGAAACTCTCCTGGGAGTGTCTTTGGTGATTCTATGGCTTCAACT

GGCTAGGGTGAACAGTCAACAGGGAGAAGAGGATCCTCAGGCCTTGA

GCATCCAGGAGGGTGAAAATGCCACCATGAACTGCAGTTACAAAACT

AGTATAAACAATTTACAGTGGTATAGACAAAATTCAGGTAGAGGCCT

TGTCCACCTAATTTTAATACGTTCAAATGAAAGAGAGAAACACAGTG

GAAGATTAAGAGTCACGCTTGACACTTCCAAGAAAAGCAGTTCCTTG

TTGATCACGGCTTCCCGGGCAGCAGACACTGCTTCTTACTTCTGTGC

TACGGACGCAGAGTATAACAATGCCAGACTCATGTTTGGAGATGGAA

CTCAGCTGGTGGTGAAGCCCAATATCCAGAACCCTGACCCTGCCGTG

TACCAGTTGAGAGACTCTAAATCCAGTGACAAGTCTGTCTGCCTATT

CACCGATTTTGATTCTCAAACAAATGTGTCACAAAGTAAGGATTCTG

ATGTGTATATCACAGACAAAACTGTGCTAGACATGAGGTCTATGGAC

TTCAAGAGCAACAGTGCTGTGGCCTGGAGCAACAAATCTGACTTTGC

ATGTGCAAACGCCTTCAACAACAGCATTATTCCAGAAGACACCTTCT

TCCCCAGCCCAGAAAGTTCCTGTGATGTCAAGCTGGTCGAGAAAAGC

TTTGAAACAGATACGAACCTAAACTTTCAAAACCTGTCAGTGATTGG

GTTCCGAATCCTCCTCCTGAAAGTGGCCGGGTTTAATCTGCTCATGA

CGCTGCGGCTGTGGTCCAGCTGA
```

TCR β chain (SEQ ID NO: 24)
```
ATGGGCACCAGCCTCCTCTGCTGGATGGCCCTGTGTCTCCTGGGGGC

AGATCACGCAGATACTGGAGTCTCCCAGGACCCCAGACACAAGATCA

CAAAGAGGGACAGAATGTAACTTTCAGGTGTGATCCAATTTCTGAA

CACAACCGCCTTTATTGGTACCGACAGACCCTGGGGCAGGGCCCAGA

GTTTCTGACTTACTTCCAGAATGAAGCTCAACTAGAAAAATCAAGGC

TGCTCAGTGATCGGTTCTCTGCAGAGAGGCCTAAGGGATCTTTCTCC

ACCTTGGAGATCCAGCGCACAGAGCAGGGGACTCGGCCATGTATCT

CTGTGCCAGCAGCATGGTAGCTGGGGCCAACGTCCTGACTTTCGGGG

CCGGCAGCAGGCTGACCGTGCTGGAGGACCTGAAAAACGTGTTCCCA

CCCGAGGTCGCTGTGTTTGAGCCATCAGAAGCAGAGATCTCCCACAC

CCAAAAGGCCACACTGGTGTGCCTGGCCACAGGCTTCTACCCCGACC

ACGTGGAGCTGAGCTGGTGGGTGAATGGGAAGGAGGTGCACAGTGGG

GTCAGCACAGACCCGCAGCCCCTCAAGGAGCAGCCCGCCCTCAATGA

CTCCAGATACTGCCTGAGCAGCCGCCTGAGGGTCTCGGCCACCTTCT

GGCAGAACCCCCGCAACCACTTCCGCTGTCAAGTCCAGTTCTACGGG

CTCTCGGAGAATGACGAGTGGACCCAGGATAGGGCCAAACCTGTCAC

CCAGATCGTCAGCGCCGAGGCCTGGGGTAGAGCAGACTGTGGCTTCA

CCTCCGAGTCTTACCAGCAAGGGGTCCTGTCTGCCACCATCCTCTAT

GAGATCTTGCTAGGGAAGGCCACCTTGTATGCCGTGCTGGTCAGTGC

CCTCGTGCTGATGGCCATGGTCAAGAGAAAGGATTCCAGAGGCTAG
```

2. Amino Acid Sequence for ST (Starting From Start Codon-Coding Methionine to Stop Codon-Coding Termination (*))

TCR α chain (SEQ ID NO: 25)
```
METLLGVSLVILWLQLARVNSQQGEEDPQALSIQEGENATMNCSYKT

SINNLQWYRQNSGRGLVHLILIRSNEREKHSGRLRVTLDTSKKSSSL

LITASRAADTASYFCATDAEYNNARLMFGDGTQLVVKPNIQNPDPAV

YQLRDSKSSDKSVCLFTDFDSQTNVSQSKDSDVYITDKTVLDMRSMD
```

-continued

FKSNSAVAWSNKSDFACANAFNNSIIPEDTFFPSPESSCDVKLVEKS

FETDTNLNFQNLSVIGFRILLLKVAGFNLLMTLRLWSS*

TCR β chain
(SEQ ID NO: 26)
MGTSLLCWMALCLLGADHADTGVSQDPRHKITKRGQNVTFRCDPISE

HNRLYWYRQTLGQGPEFLTYFQNEAQLEKSRLLSDRFSAERPKGSFS

TLEIQRTEQGDSAMYLCASSMVAGANVLTFGAGSRLTVLEDLKNVFP

PEVAVFEPSEAEISHTQKATLVCLATGFYPDHVELSWWVNGKEVHSG

VSTDPQPLKEQPALNDSRYCLSSRLRVSATFWQNPRNHFRCQVQFYG

LSENDEWTQDRAKPVTQIVSAEAWGRADCGFTSESYQQGVLSATILY

EILLGKATLYAVLVSALVLMAMVKRKDSRG*

HLA-A*02-Restricted NY-ESO-1$_{157-165}$-Specific T-Cell Clone "19305DP"

1. Nucleotide Sequence

TCR α chain
(SEQ ID NO: 3)
ATGGAAACTCTCCTGGGAGTGTCTTTGGTGATTCTATGGCTTCAACT

GGCTAGGGTGAACAGTCAACAGGGAGAAGAGGATCCTCAGGCCTTGA

GCATCCAGGAGGGTGAAAATGCCACCATGAACTGCAGTTACAAAACT

AGTATAAACAATTTACAGTGGTATAGACAAAATTCAGGTAGAGGCCT

TGTCCACCTAATTTTAATACGTTCAAATGAAAGAGAGAAACACAGTG

GAAGATTAAGAGTCACGCTTGACACTTCCAAGAAAAGCAGTTCCTTG

TTGATCACGGCTTCCCGGGCAGCAGACACTGCTTCTTACTTCTGTGC

TACGGACGGGGGGGCACCCTCACCTTTGGGAAGGGGACTATGCTTC

TAGTCTCTCCAGATATCCAGAACCCTGACCCTGCCGTGTACCAGCTG

AGAGACTCTAAATCCAGTGACAAGTCTGTCTGCCTATTCACCGATTT

TGATTCTCAAACAAATGTGTCACAAAGTAAGGATTCTGATGTGTATA

TCACAGACAAAACTGTGCTAGACATGAGGTCTATGGACTTCAAGAGC

AACAGTGCTGTGGCCTGGAGCAACAAATCTGACTTTGCATGTGCAAA

CGCCTTCAACAACAGCATTATTCCAGAAGACACCTTCTTCCCCAGCC

CAGAAAGTTCCTGTGATGTCAAGCTGGTCGAGAAAAGCTTTGAAACA

GATACGAACCTAAACTTTCAAAACCTGTCAGTGATTGGGTTCCGAAT

CCTCCTCCTGAAAGTGGCCGGGTTTAATCTGCTCATGACGCTGCGGC

TGTGGTCCAGCTGA

TCR β chain
(SEQ ID NO: 4)
ATGGACTCCTGGACCCTCTGCTGTGTGTCCCTTTGCATCCTGGTAGC

AAAGCACACAGATGCTGGAGTTATCCAGTCACCCCGGCACGAGGTGA

CAGAGATGGGACAAGAAGTGACTCTGAGATGTAAACCAATTTCAGGA

CACGACTACCTTTTCTGGTACAGACAGACCATGATGCGGGGACTGGA

GTTGCTCATTTACTTTAACAACAACGTTCCGATAGATGATTCAGGGA

TGCCCGAGGATCGATTCTCAGCTAAGATGCCTAATGCATCATTCTCC

ACTCTGAAGATCCAGCCCTCAGAACCCAGGGACTCAGCTGTGTACTT

-continued

CTGTGCCAGCAAGTGGGGCGGCACTGAAGCTTTCTTTGGACAAGGCA

CCAGACTCACAGTTGTAGAGGACCTGAACAAGGTGTTCCCACCCGAG

GTCGCTGTGTTTGAGCCATCAGAAGCAGAGATCTCCCACACCCAAAA

GGCCACACTGGTGTGCCTGGCCACAGGCTTCTTCCCTGACCACGTGG

AGCTGAGCTGGTGGGTGAATGGGAAGGAGGTGCACAGTGGGGTCAGC

ACGGACCCGCAGCCCCTCAAGGAGCAGCCCGCCCTCAATGACTCCAG

ATACTGCCTGAGCAGCCGCCTGAGGGTCTCGGCCACCTTCTGGCAGA

ACCCCCGCAACCACTTCCGCTGTCAAGTCCAGTTCTACGGGCTCTCG

GAGAATGACGAGTGGACCCAGGATAGGGCCAAACCCGTCACCCAGAT

CGTCAGCGCCGAGGCCTGGGGTAGAGCAGACTGTGGCTTTACCTCGG

TGTCCTACCAGCAAGGGGTCCTGTCTGCCACCATCCTCTATGAGATC

CTGCTAGGGAAGGCCACCCTGTATGCTGTGCTGGTCAGCGCCCTTGT

GTTGATGGCCATGGTCAAGAGAAAGGATTTCTGA

2. Amino Acid Sequence for 19305DP (Starting From Start Codon-Coding Methionine to Stop Codon-Coding Termination (*))

TCR α chain
(SEQ ID NO: 1)
METLLGVSLVILWLQLARVNSQQGEEDPQALSIQEGENATMNCSYKT

SINNLQWYRQNSGRGLVHLILIRSNEREKHSGRLRVTLDTSKKSSSLLI

TASRAADTASYFCATDGGGTLTFGKGTMLLVSPDIQNPDPAVYQLRDSK

SSDKSVCLFTDFDSQTNVSQSKDSDVYITDKTVLDMRSMDFKSNSAVAW

SNKSDFACANAFNNSIIPEDTFFPSPESSCDVKLVEKSFETDTNLNFQN

LSVIGFRILLLKVAGFNLLMTLRLWSS*

TCR β chain
(SEQ ID NO: 2)
MDSWTLCCVSLCILVAKHTDAGVIQSPRHEVTEMGQEVTLRCKPISGH

DYLFWYRQTMMRGLELLIYFNNNVPIDDSGMPEDRFSAKMPNASFSTLK

IQPSEPRDSAVYFCASKWGGTEAFFGQGTRLTVVEDLNKVFPPEVAVFE

PSEAEISHTQKATLVCLATGFFPDHVELSWWVNGKEVHSGVSTDPQPLK

EQPALNDSRYCLSSRLRVSATFWQNPRNHFRCQVQFYGLSENDEWTQDR

AKPVTQIVSAEAWGRADCGFTSVSYQQGVLSATILYEILLGKATLYAVL

VSALVLMAMVKRKDF*

HLA-A*02-Restricted NY-ESO-1$_{157-165}$-Specific T-Cell Clone "JD"

1. Nucleotide Sequence

TCR α chain
(SEQ ID NO: 27)
ATGATGAAATCCTTGAGAGTTTTACTAGTGATCCTGTGGCTTCAGTT

GAGCTGGGTTTGGAGCCAACAGAAGGAGGTGGAGCAGAATTCTGGACCC

CTCAGTGTTCCAGAGGGAGCCATTGCCTCTCTCAACTGCACTTACAGTG

ACCGAGGTTCCCAGTCCTTCTTCTGGTACAGACAATATTCTGGGAAAAG

CCCTGAGTTGATAATGTTCATATACTCCAATGGTGACAAAGAAGATGGA

AGGTTTACAGCACAGCTCAATAAAGCCAGCCAGTATGTTTCTCTGCTCA

TCAGAGACTCCCAGCCCAGTGATTCAGCCACCTACCTCTGTGCCGTGGG

TGCTACAAACAAGCTCATCTTTGGAACTGGCACTCTGCTTGCTGTCCAG

CCAAATATCCAGAACCCTGACCCTGCCGTGTACCAGCTGAGAGACTCTA

AATCCAGTGACAAGTCTGTCTGCCTATTCACCGATTTTGATTCTCAAAC

AAATGTGTCACAAAGTAAGGATTCTGATGTGTATATCACAGACAAAACT

GTGCTAGACATGAGGTCTATGGACTTCAAGAGCAACAGTGCTGTGGCCT

GGAGCAACAAATCTGACTTTGCATGTGCAAACGCCTTCAACAACAGCAT

TATTCCAGAAGACACCTTCTTCCCCAGCCCAGAAAGTTCCTGTGATGTC

AAGCTGGTCGAGAAAAGCTTTGAAACAGATACGAACCTAAACTTTCAAA

ACCTGTCAGTGATTGGGTTCCGAATCCTCCTCCTGAAAGTGGCCGGGTT

TAATCTGCTCATGACGCTGCGGCTGTGGTCCAGCTGA

TCR β chain
(SEQ ID NO: 28)
ATGGTTTCCAGGCTTCTCAGTTTAGTGTCCCTTTGTCTCCTGGGAGC

AAAGCACATAGAAGCTGGAGTTACTCAGTTCCCCAGCCACAGCGTAATA

GAGAAGGGCCAGACTGTGACTCTGAGATGTGACCCAATTTCTGGACATG

ATAATCTTTATTGGTATCGACGTGTTATGGGAAAAGAAATAAAATTTCT

GTTACATTTTGTGAAAGAGTCTAAACAGGATGAGTCCGGTATGCCCAAC

AATCGATTCTTAGCTGAAAGGACTGGAGGGACGTATTCTACTCTGAAGG

TGCAGCCTGCAGAACTGGAGGATTCTGGAGTTTATTTCTGTGCCAGCAG

CCAAGCGTACGGCACTGAAGCTTTCTTTGGACAAGGCACCAGACTCACA

GTTGTAGAGGACCTGAACAAGGTGTTCCCACCCGAGGTCGCTGTGTTTG

AGCCATCAGAAGCAGAGATCTCCCACACCCAAAAGGCCACACTGGTGTG

CCTGGCCACAGGCTTCTTCCCTGACCACGTGGAGCTGAGCTGGTGGGTG

AATGGGAAGGAGGTGCACAGTGGGGTCAGCACGGACCCGCAGCCCCTCA

AGGAGCAGCCCGCCCTCAATGACTCCAGATACTGCCTGAGCAGCCGCCT

GAGGGTCTCGGCCACCTTCTGGCAGAACCCCCGCAACCACTTCCGCTGT

CAAGTCCAGTTCTACGGGCTCTCGGAGAATGACGAGTGGACCCAGGATA

GGGCCAAACCCGTCACCCAGATCGTCAGCGCCGAGGCCTGGGGTAGAGC

AGACTGTGGCTTTACCTCGGTGTCCTACCAGCAAGGGGTCCTGTCTGCC

ACCATCCTCTATGAGATCCTGCTAGGGAAGGCCACCCTGTATGCTGTGC

TGGTCAGCGCCCTTGTGTTGATGGCCATGGTCAAGAGAAAGGATTTCTG

A

2. Amino Acid Sequence for JD (Starting From Start Codon-Coding Methionine to Stop Codon-Coding Termination (*))

TCR α chain
(SEQ ID NO: 29)
MMKSLRVLLVILWLQLSWVWSQQKEVEQNSGPLSVPEGAIASLNCTY

SDRGSQSFFWYRQYSGKSPELIMFIYSNGDKEDGRFTAQLNKASQYVSL

LIRDSQPSDSATYLCAVGATNKLIFGTGTLLAVQPNIQNPDPAVYQLRD

SKSSDKSVCLFTDFDSQTNVSQSKDSDVYITDKTVLDMRSMDFKSNSAV

AWSNKSDFACANAFNNSIIPEDTFFPSPESSCDVKLVEKSFETDTNLNF

QNLSVIGFRILLLKVAGFNLLMTLRLWSS*

TCR β chain
(SEQ ID NO: 30)
MVSRLLSLVSLCLLGAKHIEAGVTQFPSHSVIEKGQTVTLRCDPISGHD

NLYWYRRVIVIGKEIKELLHFVKESKQDESGMPNNRFLAERTGGTYSTL

KVQPAELEDSGVYFCASSQAYGTEAFFGQGTRLTVVEDLNKVEPPEVAV

FEPSEAEISHTQKATLVCLATGFFPDHVELSWWVNGKEVHSGVSTDPQP

LKEQPALNDSRYCLSSRLRVSATFWQNPRNHFRCQVQFYGLSENDEWTQ

DRAKPVTQIVSAEAWGRADCGFTSVSYQQGVLSATILYEILLGKATLYA

VLVSALVLMAMVKRKDF*

HLA-DRB1*07-Restricted NY-ESO-1(139-160)-Specific T-Cell Clone "PB-P"

1. Nucleotide Sequence

TCR α-chain
(SEQ ID NO: 31)
ATGGCCATGCTCCTGGGGGCATCAGTGCTGATTCTGTGGCTTCAGC

CAGACTGGGTAAACAGTCAACAGAAGAATGATGACCAGCAAGTTAAGCA

AAATTCACCATCCCTGAGCGTCCAGGAAGGAAGAATTTCTATTCTGAAC

TGTGACTATACTAACAGCATGTTTGATTATTTCCTATGGTACAAAAAAT

ACCCTGCTGAAGGTCCTACATTCCTGATATCTATAAGTTCCATTAAGGA

TAAAAATGAAGATGGAAGATTCACTGTCTTCTTAAACAAAAGTGCCAAG

CACCTCTCTGCACATTGTGCCCTCCCAGCCTGGAGACTCTGCAGTGT

ACTTCTGTGCAGCAAGCCCCTCTGGCAACACAGGCAAACTAATCTTTGG

GCAAGGGACAACTTTACAAGTAAAACCAGATATCCAGAAGCCTGACCCT

GCCGTGTACCAGCTGAGAGACTCTAAATCCAGTGACAAGTCTGTCTGCC

TATTCACCGATTTTGATTCTCAAACAAATGTGTCACAAAGTAAGGATTC

TGATGTGTATATCACAGACAAAACTGTGCTAGACATGAGGTCTATGGAC

TTCAAGAGCAACAGTGCTGTGGCCTGGAGCAACAAATCTGACTTTGCAT

GTGCAAACGCCTTCAACAACAGCATTATTCCAGAAGACACCTTCTTCCC

CAGCCCAGAAAGTTCCTGTGATGTCAAGCTGGTCGAGAAAAGCTTTGAA

ACAGATACGAACCTAAACTTTCAAAACCTGTCAGTGATTGGGTTCCGAA

TCCTCCTCCTGAAAGTGGCCGGGTTTAATCTGCTCATGACGCTGCGGCT

GTGGTCCAGCTGA

TCR β-chain
(SEQ ID NO: 32)
ATGGGCTCCAGGCTGCTCTGTTGGGTGCTGCTTTGTCTCCTGGGAGC

AGGCCCAGTAAAGGCTGGAGTCACTCAAACTCCAAGATATCTGATCAAA

ACGAGAGGACAGCAAGTGACACTGAGCTGCTCCCCTATCTCTGGGCATA

GGAGTGTATCCTGGTACCAACAGACCCCAGGACAGGGCCTTCAGTTCCT

CTTTGAATACTTCAGTGAGACACAGAGAAACAAAGGAAACTTCCCTGGT

CGATTCTCAGGGCGCCAGTTCTCTAACTCTCGCTCTGAGATGAATGTGA

GCACCTTGGAGCTGGGGGACTCGGCCCTTTATCTTTGCGCCAGCAGCCC

AGACAGGGCCATGAACACTGAAGCTTCTTTGGACAAGGCACCAGACTC

```
ACAGTTGTAGAGGACCTGAACAAGGTGTTCCCACCCGAGGTCGCTGTGT

TTGAGCCATCAGAAGCAGAGATCTCCCACACCCAAAAGGCCACACTGGT

GTGCCTGGCCACAGGCTTCTTCCCTGACCACGTGGAGCTGAGCTGGTGG

GTGAATGGGAAGGAGGTGCACAGTGGGGTCAGCACGGACCCGCAGCCCC

TCAAGGAGCAGCCCGCCCTCAATGACTCCAGATACTGCCTGAGCAGCCG

CCTGAGGGTCTCGGCCACCTTCTGGCAGAACCCCCGCAACCACTTCCGC

TGTCAAGTCCAGTTCTACGGGCTCTCGGAGAATGACGAGTGGACCCAGG

ATAGGGCCAAACCCGTCACCCAGATCGTCAGCGCCGAGGCCTGGGGTAG

AGCAGACTGTGGCTTTACCTCGGTGTCCTACCAGCAAGGGGTCCTGTCT

GCCACCATCCTCTATGAGATCCTGCTAGGGAAGGCCACCCTGTATGCTG

TGCTGGTCAGCGCCCTTGTGTTGATGGCCATGGTCAAGAGAAAGGATTT

CTGA
```

2. Amino Acid Sequence for PB-P (Starting From Start Codon-Coding Methionine to Stop Codon-Coding Termination (*))

```
TCR α-chain
                                        (SEQ ID NO: 33)
MAMLLGASVLILWLQPDWVNSQQKNDDQQVKQNSPSLSVQEGRISIL

NCDYTNSMFDYFLWYKKYPAEGPTFLISISSIKDKNEDGRFTVFLNKSA

KHLSLHIVPSQPGDSAVYFCAASPSGNTGKLIFGQGTTLQVKPDIQKPD

PAVYQLRDSKSSDKSVCLFTDFDSQTNVSQSKDSDVYITDKTVLDMRSM

DFKSNSAVAWSNKSDFACANAFNNSIIPEDTFFPSPESSCDVKLVEKSF

ETDTNLNFQNLSVIGFRILLLKVAGFNLLMTLRLWSS*

TCR β-chain
                                        (SEQ ID NO: 34)
MGSRLLCWVLLCLLGAGPVKAGVTQTPRYLIKTRGQQVTLSCSPISGH

RSVSWYQQTPGQGLQFLFEYFSETQRNKGNFPGRFSGRQFSNSRSEMNV

STLELGDSALYLCASSPDRAMNTEAFFGQGTRLTVVEDLNKVFPPEVAV

FEPSEAEISHTQKATLVCLATGFFPDHVELSWWVNGKEVHSGVSTDPQP

LKEQPALNDSRYCLSSRLRVSATFWQNPRNHFRCQVQFYGLSENDEWTQ

DRAKPVTQIVSAEAWGRADCGFTSVSYQQGVLSATILYEILLGKATLYA

VLVSALVLMAMVKRKDF*
```

HLA-DRB1*04-Restricted NY-ESO-1(111-143)-Specific T-Cell Clone "PB-T"

1. Nucleotide Sequence

```
TCR α-chain
                                        (SEQ ID NO: 35)
ATGGCCTCTGCACCCATCTCGATGCTTGCGATGCTCTTCACATTGAG

TGGGCTGAGAGCTCAGTCAGTGGCTCAGCCGGAAGATCAGGTCAACGTTG

CTGAAGGGAATCCTCTGACTGTGAAATGCACCTATTCAGTCTCTGGAAAC

CCTTATCTTTTTTGGTATGTTCAATACCCCAACCGAGGCCTCCAGTTCCT

TCTGAAATACATCACAGGGGATAACCTGGTTAAAGGCAGCTATGGCTTTG

AAGCTGAATTTAACAAGAGCCAAACCTCCTTCCACCTGAAGAAACCATCT

GCCCTTGTGAGCGACTCCGCTTTGTACTTCTGTGCTGTGAGAGACAGGGA

GAGAGATGACAAGATCATCTTTGGAAAAGGGACACGACTTCATATTCTCC

CCAATATCCAGAAGCCTGACCCTGCCGTGTACCAGCTGAGAGACTCTAAA

TCCAGTGACAAGTCTGTCTGCCTATTCACCGATTTTGATTCTCAAACAAA

TGTGTCACAAAGTAAGGATTCTGATGTGTATATCACAGACAAAACTGTGC

TAGACATGAGGTCTATGGACTTCAAGAGCAACAGTGCTGTGGCCTGGAGC

AACAAATCTGACTTTGCATGTGCAAACGCCTTCAACAACAGCATTATTCC

AGAAGACACCTTCTTCCCCAGCCCAGAAAGTTCCTGTGATGTCAAGCTGG

TCGAGAAAAGCTTTGAAACAGATACGAACCTAAACTTTCAAAACCTGTCA

GTGATTGGGTTCCGAATCCTCCTCCTGAAAGTGGCCGGGTTTAATCTGCT

CATGACGCTGCGGCTGTGGTCCAGCTGA

TCR β-chain
                                        (SEQ ID NO: 36)
ATGGATACCTGGCTCGTATGCTGGGCAATTTTTAGTCTCTTGAAAG

CAGGACTCACAGAACCTGAAGTCACCCAGACTCCCAGCCATCAGGTCACA

CAGATGGGACAGGAAGTGATCTTGCGCTGTGTCCCCATCTCTAATCACTT

ATACTTCTATTGGTACAGACAAATCTTGGGGCAGAAAGTCGAGTTTCTGG

TTTCCTTTTATAATAATGAAATCTCAGAGAAGTCTGAAATATTCGATGAT

CAATTCTCAGTTGAAAGGCCTGATGGATCAAATTTCACTCTGAAGATCCG

GTCCACAAAGCTGGAGGACTCAGCCATGTACTTCTGTGCCAGCAGAGCGG

AGATCACAGATACGCAGTATTTTGGCCCAGGCACCCGGCTGACAGTGCTC

GAGGACCTGAAAAACGTGTTCCCACCCGAGGTCGCTGTGTTTGAGCCATC

AGAAGCAGAGATCTCCCACACCCAAAAGGCCACACTGGTGTGCCTGGCCA

CAGGCTTCTACCCCGACCACGTGGAGCTGAGCTGGTGGGTGAATGGGAAG

GAGGTGCACAGTGGGGTCAGCACAGACCCGCAGCCCCTCAAGGAGCAGCC

CGCCCTCAATGACTCCAGATACTGCCTGAGCAGCCGCCTGAGGGTCTCGG

CCACCTTCTGGCAGAACCCCCGCAACCACTTCCGCTGTCAAGTCCAGTTC

TACGGGCTCTCGGAGAATGACGAGTGGACCCAGGATAGGGCCAAACCTGT

CACCCAGATCGTCAGCGCCGAGGCCTGGGGTAGAGCAGACTGTGGCTTCA

CCTCCGAGTCTTACCAGCAAGGGGTCCTGTCTGCCACCATCCTCTATGAG

ATCTTGCTAGGGAAGGCCACCTTGTATGCCGTGCTGGTCAGTGCCCTCGT

GCTGATGGCCATGGTCAAGAGAAAGGATTCCAGAGGCTAG
```

2. Amino Acid Sequence for PB-T (Starting From Start Codon-Coding Methionine to Stop Codon-Coding Termination (*))

```
TCR α-chain
                                        (SEQ ID NO: 37)
MASAPISMLAMLFTLSGLRAQSVAQPEDQVNVAEGNPLTVKCTYSVS

GNPYLFWYVQYPNRGLQFLLKYITGDNLVKGSYGFEAEFNKSQTSFHLKK

PSALVSDSALYFCAVRDRERDDKIIFGKGTRLHILPNIQKPDPAVYQLRD

SKSSDKSVCLFTDFDSQTNVSQSKDSDVYITDKTVLDMRSMDFKSNSAVA

WSNKSDFACANAFNNSIIPEDTFFPSPESSCDVKLVEKSFETDTNLNFQN

LSVIGFRILLLKVAGFNLLMTLRLWSS*
```

-continued

TCR β-chain
(SEQ ID NO: 38)
MDTWLVCWAIFSLLKAGLTEPEVTQTPSHQVTQMGQEVILRCVPISNH

LYFYWYRQILGQKVEFLVSFYNNEISEKSEIFDDQFSVERPDGSNFTLKI

RSTKLEDSAMYFCASRAEITDTQYFGPGTRLTVLEDLKNVFPPEVAVFEP

SEAEISHTQKATLVCLATGFYPDHVELSWWVNGKEVHSGVSTDPQPLKEQ

PALNDSRYCLSSRLRVSATFWQNPRNHFRCQVQFYGLSENDEWTQDRAKP

VTQIVSAEAWGRADCGFTSESYQQGVLSATILYEILLGKATLYAVLVSAL

VLMAMVKRKDSRG*

HLA-DRB1*07-Restricted NY-ESO-1(139-160)-Specific T-Cell Clone "PB13.2"

1. Nucleotide Sequence

TCR α-chain
(SEQ ID NO: 39)
ATGGCCATGCTCCTGGGGGCATCAGTGCTGATTCTGTGGCTTCAGC

CAGACTGGGTAAACAGTCAACAGAAGAATGATGACCAGCAAGTTAAGCAA

AATTCACCATCCCTGAGCGTCCAGGAAGGAAGAATTTCTATTCTGAACTG

TGACTATACTAACAGCATGTTTGATTATTTCCTATGGTACAAAAAATACC

CTGCTGAAGGTCCTACATTCCTGATATCTATAAGTTCCATTAAGGATAAA

AATGAAGATGGAAGATTCACTGTCTTCTTAAACAAAAGTGCCAAGCACCT

CTCTCTGCACATTGTGCCCTCCCAGCCTGGAGACTCTGCAGTGTACTTCT

GTGCAGCAAGCGCGATAGGAGGTGCTGACGGACTCACCTTTGGCAAAGGG

ACTCATCTAATCATCCAGCCCTATATCCAGAACCCTGACCCTGCCGTGTA

CCAGCTGAGAGACTCTAAATCCAGTGACAAGTCTGTCTGCCTATTCACCG

ATTTTGATTCTCAAACAATGTGTCACAAAGTAAGGATTCTGATGTGTAT

ATCACAGACAAAACTGTGCTAGACATGAGGTCTATGGACTTCAAGAGCAA

CAGTGCTGTGGCCTGGAGCAACAAATCTGACTTTGCATGTGCAAACGCCT

TCAACAACAGCATTATTCCAGAAGACACCTTCTTCCCCAGCCCAGAAAGT

TCCTGTGATGTCAAGCTGGTCGAGAAAAGCTTTGAAACAGATACGAACCT

AAACTTTCAAAACCTGTCAGTGATTGGGTTCCGAATCCTCCTCCTGAAAG

TGGCCGGGTTTAATCTGCTCATGACGCTGCGGCTGTGGTCCAGCTGA

TCR β-chain
(SEQ ID NO: 40)
ATGAGCCTCGGGCTCCTGTGCTGTGGGCCTTTTCTCTCCTGTGGC

AGGTCCAGTGAATGCTGGTGTCACTCAGACCCCAAAATTCCGGGTCCTGA

AGACAGGACAGAGCATGACACTGCTGTGTGCCCAGGATATGAACCATGAA

TACATGTACTGGTATCGACAAGACCCAGGCATGGGGCTGAGGCTGATTCA

TTACTCAGTTGGTGAGGGTACAACTGCCAAAGGAGAGGTCCCTGATGGCT

ACAATGTCTCCAGATTAAAAAAACAGAATTTCCTGCTGGGGTTGGAGTCG

GCTGCTCCCTCCCAAACATCTGTGTACTTCTGTGCCAGCAGTATTCGGGG

AAAAAGGTACAATGAGCAGTTCTTCGGGCCAGGGACACGGCTCACCGTGC

TAGAGGACCTGAAAAACGTGTTCCCACCCGAGGTCGCTGTGTTTGAGCCA

TCAGAAGCAGAGATCTCCCACACCCAAAAGGCCACACTGGTGTGCCTGGC

CACAGGCTTCTACCCCGACCACGTGGAGCTGAGCTGGTGGGTGAATGGGA

AGGAGGTGCACAGTGGGGTCAGCACAGACCCGCAGCCCCTCAAGGAGCAG

CCCGCCCTCAATGACTCCAGATACTGCCTGAGCAGCCGCCTGAGGGTCTC

GGCCACCTTCTGGCAGAACCCCCGCAACCACTTCCGCTGTCAAGTCCAGT

TCTACGGGCTCTCGGAGAATGACGAGTGGACCCAGGATAGGGCCAAACCT

GTCACCCAGATCGTCAGCGCCGAGGCCTGGGGTAGAGCAGACTGTGGCTT

CACCTCCGAGTCTTACCAGCAAGGGGTCCTGTCTGCCACCATCCTCTATG

AGATCTTGCTAGGGAAGGCCACCTTGTATGCCGTGCTGGTCAGTGCCCTC

GTGCTGATGGCCATGGTCAAGAGAAAGGATTCCAGAGGCTAG

2. Amino Acid Sequence For PB 13.2 (Starting From Start Codon-Coding Methionine to Stop Codon-Coding Termination (*))

TCR α-chain
(SEQ ID NO: 41)
MAMLLGASVLILWLQPDWVNSQQKNDDQQVKQNSPSLSVQEGRISIL

NCDYTNSMFDYFLWYKKYPAEGPTFLISISSIKDKNEDGRFTVFLNKSAK

HLSLHIVPSQPGDSAVYFCAASAIGGADGLTFGKGTHLIIQPYIQNPDPA

VYQLRDSKSSDKSVCLFTDFDSQTNVSQSKDSDVYITDKTVLDMRSMDFK

SNSAVAWSNKSDFACANAFNNSIIPEDTFFPSPESSCDVKLVEKSFETDT

NLNFQNLSVIGFRILLLKVAGFNLLMTLRLWSS*

TCR β-chain
(SEQ ID NO: 42)
MSLGLLCCGAFSLLWAGPVNAGVTQTPKFRVLKTGQSMTLLCAQDM

NHEYMYWYRQDPGMGLRLIHYSVGEGTTAKGEVPDGYNVSRLKKQNFLLG

LESAAPSQTSVYFCASSIRGKRYNEQFFGPGTRLTVLEDLKNVFPPEVAV

FEPSEAEISHTQKATLVCLATGFYPDHVELSWWVNGKEVHSGVSTDPQPL

KEQPALNDSRYCLSSRLRVSATFWQNPRNHFRCQVQFYGLSENDEWTQDR

AKPVTQIVSAEAWGRADCGFTSESYQQGVLSATILYEILLGKATLYAVLV

SALVLMAMVKRKDSRG*

In connection with the foregoing sequences of this Example, this Example provides a non-limiting demonstration of generating a NY-ESO-1-specific TCR-expressing retroviral vector (FIG. 1). These figures illustrate the following:

FIG. 1A. For transduction of T cells, murine stem cell virus (MSCV)-derived vectors have been widely used because of strong promoter activity by MSCV long terminal repeats (LTR) and in vivo stability of transgene expression in hematopoietic cells. As 3'-LTR is copied to 5'-LTR during integration to host cells such as T cells and responsible for the transcription of transgenes, 3'-LTR in the plasmids is important in the expression. On the other hand, 5'-LTR is responsible for the transcription for virus production. Schematic representation for classical MSCV-derived vectors (pMIG-II and pMIG-w) is shown in FIG. 1. Both vectors have MSCV-derived LTR at 5' and 3' sites, packaging signal (w), multiple cloning sites (MCS). Transgene is cloned in the MCS, which is followed by the internal ribosomal entry site (IRES) and the green fluorescent protein gene (GFP) to efficiently detect transduced cells. pMIG-w vector has additional woodchuck hepatitis virus post-transcriptional regulatory element (WRE), which enhances expression of the transgene. In recent retrovirus vectors, further modifications are introduced as found in the commercial retroviral vector, pDON-5 (Clontech). pDON-5, which is derived from a murine leukemia virus (MLV) vector, replaces the 5'-LTR with the CMV/MLV hybrid LTR for enhanced virus production through strong CMV promoter activity in virus packaging cell lines. Furthermore, the partial intron from the human elongation factor 1 alpha gene is introduced to provide a splice acceptor site (SA), which together with an endogenous splice donor site (SD) induces splicing and enhances expression.

FIG. 1B. To create a retrovirus vector which can produce high-titer retrovirus that induces high level transgene (TCR) expression in T cells, we amplified a DNA fragment from 5'-LTR to the intron containing a splice acceptor site in the pDON-5 plasmid. The forward primer was designed to append SgrAI restriction enzyme recognition site before 5'-LTR and the reverse primer was designed to append NotI and SalI sites after the intron. PCR-amplified fragment was treated with SgrAI and SalI and inserted into pMIG-II and pMIG-w plasmids so that 5'-LTR to GFP is replaced.

FIG. 1C. The plasmids depicted in FIG. 1C only have NotI and SalI recognition sites for cloning. The use of SalI which recognizes a specific 6-mer nucleotide sequence is not preferable because it may appear frequently enough to be present in the transgene, thus resulting in its cleavage. To provide additional restriction enzyme recognition sites which are believed to be unlikely to appear in most TCR transgenes, we amplified a 1.8 kb DNA fragment (stuffer) with the forward primer with a NotI restriction site, and the reverse primer with PacI-SalI sites. The amplified fragment was treated with NotI and SalI restriction enzymes and inserted into the new plasmids.

FIG. 1D. The depicted TCR expression cassette was amplified with the forward primer with the NotI restriction site and the reverse primer with the PacI restriction enzyme site. The amplified expression cassette was treated with NotI and PacI restriction enzymes and inserted into the new plasmids.

Transduction of 19305DP-TCR gene into polyclonally activated T cells (FIG. 2). T cells from healthy individuals were preactivated for 2 days using phytohemaglutinin (PHA, obtained from Remel) in the presence of low-dose IL-2, IL-7, and IL-12. Retroviral particles were coated on non-tissue culture plate that were pre-coated with Retronectin (obtained from Clontech) and blocked with bovine serum albumin (BSA from Sigma). Activated T cells were infected by retrovirus by culturing on retrovirus-coated plate. Viral infection was repeated 24 hours later. Total number of infection was 2 times. Infected cells were expanded in the presence of IL-2 and IL-7. IL-12 was included for 5 days from the activation of T cells with PHA. After infection, more than 95% TCR gene-transduced T cells expressed transduced TCR by staining with TCR Vβ subtype-specific antibody.

Anti-tumor function of 19305DP-TCR-transduced T cells (FIGS. 3 and 8-10). TCR gene-transduced T cells were co-cultured with HLA-A*02+NY-ESO-1+ melanoma cell line, SK-MEL-37 or HLA-A*02+NY-ESO-1-melanoma cell line, SK-MEL-29 for 6 hours in the presence of Golgi Stop (BD Biosciences). Cells were stained by fluorochrome-conjugated anti-CD4 and anti-CD8 antibodies and fixed and permeabilized using BD Cytofix/Cytoperm Kit (BD Biosciences). Intracellular IFN-γ was stained by fluorochrome-conjugated anti-IFN-γ antibody. Both TCR gene-transduced CD4+ and CD8+ T cells produced IFN-γ only when they were co-cultured with NY-ESO-1+ SK-MEL-37 but not SK-MEL-29. Untransduced CD4+ and CD8+ T cells did not produce IFN-γ against SK-MEL-37 or SK-MEL-29 (FIG. 3). In FIG. 8, immuno-deficient NOD/SCID/IL-2Rγ-chain-deficient (NSG) mice were inoculated with 1 million SK-MEL-37. After the tumor growth was confirmed on day 9, 10 million 19305DP-TCR gene-transduced T cells were injected. Control tumor-bearing mice were injected with irrelevant TCR-transduced T cells. Mice treated with 19305DP-TCR-transduced T cells showed significant delay in tumor growth and most mice eventually reject tumor xenograft. Tumor was continuously grew in control mice received irrelevant TCR-transduced T cells.

EXAMPLE 2

This Example provides a description of additional TCR sequences that can be included with any one of the TCR sequences described in Example 1 in libraries of this disclosure. These TCRs impart the capability to CD4+ T cells to directly recognize NY-ESO-1/LAGE-1 positive cancer cells.

"JM" HLA-DPB1*0401/0402-Restricted NY-ESO-$1_{157-170}$-Specific Tumor-Recognizing CD4$^+$ T Cell Clone (a) cDNA Nucleotide Sequences of TCR α and β Chains

```
TCR α chain
                                       (SEQ ID NO: 47)
ATGAAGTTGGTGACAAGCATTACTGTACTCCTATCTTTGGGTATTA

TGGGTGATGCTAAGACCACACAGCCAAATTCAATGGAGAGTAACGAAGAA

GAGCCTGTTCACTTGCCTTGTAACCACTCCACAATCAGTGGAACTGATTA

CATTGGTATCGACAGCTTCCCTCCCAGGGTCCAGAGTACGTGATTCATGG

CATATCTTACAAGCAATGTGAACAACAGAATGGCCTCTCTGGCAATCGCT

GAAGACAGAAAGTCCAGTACCTTGATCCTGCACCGTGCTACCTTGAGAGA

TGCTGCTGTGTACTACTGCATCCCTAATAACAATGACATGCGCTTTGGAG

CAGGGACCAGACTGACAGTAAAACCAAATATCCAGAACCCTGACCCTGCC

GTGTACCAGCTGAGAGACTCTAAATCCAGTGACAAGTCTGTCTGCCTATT

CACCGATTTTGATTCTCAAACAAATGTGTCACAAAGTAAGGATTCTGATG

TGTATATCACAGACAAAACTGTGCTAGACATGAGGTCTATGGACTTCAAG

AGCAACAGTGCTGTGGCCTGGAGCAACAAATCTGACTTTGCATGTGCAAA

CGCCTTCAACAACAGCATTATTCCAGAAGACACCTTCTTCCCCAGCCCAG

AAAGTTCCTGTGATGTCAAGCTGGTCGAGAAAAGCTTTGAAACAGATACG

AACCTAAACTTTCAAAACCTGTCAGTGATTGGGTTCCGAATCCTCCTCCT

GAAAGTGGCCGGGTTTAATCTGCTCATGACGCTGCGGCTGTGGTCCAGCT

GA

TCR β chain
                                       (SEQ ID NO: 48)
ATGGGCTCCAGGCTGCTCTGTTGGGTGCTGCTTTGTCTCCTGGGAG

CAGGCCCAGTAAAGGCTGGAGTCACTCAAACTCCAAGATATCTGATCAAA

ACGAGAGGACAGCAAGTGACACTGAGCTGCTCCCCTATCTCTGGGCATAG

GAGTGTATCCTGGTACCAACAGACCCCAGGACAGGGCCTTCAGTTCCTCT

TTGAATACTTCAGTGAGACACAGAGAAACAAAGGAAACTTCCCTGGTCGA
```

-continued
```
TTCTCAGGGCGCCAGTTCTCTAACTCTCGCTCTGAGATGAATGTGAGCAC

CTTGGAGCTGGGGGACTCGGCCCTTTATCTTTGCGCCAGCAGCTTCCCCA

GGGAACCTAACTATGGCTACACCTTCGGTTCGGGGACCAGGTTAACCGTT

GTAGAGGACCTGAACAAGGTGTTCCCACCCGAGGTCGCTGTGTTTGAGCC

ATCAGAAGCAGAGATCTCCCACACCCAAAAGGCCACACTGGTGTGCCTGG

CCACAGGCTTCTTCCCTGACCACGTGGAGCTGAGCTGGTGGGTGAATGGG

AAGGAGGTGCACAGTGGGGTCAGCACGGACCCGCAGCCCCTCAAGGAGCA

GCCCGCCCTCAATGACTCCAGATACTGCCTGAGCAGCCGCCTGAGGGTCT

CGGCCACCTTCTGGCAGAACCCCCGCAACCACTTCCGCTGTCAAGTCCAG

TTCTACGGGCTCTCGGAGAATGACGAGTGGACCCAGGATAGGGCCAAACC

CGTCACCCAGATCGTCAGCGCCGAGGCCTGGGGTAGAGCAGACTGTGGCT

TTACCTCGGTGTCCTACCAGCAAGGGGTCCTGTCTGCCACCATCCTCTAT

GAGATCCTGCTAGGGAAGGCCACCCTGTATGCTGTGCTGGTCAGCGCCCT

TGTGTTGATGGCCATGGTCAAGAGAAAGGATTTCTGA
```

(b) Amino Acid Sequences of TCR α and β Chains For JM (TCR Variable Regions are in Italic, CDR3 Regions are in Bold)

TCR α chain
(SEQ ID NO: 49)
*MKLVTSITVLLSLGIMGDAKTTQPNSMESNEEEPVHLPCNHSTISGTDYIHW*

*YRQLPSQGPEYVIHGLTSNVNNRAIASLAIAEDRKSSTLIIKRATLRDAAVYY*CIPNNNDMR

F*GAGTRLTVKPNIQNPDPAVYQLRDSKSSDKSVCLFTDFDSQTNVSQSKDSDVYITDK*

TVLDMRSMDFKSNSAVAWSNKSDFACANAFNNSIIPEDTFFPSPESSCDVKLVEKSFE

TDTNLNFQNLSVIGFRILLLKVAGFNLLMTLRLWSS

TCR β chain
(SEQ ID NO: 50)
*MGSRLLCWVLLCLLGAGPVKAGVTQTPRYLIKTRGQQVTLSCSPISGHRSV*

*SWYQQTPGQGLQFLFEYFSETQRNKGNFPGRFSGRQFSNSRSEMNYSTLELGDSALYL*CA

SSFPREPNYGYTF*GSGTRLTVV*EDLNKVFPPEVAVFEPSEAEISHTQKATLVCLATGFF

PDHVELSWWVNGKEVHSGVSTDPQPLKEQPALNDSRYCLSSRLRVSATFWQNPRNH

FRCQVQFYGLSENDEWTQDRAKPVTQIVSAEAWGRADCGFTSVSYQQGVLSATILY

EILLGKATLYAVLVSALVLMAMVKRKDF

"5B8" HLA-DPB1*0401/0402-restricted NY-ESO-1₁₅₇₋₁₇₀-Specific Tumor-Recognizing CD4⁺ T Cell Clone
(a) cDNA Nucleotide Sequences of TCR α and β Chains TCR α chain
(SEQ ID NO: 51)
```
ATGGCCCAGACAGTCACTCAGTCTCAACCAGAGATGTCTGTGCAGG

AGGCAGAGACTGTGACCCTGAGTTGCACATATGACACCAGTGAGAATAAT

TATTATTTGTTCTGGTACAAGCAGCCTCCCAGCAGGCAGATGATTCTCGT

TATTCGCCAAGAAGCTTATAAGCAACAGAATGCAACGGAGAATCGTTTCT

CTGTGAACTTCCAGAAAGCAGCCAATCCTTCAGTCTCAAGATCTCAGAC

TCACAGCTGGGGGACACTGCGATGTATTTCTGTGCTTTCTCGAGAGGGAG
```

-continued
```
TGGAGGTAGCAACTATAAACTGACATTTGGAAAAGGAACTCTCTTAACCG

TGAATCCAAATATCCAGAACCCTGACCCTGCCGTGTACCAGCTGAGAGAC

TCTAAATCCAGTGACAAGTCTGTCTGCCTATTCACCGATTTTGATTCTCA

AACAAATGTGTCACAAAGTAAGGATTCTGATGTGTATATCACAGACAAAA

CTGTGCTAGACATGAGGTCTATGGACTTCAAGAGCAACAGTGCTGTGGCC

TGGAGCAACAAATCTGACTTTGCATGTGCAAACGCCTTCAACAACAGCAT

TATTCCAGAAGACACCTTCTTCCCCAGCCCAGAAAGTTCCTGTGATGTCA

AGCTGGTCGAGAAAAGCTTTGAAACAGATACGAACCTAAACTTTCAAAAC

CTGTCAGTGATTGGGTTCCGAATCCTCCTCCTGAAAGTGGCCGGGTTTAA

TCTGCTCATGACGCTGCGGCTGTGGTCCAGCTGA
```

TCR β chain
(SEQ ID NO: 52)
```
ATGGGCACCAGGCTCCTCTTCTGGGTGGCCTTCTGTCTCCTGGGGG

CAGATCACACAGGAGCTGGAGTCTCCCAGTCCCCCAGTAACAAGGTCACA

GAGAAGGGAAAGGATGTAGAGCTCAGGTGTGATCCAATTTCAGGTCATAC

TGCCCTTTACTGGTACCGACAGAGCCTGGGGCAGGGCCTGGAGTTTTTAA

TTTACTTCCAAGGCAACAGTGCACCAGACAAATCAGGGCTGCCCAGTGAT

CGCTTCTCTGCAGAGAGGACTGGGGGATCCGTCTCCACTCTGACGATCCA

GCGCACACAGCAGGAGGACTCGGCCGTGTATCTCTGTGCCAGCAGCTTAG

TCCCCGACAGTGCCTACGAGCAGTACTTCGGGCCGGGCACCAGGCTCACG

GTCACAGAGGACCTGAAAAACGTGTTCCCACCCGAGGTCGCTGTGTTTGA

GCCATCAGAAGCAGAGATCTCCCACACCCAAAAGGCCACACTGGTATGCC

TGGCCACAGGCTTCTACCCCGACCACGTGGAGCTGAGCTGGTGGGTGAAT

GGGAAGGAGGTGCACAGTGGGGTCAGCACGGACCCGCAGCCCCTCAAGGA

GCAGCCCGCCCTCAATGACTCCAGATACTGCCTGAGCAGCCGCCTGAGGG

TCTCGGCCACCTTCTGGCAGAACCCCCGCAACCACTTCCGCTGTCAAGTC
```

```
CAGTTCTACGGGCTCTCGGAGAATGACGAGTGGACCCAGGATAGGGCCAA

ACCTGTCACCCAGATCGTCAGCGCCGAGGCCTGGGGTAGAGCAGACTGTG

GCTTCACCTCCGAGTCTTACCAGCAAGGGGTCCTGTCTGCCACCATCCTC

TATGAGATCTTGCTAGGGAAGGCCACCTTGTATGCCGTGCTGGTCAGTGC

CCTCGTGCTGATGGCCATGGTCAAGAGAAAGGATTCCAGAGGCTAG
```

(b) Amino Acid Sequences of TCR α and β Chains for 5B8 (TCR Variable Regions are in Italic, CDR3 Regions are in Bold)

```
TCR α chain
                                             SEQ ID NO: 53)
MAQTVTQSQPEMSVQEAETVTLSCTYDTSENNYYLFWYKQPPSRQMILVIR

QEAYKQQNATENRFSVNFQKAAKSFSLKISDSQLGDTAMYFCAFSRGSGGSNYKLTFGK

GTLLTVNPNIQNPDPAVYQLRDSKSSDKSVCLFTDFDSQTNVSQSKDSDVYITDKTVL

DMRSMDFKSNSAVAWSNKSDFACANAFNNSIIPEDTFFPSPESSCDVKLVEKSFETDT

NLNFQNLSVIGFRILLLKVAGFNLLMTLRLWSS

TCR β chain
                                             SEQ ID NO: 54)
MGTRLLFWVAFCLLGADHTGAGVSQSPSNKVTEKGKDVELRCDPISGHTA

LYWYRQSLGQGLEFLIYFQGNSAPDKSGLPSDRFSAERTGGSVSTLTIQRTQQEDSAVYLC

ASSLVPDSAYEQYFGPGTRLTVTEDLKNVFPPEVAVFEPSEAEISHTQKATLVCLATGF

YPDHVELSWWVNGKEVHSGVSTDPQPLKEQPALNDSRYCLSSRLRVSATFWQNPRN

HFRCQVQFYGLSENDEWTQDRAKPVTQIVSAEAWGRADCGFTSESYQQGVLSATIL

YEILLGKATLYAVLVSALVLMAMVKRKDSRG
```

"SB95" HLA-DRB1*0101-Restricted NY-ESO-1$_{95-106}$-Specific Tumor-Recognizing CD4$^+$ T Cell Clone (a) cDNA Nucleotide Sequences of TCR α and β Chains

```
TCR alpha
                                             SEQ ID NO: 55)
ATGCTCCTGCTGCTCGTCCCAGTGCTCGAGGTGATTTTTACCCTGGG

AGGAACCAGAGCCCAGTCGGTGACCCAGCTTGGCAGCCACGTCTCTGTCT

CTGAGGGAGCCCTGGTTCTGCTGAGGTGCAACTACTCATCGTCTGTTCCA

CCATATCTCTTCTGGTATGTGCAATACCCCAACCAAGGACTCCAGCTTCT

CCTGAAGCACACAACAGGGGCCACCCTGGTTAAAGGCATCAACGGTTTTG

AGGCTGAATTTAAGAAGAGTGAAACCTCCTTCCACCTGACGAAACCCTCA

GCCCATATGAGCGACGCGGCTGAGTACTTCTGTGCTGTGAGTGATTCTAG

GGCTGCAGGCAACAAGCTAACTTTTGGAGGAGGAACCAGGGTGCTAGTTA

AACCAAATATCCAGAACCCTGACCCTGCCGTGTACCAGCTGAGAGACTCT

AAATCCAGTGACAAGTCTGTCTGCCTATTCACCGATTTTGATTCTCAAAC

AAATGTGTCACAAAGTAAGGATTCTGATGTGTATATCACAGACAAAACTG

TGCTAGACATGAGGTCTATGGACTTCAAGAGCAACAGTGCTGTGGCCTGG

AGCAACAAATCTGACTTTGCATGTGCAAACGCCTTCAACAACAGCATTAT

TCCAGAAGACACCTTCTTCCCCAGCCCAGAAAGTTCCTGTGATGTCAAGC

TGGTCGAGAAAAGCTTTGAAACAGATACGAACCTAAACTTTCAAAACCTG

TCAGTGATTGGGTTCCGAATCCTCCTCCTGAAAGTGGCCGGGTTTAATCT

GCTCATGACGCTGCGGCTGTGGTCCAGCTGA

TCR beta
                                             SEQ ID NO: 56)
ATGGGAATCAGGCTCCTCTGTCGTGTGGCCTTTTGTTTCCTGGCTGT

AGGCCTCGTAGATGTGAAAGTAACCCAGAGCTCGAGATATCTAGTCAAAA

GGACGGGAGAGAAAGTTTTTCTGGAATGTGTCCAGGATATGGACCATGAA

AATATGTTCTGGTATCGACAAGACCCAGGTCTGGGGCTACGGCTGATCTA

TTTCTCATATGATGTTAAAATGAAAGAAAAAGGAGATATTCCTGAGGGGT

ACAGTGTCTCTAGAGAAGAAGGAGCGCTTCTCCCTGATTCTGGAGTCC

GCCAGCACCAACCAGACATCTATGTACCTCTGTGCCAGCAGATTCCCCGG

GACAGCCTATAATTCACCCCTCCACTTTGGGAATGGGACCAGGCTCACTG

TGACAGAGGACCTGAACAAGGTGTTCCCACCCGAGGTCGCTGTGTTTGAG

CCATCAGAAGCAGAGATCTCCCACACCCAAAAGGCCACACTGGTGTGCCT

GGCCACAGGCTTCTTCCCTGACCACGTGGAGCTGAGCTGGTGGGTGAATG

GGAAGGAGGTGCACAGTGGGGTCAGCACGGACCCGCAGCCCCTCAAGGAG

CAGCCCGCCCTCAATGACTCCAGATACTGCCTGAGCAGCCGCCTGAGGGT

CTCGGCCACCTTCTGGCAGAACCCCGCAACCACTTCCGCTGTCAAGTCC

AGTTCTACGGGCTCTCGGAGAATGACGAGTGGACCCAGGATAGGGCCAAA

CCCGTCACCCAGATCGTCAGCGCCGAGGCCTGGGGTAGAGCAGACTGTGG

CTTTACCTCGGTGTCCTACCAGCAAGGGGTCCTGTCTGCCACCATCCTCT

ATGAGATCCTGCTAGGGAAGGCCACCCTGTATGCGTGCTGGTCAGCGCC

CTTGTGTTGATGGCCATGGTCAAGAGAAAGGATTTCTGA
```

(b) Amino Acid Sequence of TCR α and Chains for SB95 (TCR Variable Regions are in Italic, CDR3 Regions are in Bold)

TCR α chain
(SEQ ID NO: 57)

MLLLLVPVLEVIFTLGGTRAQSVTQLGSHVSVSEGALVLLRCNYSSSVPPYLF

WYVQYPNQGLQLLLKHTTGATLVKGINGFEAEFKKSETSFHLTKPSAHMSDAAEYF*CAVS*

*DSRAAGNKLTF*GGGTRVLVKPNIQNPDPAVYQLRDSKSSDKSVCLFTDFDSQTNVSQS

KDSDVYITDKTVLDMRSMDFKSNSAVAWSNKSDFACANAFNNSIIPEDTFFPSPESSC

DVKLVEKSFETDTNLNFQNLSVIGFRILLLKVAGFNLLMTLRLWSS

TCR β chain
(SEQ ID NO: 58)

MGIRLLCRVAFCFLAVGLVDVKVTQSSRYLVKRTGEKVFLECVQDMDHEN

MFWYRQDPGLGLRLIYFSYDVKMKEKGDIPEGYSVSREKKERFSLILESASINQTSMYL*CA*

*SRFPGTAYNSPLH*FGNGTRLTVTEDLNKVFPPEVAVFEPSEAEISHTQKATLVCLATGF

FPDHVELSWWVNGKEVHSGVSTDPQPLKEQPALNDSRYCLSSRLRVSATFWQNPRN

HFRCQVQFYGLSENDEWTQDRAKPVTQIVSAEAWGRADCGFTSVSYQQGVLSATIL

YEILLGKATLYAVLVSALVLMAMVKRKDF

FIG. 4 provides a non-limiting example of an expression vector that can be used to express any of the TCRs of this Example. For FIG. 4: (A) Retrovirus vector used to express TCRs. LTR: long-terminal repeat; w: packaging signal; MCS: multiple cloning site; IRES: internal ribosome entry site; eGFP: enhanced green fluorescent protein. (B) TCR expressing cassette. (I) TCR β and α chain-coding cDNA sequences are connected by a GSG (Gly-Ser-Gly) linker and a P2A ribosomal skipping sequence. (II) TCR β and α chain-coding cDNA sequences are connected by a furin protease recognition site (RAKR (Arg-Ala-Lys-Arg)), a SGSG (Ser-Gly-Ser-Gly) linker, V5 epitope, and a P2A ribosomal skipping sequence.

As described in PCT PCT/U.S. Ser. No. 14/25673, the TCRs of this Example are capable of promoting direct recognition of cancer cells and inducing apoptosis of them. Further, CD4+ T cells expressing the TCRs of this Example were found to efficiently enhance the cytotoxic activity of tumor antigen-specific CD8+ T cells via direct recognition of cancer cells in the absence of antigen-presenting cells. Additionally, CD8+ T cells co-stimulated with CD4+ T cells expressing recombinant TCRs of this Example actively proliferated and upregulated central memory T cell markers, and CD4+ T cells expressing these TCRs showed significant in vivo anti-tumor activity to inhibit the growth of human cancer cells in immuno-deficient mice, and these CD4+ T cells with tumor antigen-specific CD8+ T cells co-operatively inhibited in vivo tumor growth.

HLA allele frequencies for different ethnic populations in the United States. (Shown for 10 most frequent types in European Americans in Table 1). Data for HLA-A, B, C, DR, and DQ were obtained and modified from The National Marrow Donor Program® (NMDP)/Be The Match® website: bioinformatics.bethematchclinical.org/. Data for HLA-DP were obtained from The Allele Frequency Net Database: www.allelefrequencies.net/contact.asp.

In an embodiment, a library of this disclosure contains a plurality of NY-ESO-1-specific TCRs restricted by the underlined/bold HLA types in Table 1 below.

TABLE 1

| HLA-A | EUR_freq | EUR_rank | AFA_freq | AFA_rank | API_freq | API_rank | HIS_freq | HIS_rank |
|---|---|---|---|---|---|---|---|---|
| 0201 | 0.29604 | 1 | 0.12458 | 1 | 0.09458 | 3 | 0.19403 | 1 |
| 0101 | 0.17181 | 2 | 0.04742 | 8 | 0.05082 | 5 | 0.06702 | 4 |
| 0301 | 0.14347 | 3 | 0.08132 | 3 | 0.02597 | 11 | 0.07907 | 3 |
| 2402 | 0.08686 | 4 | 0.02205 | 15 | 0.18238 | 1 | 0.12324 | 2 |
| 1101 | 0.05642 | 5 | 0.01581 | 18 | 0.17899 | 2 | 0.04618 | 7 |
| 2902 | 0.03279 | 6 | 0.03640 | 12 | 0.00141 | 30 | 0.04167 | 8 |
| 3201 | 0.03133 | 7 | 0.01414 | 21 | 0.01299 | 18 | 0.02711 | 13 |
| 2601 | 0.02948 | 8 | 0.01414 | 20 | 0.03896 | 8 | 0.02887 | 11 |
| 6801 | 0.02503 | 9 | 0.03681 | 11 | 0.01863 | 13 | 0.04694 | 6 |
| 3101 | 0.02351 | 10 | 0.01040 | 22 | 0.03247 | 9 | 0.04794 | 5 |
| HLA-B | EUR_freq | EUR_rank | AFA_freq | AFA_rank | API_freq | API_rank | HIS_freq | HIS_rank |
| 0702 | 0.13987 | 1 | 0.07303 | 2 | 0.02632 | 15 | 0.05453 | 4 |
| 0801 | 0.12525 | 2 | 0.03838 | 9 | 0.01641 | 21 | 0.04452 | 6 |
| 4402 | 0.09011 | 3 | 0.02116 | 17 | 0.00764 | 32 | 0.03327 | 9 |
| 1501 | 0.06654 | 4 | 0.00975 | 23 | 0.03480 | 11 | 0.02876 | 10 |
| 3501 | 0.05713 | 5 | 0.06494 | 3 | 0.04273 | 5 | 0.06353 | 1 |
| 4001 | 0.05643 | 6 | 0.01328 | 21 | 0.07980 | 1 | 0.01351 | 26 |
| 4403 | 0.04963 | 7 | 0.05373 | 6 | 0.04244 | 6 | 0.06078 | 2 |
| 1801 | 0.04620 | 8 | 0.03568 | 10 | 0.01160 | 25 | 0.03952 | 8 |
| 5101 | 0.04544 | 9 | 0.02178 | 16 | 0.06282 | 2 | 0.05778 | 3 |
| 5701 | 0.03832 | 10 | 0.00477 | 35 | 0.02066 | 18 | 0.01176 | 29 |

TABLE 1-continued

| C | EUR_freq | EUR_rank | AFA_freq | AFA_rank | API_freq | API_rank | HIS_freq | HIS_rank |
|---|---|---|---|---|---|---|---|---|
| 0701 | 0.16658 | 1 | 0.12401 | 2 | 0.03894 | 12 | 0.10355 | 3 |
| 0702 | 0.15006 | 2 | 0.06968 | 7 | 0.14560 | 1 | 0.11281 | 2 |
| 0401 | 0.10534 | 3 | 0.18457 | 1 | 0.08070 | 4 | 0.16508 | 1 |
| 0602 | 0.09301 | 4 | 0.08855 | 4 | 0.06518 | 6 | 0.05878 | 5 |
| 0501 | 0.09136 | 5 | 0.03526 | 10 | 0.00847 | 18 | 0.04652 | 9 |
| 0304 | 0.08215 | 6 | 0.05330 | 8 | 0.08352 | 3 | 0.06978 | 4 |
| 0303 | 0.05457 | 7 | 0.01182 | 16 | 0.05023 | 8 | 0.03402 | 12 |
| 1203 | 0.04892 | 8 | 0.01783 | 12 | 0.02737 | 13 | 0.04127 | 11 |
| 0802 | 0.03875 | 9 | 0.03733 | 9 | 0.00395 | 22 | 0.04927 | 8 |
| 0202 | 0.03729 | 10 | 0.08461 | 5 | 0.00395 | 21 | 0.04227 | 10 |

| DRB1 | EUR_freq | EUR_rank | AFA_freq | AFA_rank | API_freq | API_rank | HIS_freq | HIS_rank |
|---|---|---|---|---|---|---|---|---|
| 1501 | 0.14441 | 1 | 0.02931 | 14 | 0.07919 | 4 | 0.06678 | 4 |
| 0701 | 0.13767 | 2 | 0.09771 | 2 | 0.08201 | 2 | 0.10455 | 1 |
| 0301 | 0.12916 | 3 | 0.07069 | 4 | 0.05373 | 7 | 0.07329 | 2 |
| 0101 | 0.09149 | 4 | 0.02599 | 15 | 0.02743 | 14 | 0.03877 | 9 |
| 0401 | 0.09111 | 5 | 0.02287 | 16 | 0.00905 | 22 | 0.01451 | 22 |
| 1301 | 0.06283 | 6 | 0.05551 | 7 | 0.02376 | 16 | 0.04202 | 7 |
| 1101 | 0.05654 | 7 | 0.08711 | 3 | 0.05119 | 9 | 0.04202 | 8 |
| 1302 | 0.04015 | 8 | 0.06445 | 6 | 0.03620 | 10 | 0.03877 | 10 |
| 0404 | 0.03634 | 9 | 0.00686 | 22 | 0.00905 | 23 | 0.05453 | 6 |
| 1104 | 0.03189 | 10 | 0.00561 | 23 | 0.00650 | 24 | 0.02551 | 13 |

| DQB1 | EUR_freq | EUR_rank | AFA_freq | AFA_rank | API_freq | API_rank | HIS_freq | HIS_rank |
|---|---|---|---|---|---|---|---|---|
| 0201 | 0.23030 | 1 | 0.22314 | 1 | 0.10915 | 4 | 0.18525 | 3 |
| 0301 | 0.18450 | 2 | 0.17374 | 3 | 0.19410 | 1 | 0.20046 | 1 |
| 0602 | 0.14250 | 3 | 0.19801 | 2 | 0.04401 | 10 | 0.08065 | 6 |
| 0501 | 0.12281 | 4 | 0.15381 | 4 | 0.07394 | 6 | 0.11014 | 4 |
| 0302 | 0.09504 | 5 | 0.03683 | 6 | 0.07614 | 5 | 0.18894 | 2 |
| 0603 | 0.06512 | 6 | 0.02340 | 9 | 0.02289 | 12 | 0.04055 | 7 |
| 0303 | 0.04460 | 7 | 0.01646 | 11 | 0.12192 | 2 | 0.02074 | 9 |
| 0604 | 0.03240 | 8 | 0.01950 | 10 | 0.01364 | 14 | 0.02765 | 8 |
| 0402 | 0.02529 | 9 | 0.06846 | 5 | 0.02333 | 11 | 0.09078 | 5 |
| 0503 | 0.02497 | 10 | 0.01473 | 12 | 0.06206 | 8 | 0.01336 | 12 |

| HLA-DP | Caucasian | | African American | Mexican American |
|---|---|---|---|---|
| 0101 | 0.062 | 4 | 0.272 | 0.031 |
| 0201 | 0.131 | 2 | 0.13 | 0.093 |
| 0202 | 0.007 | 9 | NA | 0.027 |
| 0301 | 0.09 | 8 | 0.057 | 0.044 |
| 0401 | 0.425 | 1 | 0.104 | 0.204 |
| 0402 | 0.121 | 3 | 0.111 | 0.398 |
| 0501 | 0.015 | 6 | 0.005 | 0.035 |
| 0601 | 0.021 | 5 | 0.003 | 0.009 |
| 0901 | 0.004 | 10 | 0.005 | 0.013 |
| 1001 | 0.013 | 7 | NA | 0.027 |

While the disclosure has been particularly shown and described with reference to specific embodiments, it should be understood by those having skill in the art that various changes in form and detail may be made therein without departing from the spirit and scope of the present disclosure as disclosed herein.

---

What is claimed is:

1. A recombinant polynucleotide encoding an alpha chain and/or a beta chain of a T cell receptor (TCR) selected from TCRs 19305DP, AL, KQ, PP, BB, KB, ST, JD, PB-P, PB-T, PB13.2, and 19305CD8, wherein the alpha chain and/or the beta chain comprises at least one of:

i) for 19305DP, an alpha chain comprising the sequence of SEQ ID NO:1 and/or a beta chain comprising the sequence of SEQ ID NO:2;

ii) for AL, an alpha chain comprising the sequence of SEQ ID NO:5 and/or a beta chain comprising the sequence of SEQ ID NO:6;

iii) for KQ, an alpha chain comprising the sequence of SEQ ID NO:9 and/or a beta chain comprising the sequence of SEQ ID NO:10;

iv) for PP, an alpha chain comprising the sequence of SEQ ID NO:13 and/or a beta chain comprising the sequence of SEQ ID NO:14;

v) for BB, an alpha chain comprising the sequence of SEQ ID NO:17 and/or a beta chain comprising the sequence of SEQ ID NO:18;

vi) for KB, an alpha chain comprising the sequence of SEQ ID NO:21 and/or a beta chain comprising the sequence of SEQ ID NO:22, vii) for ST, an alpha chain comprising the sequence of SEQ ID NO:25 and/or a beta chain comprising the sequence of SEQ ID NO:26;

viii) for JD, an alpha chain comprising the sequence of SEQ ID NO:29 and/or a beta chain comprising the sequence of SEQ ID NO:30, ix) for PB-P, an alpha chain comprising the sequence of SEQ ID NO:33 and/or a beta chain comprising the sequence of SEQ ID NO:34;

x) for PB-T, an alpha chain comprising the sequence of SEQ ID NO:37 and/or a beta chain comprising the sequence of SEQ ID NO:38, xi) for PB13.2, an alpha chain comprising the sequence of SEQ ID NO:41 and/or a beta chain comprising the sequence of SEQ ID NO:42, and xii) for 19305CD8, an alpha chain comprising the sequence of SEQ ID NO:45 and/or a beta chain comprising the sequence of SEQ ID NO:46.

2. The recombinant polynucleotide of claim 1 encoding the 19305DP alpha chain comprising the sequence of SEQ ID NO:1 and/or the 19305DP beta chain comprising the sequence of SEQ ID NO:2.

3. The recombinant polynucleotide of claim 2 encoding the 19305DP alpha chain comprising the sequence of SEQ ID NO:1 and the 19305DP beta chain comprising the sequence of SEQ ID NO:2.

4. The recombinant polynucleotide of claim 1, wherein the recombinant polynucleotide is present in an expression vector.

5. The recombinant polynucleotide of claim 4, wherein the expression vector is present in a cell.

6. The recombinant polynucleotide of claim 5, wherein the expression vector is present in a cell that is a CD4+ T cell or a CD8+ T cell.

7. The recombinant polynucleotide of claim 6, wherein the expression vector encodes the 19305DP alpha chain comprising the sequence of SEQ ID NO:1 and/or the 19305DP beta chain comprising the sequence of SEQ ID NO:2.

8. The recombinant polynucleotide of claim 6, wherein the expression vector encodes the 19305DP alpha chain comprising the sequence of SEQ ID NO:1 and the 19305DP beta chain comprising the sequence of SEQ ID NO:2.

9. A method for therapy of an individual diagnosed with, suspected of having or at risk for developing or recurrence of a cancer, wherein the cancer comprises cancer cells which express NY-ESO-1/LAGE-1 antigen, the method comprising administering to the individual modified human T cells comprising an expression vector of claim 4.

10. The method of claim 9, wherein the cancer cells are selected from bladder cancer cells, brain cancer cells, breast cancer cells, gastric cancer cells, esophageal cancer cells, head and neck cancer cells, hepatobiliary cancer cells, kidney cancer cells, ovary cancer cells, non-small cell lung cancer cells, myeloma, prostate cancer cells, sarcoma cells, testicular cancer cells, melanoma cells, or combinations thereof.

11. The method of claim 9, comprising removing T cells from the individual prior to the administering, and modifying the T cells by introducing into the T cells the expression vector.

12. The method of claim 11, wherein the expression vector encodes the 19305DP alpha chain comprising the sequence of SEQ ID NO:1 and/or the 19305DP beta chain comprising the sequence of SEQ ID NO:2.

13. The method of claim 11, wherein the expression vector encodes the 19305DP alpha chain comprising the sequence of SEQ ID NO:1 and the 19305DP beta chain comprising the sequence of SEQ ID NO:2.

14. The method of claim 11, wherein the modified T cells in which the expression vector is present comprise CD4+ T cells, CD8+ T cells, or a combination thereof.

15. A library comprising a plurality of recombinant polynucleotides encoding the alpha chains and/or beta chain of T cell receptors (TCRs) of claim 1.

16. The library of claim 15, wherein the recombinant polynucleotides are present in expression vectors.

17. The library of claim 16, wherein the recombinant polynucleotide encodes the 19305DP alpha chain comprising the sequence of SEQ ID NO:1 and/or the 19305DP beta chain comprising the sequence of SEQ ID NO:2.

18. The library of claim 17, wherein the recombinant polynucleotide encodes the 19305DP alpha chain comprising the sequence of SEQ ID NO:1 and the 19305DP beta chain comprising the sequence of SEQ ID NO:2.

19. The library of claim 17, further comprising at least one additional recombinant polynucleotide encoding at least one TCR alpha chain and/or at least one TCR beta chain from AL, KQ, PP, BB, KB, ST, JD, PB-P, PB-T, PB13.2, 19305CD8, JM, 5B8, and SB95 TCRs.

* * * * *

SEQUENCE LISTING

```
<160> NUMBER OF SEQ ID NOS: 66

<210> SEQ ID NO 1
<211> LENGTH: 270
<212> TYPE: PRT
<213> ORGANISM: Human

<400> SEQUENCE: 1

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45
```

```
Ile Asn Asn Leu Gln Trp Tyr Arg Gln Asn Ser Gly Arg Gly Leu Val
 50                  55                  60

His Leu Ile Leu Ile Arg Ser Asn Glu Arg Glu Lys His Ser Gly Arg
 65                  70                  75                  80

Leu Arg Val Thr Leu Asp Thr Ser Lys Lys Ser Ser Ser Leu Leu Ile
                 85                  90                  95

Thr Ala Ser Arg Ala Ala Asp Thr Ala Ser Tyr Phe Cys Ala Thr Asp
                100                 105                 110

Gly Gly Gly Thr Leu Thr Phe Gly Lys Gly Thr Met Leu Leu Val Ser
            115                 120                 125

Pro Asp Ile Gln Asn Pro Asp Pro Ala Val Tyr Gln Leu Arg Asp Ser
130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
                180                 185                 190

Ala Trp Ser Asn Lys Ser Asp Phe Ala Cys Ala Asn Ala Phe Asn Asn
                195                 200                 205

Ser Ile Ile Pro Glu Asp Thr Phe Phe Pro Ser Pro Glu Ser Ser Cys
210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
                260                 265                 270

<210> SEQ ID NO 2
<211> LENGTH: 308
<212> TYPE: PRT
<213> ORGANISM: Human

<400> SEQUENCE: 2

Met Asp Ser Trp Thr Leu Cys Cys Val Ser Leu Cys Ile Leu Val Ala
 1               5                  10                  15

Lys His Thr Asp Ala Gly Val Ile Gln Ser Pro Arg His Glu Val Thr
                 20                  25                  30

Glu Met Gly Gln Glu Val Thr Leu Arg Cys Lys Pro Ile Ser Gly His
             35                  40                  45

Asp Tyr Leu Phe Trp Tyr Arg Gln Thr Met Met Arg Gly Leu Glu Leu
 50                  55                  60

Leu Ile Tyr Phe Asn Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                 85                  90                  95

Lys Ile Gln Pro Ser Glu Pro Arg Asp Ser Ala Val Tyr Phe Cys Ala
                100                 105                 110

Ser Lys Trp Gly Gly Thr Glu Ala Phe Phe Gly Gln Gly Thr Arg Leu
            115                 120                 125

Thr Val Val Glu Asp Leu Asn Lys Val Phe Pro Pro Glu Val Ala Val
130                 135                 140

Phe Glu Pro Ser Glu Ala Glu Ile Ser His Thr Gln Lys Ala Thr Leu
```

```
                145                 150                 155                 160
Val Cys Leu Ala Thr Gly Phe Phe Pro Asp His Val Glu Leu Ser Trp
                    165                 170                 175
Trp Val Asn Gly Lys Glu Val His Ser Gly Val Ser Thr Asp Pro Gln
                    180                 185                 190
Pro Leu Lys Glu Gln Pro Ala Leu Asn Asp Ser Arg Tyr Cys Leu Ser
                    195                 200                 205
Ser Arg Leu Arg Val Ser Ala Thr Phe Trp Gln Asn Pro Arg Asn His
                    210                 215                 220
Phe Arg Cys Gln Val Gln Phe Tyr Gly Leu Ser Glu Asn Asp Glu Trp
225                 230                 235                 240
Thr Gln Asp Arg Ala Lys Pro Val Thr Gln Ile Val Ser Ala Glu Ala
                    245                 250                 255
Trp Gly Arg Ala Asp Cys Gly Phe Thr Ser Val Ser Tyr Gln Gln Gly
                    260                 265                 270
Val Leu Ser Ala Thr Ile Leu Tyr Glu Ile Leu Leu Gly Lys Ala Thr
                    275                 280                 285
Leu Tyr Ala Val Leu Val Ser Ala Leu Val Leu Met Ala Met Val Lys
                    290                 295                 300
Arg Lys Asp Phe
305

<210> SEQ ID NO 3
<211> LENGTH: 813
<212> TYPE: DNA
<213> ORGANISM: Human

<400> SEQUENCE: 3
atggaaactc tcctgggagt gtctttggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggcettg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct acggacgggg ggggcaccct cacctttggg     360
aaggggacta tgcttctagt ctctccagat atccagaacc tgaccctgc cgtgtaccag     420
ctgagagact ctaaatccag tgacaagtct gtctgcctat tcaccgattt tgattctcaa     480
acaaatgtgt cacaaagtaa ggattctgat gtgtatatca cagacaaaac tgtgctagac     540
atgaggtcta tggacttcaa gagcaacagt gctgtggcct ggagcaacaa atctgacttt     600
gcatgtgcaa acgccttcaa caacagcatt attccagaag acaccttctt ccccagccca     660
gaaagttcct gtgatgtcaa gctggtcgag aaaagctttg aaacagatac gaacctaaac     720
tttcaaaacc tgtcagtgat tgggttccga atcctcctcc tgaaagtggc cgggtttaat     780
ctgctcatga cgctgcggct gtggtccagc tga                                  813

<210> SEQ ID NO 4
<211> LENGTH: 927
<212> TYPE: DNA
<213> ORGANISM: Human

<400> SEQUENCE: 4
atggactcct ggaccctctg ctgtgtgtcc ctttgcatcc tggtagcaaa gcacacagat      60
gctggagtta tccagtcacc ccggcacgag gtgacagaga tgggacaaga agtgactctg     120
```

```
agatgtaaac caatttcagg acacgactac ctttctggt acagacagac catgatgcgg      180
ggactggagt tgctcattta ctttaacaac aacgttccga tagatgattc agggatgccc      240
gaggatcgat tctcagctaa gatgcctaat gcatcattct ccactctgaa gatccagccc      300
tcagaaccca gggactcagc tgtgtacttc tgtgccagca agtggggcgg cactgaagct      360
ttctttggac aaggcaccag actcacagtt gtagaggacc tgaacaaggt gttcccaccc      420
gaggtcgctg tgtttgagcc atcagaagca gagatctccc acacccaaaa ggccacactg      480
gtgtgcctgg ccacaggctt cttccctgac acgtggagc tgagctggtg ggtgaatggg       540
aaggaggtgc acagtgggt cagcacggac ccgcagcccc tcaaggagca gcccgccctc       600
aatgactcca gatactgcct gagcagccgc ctgagggtct cggccacctt ctggcagaac      660
ccccgcaacc acttccgctg tcaagtccag ttctacgggc tctcggagaa tgacgagtgg      720
acccaggata gggccaaacc cgtcacccag atcgtcagcg ccgaggcctg ggtagagca      780 gactgtggct ttacctcggt gtcctaccag caaggggtcc tgtctgccac catcctctat      840
gagatcctgc tagggaaggc caccctgtat gctgtgctgg tcagcgccct tgtgttgatg      900
gccatggtca agagaaagga tttctga                                          927
```

<210> SEQ ID NO 5
<211> LENGTH: 277
<212> TYPE: PRT
<213> ORGANISM: Human

<400> SEQUENCE: 5

```
Met Met Lys Ser Leu Arg Val Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
            35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Gly Gly Leu Thr Ser Ser Asn Thr Gly Lys Leu Ile Phe Gly Gln
            115                 120                 125

Gly Thr Thr Leu Gln Val Lys Pro Asp Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
    210                 215                 220
```

```
Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
            245                 250                 255

Arg Ile Leu Leu Leu Lys Val Ala Gly Phe Asn Leu Leu Met Thr Leu
        260                 265                 270

Arg Leu Trp Ser Ser
        275

<210> SEQ ID NO 6
<211> LENGTH: 307
<212> TYPE: PRT
<213> ORGANISM: Human

<400> SEQUENCE: 6

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Asn Gln Ile Tyr Gly Tyr Thr Phe Gly Ser Gly Thr Arg Leu Thr
        115                 120                 125

Val Val Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
290                 295                 300

Lys Asp Phe
305
```

<210> SEQ ID NO 7
<211> LENGTH: 834
<212> TYPE: DNA
<213> ORGANISM: Human

<400> SEQUENCE: 7

```
atgatggcag gcattcgagc tttatttatg tacttgtggc tgcagctgga ctgggtgagc    60
agaggagaga gtgtggggct gcatcttcct accctgagtg tccaggaggg tgacaactct   120
attatcaact gtgcttattc aaacagcgcc tcagactact tcatttggta caagcaagaa   180
tctggaaaag gtcctcaatt cattatagac attcgttcaa atatgacaa aaggcaaggc   240
caaagagtca ccgttttatt gaataagaca gtgaaacatc tctctctgca aattgcagct   300
actcaacctg gagactcagc tgtctacttt tgtgcagaga ataccgcccc acataatgca   360
ggcaacatgc tcacctttgg agggggaaca aggttaatgg tcaaaccccca tatccagaac   420
cctgaccctg ccgtgtacca gctgagagac tctaaatcca gtgacaagtc tgtctgccta   480
ttcaccgatt ttgattctca aacaaatgtg tcacaaagta aggattctga tgtgtatatc   540
acagacaaaa ctgtgctaga catgaggtct atggacttca gagcaacag tgctgtggcc   600
tggagcaaca atctgacttt gcatgtgca aacgccttca caacagcat tattccagaa   660
gacaccttct tccccagccc agaaagttcc tgtgatgtca agctggtcga gaaaagcttt   720
gaaacagata cgaacctaaa ctttcaaaac ctgtcagtga ttgggttccg aatcctcctc   780
ctgaaagtgg ccgggtttaa tctgctcatg acgctgcggc tgtggtccag ctga          834
```

<210> SEQ ID NO 8
<211> LENGTH: 933
<212> TYPE: DNA
<213> ORGANISM: Human

<400> SEQUENCE: 8

```
atgggccctg ggctcctctg ctgggtgctg ctttgtctcc tgggagcagg cccagtggac    60
gctggagtca cccaaagtcc cacacacctg atcaaaacga gaggacagca agtgactctg   120
agatgctctc ctatctctgg gcacaagagt gtgtcctggt accaacaggt cctgggtcag   180
gggccccagt ttatctttca gtattatgag aaagaagaga gaggaagagg aaacttccct   240
gatcgattct cagctcgcca gttccctaac tatagctctg agctgaatgt gaacgccttg   300
ttgctggggg actcggccct gtatctctgt gccagcagct acgacagggg gataaactat   360
ggctacacct tcggttcggg gaccaggtta accgttgtag aggacctgaa caaggtgttc   420
ccacccgagg tcgctgtgtt tgagccatca gaagcagaga tctcccacac ccaaaaggcc   480
acactggtgt gcctggccac aggcttcttc cctgaccacg tggagctgag ctggtgggtg   540
aatgggaagg aggtgcacag tggggtcagc acggacccgc agcccctcaa ggagcagccc   600
gccctcaatg actccagata ctgcctgagc agccgcctga gggtctcggc caccttctgg   660
cagaaccccc gcaaccactt ccgctgtcaa gtccagttct acgggctctc ggagaatgac   720
gagtggaccc aggatagggc caaacccgtc acccagatcg tcagcgccga ggcctggggt   780
agagcagact gtggctttac ctcggtgtcc taccagcaag ggtcctgtc tgccaccatc   840
ctctatgaga tcctgctagg gaaggccacc ctgtatgctg tgctggtcag cgcccttgtg   900
ttgatggcca tggtcaagag aaaggatttc tga                                933
```

<210> SEQ ID NO 9

```
<211> LENGTH: 277
<212> TYPE: PRT
<213> ORGANISM: Human

<400> SEQUENCE: 9

Met Met Ala Gly Ile Arg Ala Leu Phe Met Tyr Leu Trp Leu Gln Leu
1               5                   10                  15

Asp Trp Val Ser Arg Gly Glu Ser Val Gly Leu His Leu Pro Thr Leu
            20                  25                  30

Ser Val Gln Glu Gly Asp Asn Ser Ile Ile Asn Cys Ala Tyr Ser Asn
        35                  40                  45

Ser Ala Ser Asp Tyr Phe Ile Trp Tyr Lys Gln Glu Ser Gly Lys Gly
    50                  55                  60

Pro Gln Phe Ile Ile Asp Ile Arg Ser Asn Met Asp Lys Arg Gln Gly
65                  70                  75                  80

Gln Arg Val Thr Val Leu Leu Asn Lys Thr Val Lys His Leu Ser Leu
                85                  90                  95

Gln Ile Ala Ala Thr Gln Pro Gly Asp Ser Ala Val Tyr Phe Cys Ala
            100                 105                 110

Glu Asn Thr Ala Pro His Asn Ala Gly Asn Met Leu Thr Phe Gly Gly
        115                 120                 125

Gly Thr Arg Leu Met Val Lys Pro His Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 10
<211> LENGTH: 310
<212> TYPE: PRT
<213> ORGANISM: Human

<400> SEQUENCE: 10

Met Gly Pro Gly Leu Leu Cys Trp Val Leu Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln Gln Val Thr Leu Arg Cys Ser Pro Ile Ser Gly His
        35                  40                  45

Lys Ser Val Ser Trp Tyr Gln Gln Val Leu Gly Gln Gly Pro Gln Phe
    50                  55                  60
```

```
Ile Phe Gln Tyr Tyr Glu Lys Glu Arg Gly Arg Gly Asn Phe Pro
 65                  70                  75                  80

Asp Arg Phe Ser Ala Arg Gln Phe Pro Asn Tyr Ser Glu Leu Asn
                 85                  90                  95

Val Asn Ala Leu Leu Leu Gly Asp Ser Ala Leu Tyr Leu Cys Ala Ser
            100                 105                 110

Ser Tyr Asp Arg Gly Ile Asn Tyr Gly Tyr Thr Phe Gly Ser Gly Thr
            115                 120                 125

Arg Leu Thr Val Val Glu Asp Leu Asn Lys Val Phe Pro Pro Glu Val
            130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
290                 295                 300

Val Lys Arg Lys Asp Phe
305                 310

<210> SEQ ID NO 11
<211> LENGTH: 822
<212> TYPE: DNA
<213> ORGANISM: Human

<400> SEQUENCE: 11
atggcctctg cacccatctc gatgcttgcg atgctcttca cattgagtgg gctgagagct      60
cagtcagtgg ctcagccgga agatcaggtc aacgttgctg aagggaatcc tctgactgtg     120
aaatgcacct attcagtctc tggaaaccct tatctttttt ggtatgttca ataccccaac     180
cgaggcctcc agttccttct gaaatacatc acaggggata acctggttaa aggcagctat     240
ggctttgaag ctgaatttaa caagagccaa acctccttcc acctgaagaa accatctgcc     300
cttgtgagcg actccgcttt gtacttctgt gctgtgagag atgttgtgga ggggaaattg     360
cagtttggag cagggaccca ggttgtggtc accccagata tccagaaccc tgaccctgcc     420
gtgtaccagc tgagagactc taaatccagt gacaagtctg tctgcctatt caccgatttt     480
gattctcaaa caaatgtgtc acaaagtaag gattctgatg tgtatatcac agacaaaact     540
gtgctagaca tgaggtctat ggacttcaag agcaacagtg ctgtggcctg agcaacaaaa     600
tctgactttg catgtgcaaa cgccttcaac aacagcatta ttccagaaga caccttcttc     660
```

| cccagcccag aaagttcctg tgatgtcaag ctggtcgaga aaagctttga aacagatacg | 720 |
| aacctaaact ttcaaaacct gtcagtgatt gggttccgaa tcctcctcct gaaagtggcc | 780 |
| gggtttaatc tgctcatgac gctgcggctg tggtccagct ga | 822 |

<210> SEQ ID NO 12
<211> LENGTH: 936
<212> TYPE: DNA
<213> ORGANISM: Human

<400> SEQUENCE: 12

| atgggcacca gcctcctctg ctggatggcc ctgtgtctcc tgggggcaga tcacgcagat | 60 |
| actggagtct cccaggaccc cagacacaag atcacaaaga ggggacagaa tgtaactttc | 120 |
| aggtgtgatc aatttctga acacaaccgc ctttattggt accgacagac cctggggcag | 180 |
| ggcccagagt ttctgactta cttccagaat gaagctcaac tagaaaaatc aaggctgctc | 240 |
| agtgatcggt tctctgcaga gaggcctaag ggatctttct ccaccttgga gatccagcgc | 300 |
| acagagcagg gggactcggc catgtatctc tgtgccagca gcaccacaag ctcctacgag | 360 |
| cagtacttcg gccgggcac caggctcacg gtcacagagg acctgaaaaa cgtgttccca | 420 |
| cccgaggtcg ctgtgtttga gccatcagaa gcagagatct cccacaccca aaaggccaca | 480 |
| ctggtgtgcc tggccacagg cttctacccc gaccacgtgg agctgagctg gtgggtgaat | 540 |
| gggaaggag tgcacagtgg ggtcagcaca gacccgcagc ccctcaagga gcagcccgcc | 600 |
| ctcaatgact ccagatactg cctgagcagc cgcctgaggg tctcggccac cttctggcag | 660 |
| aaccccccgca accacttccg ctgtcaagtc cagttctacg gctctcggga gaatgacgag | 720 |
| tggacccagg atagggccaa acctgtcacc cagatcgtca gcgccgaggc ctggggtaga | 780 |
| gcagactgtg gcttcacctc cgagtcttac cagcaagggg tcctgtctgc caccatcctc | 840 |
| tatgagatct gctagggaa ggccaccttg tatgccgtgc tggtcagtgc cctcgtgctg | 900 |
| atggccatgg tcaagagaaa ggattccaga ggctag | 936 |

<210> SEQ ID NO 13
<211> LENGTH: 273
<212> TYPE: PRT
<213> ORGANISM: Human

<400> SEQUENCE: 13

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Val Val Glu Gly Lys Leu Gln Phe Gly Ala Gly Thr Gln Val
        115                 120                 125

Val Val Thr Pro Asp Ile Gln Asn Pro Asp Pro Ala Val Tyr Gln Leu

```
                130                 135                 140
Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
                195                 200                 205

Phe Asn Asn Ser Ile Ile Pro Glu Asp Thr Phe Phe Pro Ser Pro Glu
            210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 14
<211> LENGTH: 311
<212> TYPE: PRT
<213> ORGANISM: Human

<400> SEQUENCE: 14

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Thr Thr Ser Ser Tyr Glu Gln Tyr Phe Gly Pro Gly Thr Arg
        115                 120                 125

Leu Thr Val Thr Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
```

| | 225 | | | 230 | | | 235 | | | 240 | |
|---|---|---|---|---|---|---|---|---|---|---|---|
Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 15
<211> LENGTH: 825
<212> TYPE: DNA
<213> ORGANISM: Human

<400> SEQUENCE: 15

```
atgatggcag gcattcgagc tttatttatg tacttgtggc tgcagctgga ctgggtgagc      60
agaggagaga gtgtggggct gcatcttcct accctgagtg tccaggaggg tgacaactct     120
attatcaact gtgcttattc aaacagcgcc tcagactact tcatttggta caagcaagaa     180
tctggaaaag tcctcaatt cattatagac attcgttcaa atatggacaa aaggcaaggc      240
caaagagtca ccgtttttatt gaataagaca gtgaaacatc tctctctgca aattgcagct     300
actcaacctg agactcagc tgtctacttt tgtgcagagg cgggaggaag ccaaggaaat      360
ctcatctttg gaaaggcac taaactctct gttaaaccaa atatccagaa ccctgaccct      420
gccgtgtacc agctgagaga ctctaaatcc agtgacaagt ctgtctgcct attcaccgat      480
tttgattctc aaacaaatgt gtcacaaagt aaggattctg atgtgtatat cacagacaaa     540
actgtgctag acatgaggtc tatggacttc aagagcaaca gtgctgtggc ctggagcaac     600
aaatctgact tgcatgtgc aaacgcctc aacaacagca ttattccaga agacaccttc       660
ttccccagcc cagaaagttc ctgtgatgtc aagctggtcg agaaaagctt tgaaacagat     720
acgaacctaa actttcaaaa cctgtcagtg attgggttcc gaatcctcct cctgaaagtg     780
gccgggttta atctgctcat gacgctgcgg ctgtggtcca gctga                    825
```

<210> SEQ ID NO 16
<211> LENGTH: 942
<212> TYPE: DNA
<213> ORGANISM: Human

<400> SEQUENCE: 16

```
atgggccccg ggctcctctg ctgggcactg ctttgtctcc tgggagcagg cttagtggac      60
gctggagtca cccaaaagtcc cacacacctg atcaaaacga ggacagca gtgactctg      120
agatgctctc ctaagtctgg gcatgacact gtgtcctggt accaacaggc cctgggtcag     180
gggccccagt ttatctttca gtattatgag aggaagagaa acagagagg caacttccct      240
gatcgattct caggtcacca gttccctaac tatagctctg agctgaatgt gaacgccttg     300
ttgctggggg actcggccct ctatctctgt gccagcagct tttggggtcg ttctcaccct     360
tcaaactatg gctacacctt cggttcgggg accaggttaa ccgttgtaga ggacctgaac     420
aaggtgttcc cacccgaggt cgctgtgttt gagccatcag aagcagagat ctcccacacc     480
caaaaggcca cactggtgtg cctggccaca ggcttcttcc ctgaccacgt ggagctgagc     540
```

```
tggtgggtga atgggaagga ggtgcacagt ggggtcagca cggacccgca gcccctcaag    600
gagcagcccg ccctcaatga ctccagatac tgcctgagca gccgcctgag ggtctcggcc    660
accttctggc agaacccccg caaccacttc cgctgtcaag tccagttcta cgggctctcg    720
gagaatgacg agtggaccca ggatagggcc aaacccgtca cccagatcgt cagcgccgag    780
gcctggggta gagcagactg tggctttacc tcggtgtcct accagcaagg ggtcctgtct    840
gccaccatcc tctatgagat cctgctaggg aaggccaccc tgtatgctgt gctggtcagc    900
gcccttgtgt tgatggccat ggtcaagaga aaggatttct ga    942
```

<210> SEQ ID NO 17
<211> LENGTH: 274
<212> TYPE: PRT
<213> ORGANISM: Human

<400> SEQUENCE: 17

```
Met Met Ala Gly Ile Arg Ala Leu Phe Met Tyr Leu Trp Leu Gln Leu
1               5                   10                  15

Asp Trp Val Ser Arg Gly Glu Ser Val Gly Leu His Leu Pro Thr Leu
                20                  25                  30

Ser Val Gln Glu Gly Asp Asn Ser Ile Ile Asn Cys Ala Tyr Ser Asn
            35                  40                  45

Ser Ala Ser Asp Tyr Phe Ile Trp Tyr Lys Gln Glu Ser Gly Lys Gly
        50                  55                  60

Pro Gln Phe Ile Ile Asp Ile Arg Ser Asn Met Asp Lys Arg Gln Gly
65                  70                  75                  80

Gln Arg Val Thr Val Leu Leu Asn Lys Thr Val Lys His Leu Ser Leu
                85                  90                  95

Gln Ile Ala Ala Thr Gln Pro Gly Asp Ser Ala Val Tyr Phe Cys Ala
            100                 105                 110

Glu Ala Gly Gly Ser Gln Gly Asn Leu Ile Phe Gly Lys Gly Thr Lys
        115                 120                 125

Leu Ser Val Lys Pro Asn Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 18
<211> LENGTH: 313
<212> TYPE: PRT

<213> ORGANISM: Human

<400> SEQUENCE: 18

| | | | | | | | | | | | | | | |
|---|---|---|---|---|---|---|---|---|---|---|---|---|---|---|
|Met|Gly|Pro|Gly|Leu|Leu|Cys|Trp|Ala|Leu|Leu|Cys|Leu|Leu|Gly|Ala|
|1| | | |5| | | |10| | | |15| | |

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
                20                  25                  30

Thr Arg Gly Gln Gln Val Thr Leu Arg Cys Ser Pro Lys Ser Gly His
            35                  40                  45

Asp Thr Val Ser Trp Tyr Gln Gln Ala Leu Gly Gln Gly Pro Gln Phe
        50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
                100                 105                 110

Ser Phe Trp Gly Arg Ser His Pro Ser Asn Tyr Gly Tyr Thr Phe Gly
            115                 120                 125

Ser Gly Thr Arg Leu Thr Val Val Glu Asp Leu Asn Lys Val Phe Pro
        130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Phe Pro Asp His
                165                 170                 175

Val Glu Leu Ser Trp Trp Val Asn Gly Lys Glu Val His Ser Gly Val
                180                 185                 190

Ser Thr Asp Pro Gln Pro Leu Lys Glu Gln Pro Ala Leu Asn Asp Ser
            195                 200                 205

Arg Tyr Cys Leu Ser Ser Arg Leu Arg Val Ser Ala Thr Phe Trp Gln
        210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Val
                260                 265                 270

Ser Tyr Gln Gln Gly Val Leu Ser Ala Thr Ile Leu Tyr Glu Ile Leu
            275                 280                 285

Leu Gly Lys Ala Thr Leu Tyr Ala Val Leu Val Ser Ala Leu Val Leu
        290                 295                 300

Met Ala Met Val Lys Arg Lys Asp Phe
305                 310

<210> SEQ ID NO 19
<211> LENGTH: 840
<212> TYPE: DNA
<213> ORGANISM: Human

<400> SEQUENCE: 19
atgaacatgc tgactgccag cctgttgagg gcagtcatag cctccatctg tgttgtatcc     60
agcatggctc agaaggtaac tcaagcgcag actgaaattt ctgtggtgga gaaggaggat    120
gtgaccttgg actgtgtgta tgaaacccgt gatactactt attacttatt ctggtacaag    180
caaccaccaa gtggagaatt ggttttcctt attcgtcgga actcttttga tgagcaaaat    240

```
gaaataagtg gtcggtattc ttggaacttc agaaatcca ccagttcctt caacttcacc      300
atcacagcct cacaagtcgt ggactcagca gtatacttct gtgctctgag tgaggcaagc      360
gggagagatg acaagatcat ctttggaaaa gggacacgac ttcatattct ccccaatatc      420
cagaaccctg accctgccgt gtaccagctg agagactcta aatccagtga caagtctgtc      480
tgcctattca ccgattttga ttctcaaaca aatgtgtcac aaagtaagga ttctgatgtg      540
tatatcacag acaaaactgt gctagacatg aggtctatgg acttcaagag caacagtgct      600
gtggcctgga gcaacaaatc tgactttgca tgtgcaaacg ccttcaacaa cagcattatt      660
ccagaagaca ccttcttccc cagcccagaa agttcctgtg atgtcaagct ggtcgagaaa      720
agctttgaaa cagatacgaa cctaaacttt caaaacctgt cagtgattgg gttccgaatc      780
ctcctcctga aagtggccgg gtttaatctg ctcatgacgc tgcggctgtg gtccagctga      840
```

```
<210> SEQ ID NO 20
<211> LENGTH: 930
<212> TYPE: DNA
<213> ORGANISM: Human

<400> SEQUENCE: 20
atgctgctgc ttctgctgct tctggggcca ggctccgggc ttggtgctgt cgtctctcaa       60
catccgagct gggttatctg taagagtgga acctctgtga agatcgagtg ccgttccctg      120
gactttcagg ccacaactat gttttggtat cgtcagttcc gaaacagag tctcatgctg      180 atggcaactt ccaatgaggg ctccaaggcc acatacgagc aaggcgtcga aaggacaag      240 tttctcatca accatgcaag cctgaccttg tccactctga cagtgaccag tgcccatcct      300
gaagacagca gcttctacat ctgcagtgct agagtcgact ttgaccgtga cgagcagttc      360
ttcgggccag ggacacggct caccgtgcta gaggacctga aaaacgtgtt cccacccgag      420
gtcgctgtgt ttgagccatc agaagcagag atctcccaca cccaaaaggc cacactggtg      480
tgcctggcca caggcttcta ccccgaccac gtggagctga gctggtgggt gaatgggaag      540
gaggtgcaca gtggggtcag cacagacccg cagcccctca aggagcagcc cgccctcaat      600
gactccagat actgcctgag cagccgcctg agggtctcgg ccaccttctg gcagaacccc      660
cgcaaccact ccgctgtca agtccagttc tacgggctct cggagaatga cgagtggacc      720
caggataggg ccaaacctgt cacccagatc gtcagcgccg aggcctgggg tagagcagac      780
tgtggcttca cctccgagtc ttaccagcaa ggggtcctgt ctgccaccat cctctatgag      840
atcttgctag gaaggccac cttgtatgcc gtgctggtca gtgccctcgt gctgatggcc      900
atggtcaaga gaaaggattc cagaggctag                                       930
```

```
<210> SEQ ID NO 21
<211> LENGTH: 279
<212> TYPE: PRT
<213> ORGANISM: Human

<400> SEQUENCE: 21

Met Asn Met Leu Thr Ala Ser Leu Leu Arg Ala Val Ile Ala Ser Ile
1               5                   10                  15

Cys Val Val Ser Ser Met Ala Gln Lys Val Thr Gln Ala Gln Thr Glu
                20                  25                  30

Ile Ser Val Val Glu Lys Glu Asp Val Thr Leu Asp Cys Val Tyr Glu
            35                  40                  45

Thr Arg Asp Thr Thr Tyr Tyr Leu Phe Trp Tyr Lys Gln Pro Pro Ser
```

```
                 50                  55                  60
Gly Glu Leu Val Phe Leu Ile Arg Arg Asn Ser Phe Asp Glu Gln Asn
 65                  70                  75                  80

Glu Ile Ser Gly Arg Tyr Ser Trp Asn Phe Gln Lys Ser Thr Ser Ser
                     85                  90                  95

Phe Asn Phe Thr Ile Thr Ala Ser Gln Val Val Asp Ser Ala Val Tyr
                100                 105                 110

Phe Cys Ala Leu Ser Glu Ala Ser Gly Arg Asp Asp Lys Ile Ile Phe
                115                 120                 125

Gly Lys Gly Thr Arg Leu His Ile Leu Pro Asn Ile Gln Asn Pro Asp
            130                 135                 140

Pro Ala Val Tyr Gln Leu Arg Asp Ser Lys Ser Ser Asp Lys Ser Val
145                 150                 155                 160

Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Arg Ser
                180                 185                 190

Met Asp Phe Lys Ser Asn Ser Ala Val Ala Trp Ser Asn Lys Ser Asp
            195                 200                 205

Phe Ala Cys Ala Asn Ala Phe Asn Asn Ser Ile Ile Pro Glu Asp Thr
210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
                260                 265                 270

Thr Leu Arg Leu Trp Ser Ser
                275

<210> SEQ ID NO 22
<211> LENGTH: 309
<212> TYPE: PRT
<213> ORGANISM: Human

<400> SEQUENCE: 22

Met Leu Leu Leu Leu Leu Leu Gly Pro Gly Ser Gly Leu Gly Ala
 1               5                  10                  15

Val Val Ser Gln His Pro Ser Trp Val Ile Cys Lys Ser Gly Thr Ser
                 20                  25                  30

Val Lys Ile Glu Cys Arg Ser Leu Asp Phe Gln Ala Thr Thr Met Phe
             35                  40                  45

Trp Tyr Arg Gln Phe Pro Lys Gln Ser Leu Met Leu Met Ala Thr Ser
 50                  55                  60

Asn Glu Gly Ser Lys Ala Thr Tyr Glu Gln Gly Val Glu Lys Asp Lys
 65                  70                  75                  80

Phe Leu Ile Asn His Ala Ser Leu Thr Leu Ser Thr Leu Thr Val Thr
                 85                  90                  95

Ser Ala His Pro Glu Asp Ser Ser Phe Tyr Ile Cys Ser Ala Arg Val
                100                 105                 110

Asp Phe Asp Arg Asp Glu Gln Phe Gly Pro Gly Thr Arg Leu Thr
            115                 120                 125

Val Leu Glu Asp Leu Lys Asn Val Phe Pro Pro Glu Val Ala Val Phe
            130                 135                 140
```

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
                260                 265                 270

Leu Ser Ala Thr Ile Leu Tyr Glu Ile Leu Leu Gly Lys Ala Thr Leu
            275                 280                 285

Tyr Ala Val Leu Val Ser Ala Leu Val Leu Met Ala Met Val Lys Arg
290                 295                 300

Lys Asp Ser Arg Gly
305

<210> SEQ ID NO 23
<211> LENGTH: 822
<212> TYPE: DNA
<213> ORGANISM: Human

<400> SEQUENCE: 23
atggaaactc tcctgggagt gtctttggtg attctatggc ttcaactggc tagggtgaac    60
agtcaacagg gagaagagga tcctcaggcc ttgagcatcc aggagggtga aaatgccacc   120
atgaactgca gttacaaaac tagtataaac aatttacagt ggtatagaca aaattcaggt   180
agaggccttg tccacctaat tttaatacgt tcaaatgaaa agagagaaca cagtggaaga   240
ttaagagtca cgcttgacac ttccaagaaa agcagttcct tgttgatcac ggcttcccgg   300
gcagcagaca ctgcttctta cttctgtgct acggacgcag agtataacaa tgccagactc   360
atgtttggag atggaactca gctggtggtg aagcccaata tccagaaccc tgaccctgcc   420
gtgtaccagt tgagagactc taaatccagt gacaagtctg tctgcctatt caccgatttt   480
gattctcaaa caaatgtgtc acaaagtaag gattctgatg tgtatatcac agacaaaact   540
gtgctagaca tgaggtctat ggacttcaag agcaacagtg ctgtggcctg agcaacaaa    600 tctgactttg catgtgcaaa cgccttcaac aacagcatta ttccagaaga cacccttcttc  660 cccagcccag aaagttcctg tgatgtcaag ctggtcgaga aaagctttga acagatacg   720 aacctaaact tcaaaaacct gtcagtgatt gggttccgaa tcctcctcct gaaagtggcc   780
gggtttaatc tgctcatgac gctgcggctg tggtccagct ga                     822

<210> SEQ ID NO 24
<211> LENGTH: 939
<212> TYPE: DNA
<213> ORGANISM: Human

<400> SEQUENCE: 24
atgggcacca gcctcctctg ctggatggcc ctgtgtctcc tgggggcaga tcacgcagat    60

```
actggagtct cccaggaccc cagacacaag atcacaaaga ggggacagaa tgtaactttc      120
aggtgtgatc caatttctga acacaaccgc ctttattggt accgacagac cctggggcag      180
ggcccagagt ttctgactta cttccagaat gaagctcaac tagaaaaatc aaggctgctc      240
agtgatcggt tctctgcaga gaggcctaag ggatctttct ccaccttgga gatccagcgc      300
acagagcagg gggactcggc catgtatctc tgtgccagca gcatggtagc tggggccaac      360
gtcctgactt tcggggccgg cagcaggctg accgtgctgg aggacctgaa aacgtgttc       420 ccacccgagg tcgctgtgtt tgagccatca gaagcagaga tctcccacac ccaaaaggcc      480
acactggtgt gcctggccac aggcttctac cccgaccacg tggagctgag ctggtgggtg      540
aatgggaagg aggtgcacag tggggtcagc acagacccgc agccctcaa ggagcagccc       600 gccctcaatg actccagata ctgcctgagc agccgcctga ggtctcggc caccttctgg       660 cagaacccc gcaaccactt ccgctgtcaa gtccagttct acgggctctc ggagaatgac        720
gagtggaccc aggatagggc caaacctgtc acccagatcg tcagcgccga ggcctggggt      780
agagcagact gtggcttcac ctccgagtct taccagcaag gggtcctgtc tgccaccatc      840
ctctatgaga tcttgctagg gaaggccacc ttgtatgccg tgctggtcag tgccctcgtg      900
ctgatggcca tggtcaagag aaaggattcc agaggctag                             939

<210> SEQ ID NO 25
<211> LENGTH: 273
<212> TYPE: PRT
<213> ORGANISM: Human

<400> SEQUENCE: 25

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Asp
            100                 105                 110

Ala Glu Tyr Asn Asn Ala Arg Leu Met Phe Gly Asp Gly Thr Gln Leu
        115                 120                 125

Val Val Lys Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220
```

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
        260                 265                 270

Ser

<210> SEQ ID NO 26
<211> LENGTH: 312
<212> TYPE: PRT
<213> ORGANISM: Human

<400> SEQUENCE: 26

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Met Val Ala Gly Ala Asn Val Leu Thr Phe Gly Ala Gly Ser
        115                 120                 125

Arg Leu Thr Val Leu Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 27
<211> LENGTH: 819
<212> TYPE: DNA
<213> ORGANISM: Human

<400> SEQUENCE: 27

| | | | | | |
|---|---|---|---|---|---|
| atgatgaaat | ccttgagagt | tttactagtg | atcctgtggc | ttcagttgag ctgggtttgg | 60 |
| agccaacaga | aggaggtgga | gcagaattct | ggaccccctca | gtgttccaga gggagccatt | 120 |
| gcctctctca | actgcactta | cagtgaccga | ggttcccagt | ccttcttctg gtacagacaa | 180 |
| tattctggga | aaagccctga | gttgataatg | ttcatatact | ccaatggtga caaagaagat | 240 |
| ggaaggttta | cagcacagct | caataaagcc | agccagtatg | tttctctgct catcagagac | 300 |
| tcccagccca | gtgattcagc | cacctacctc | tgtgccgtgg | gtgctacaaa caagctcatc | 360 |
| tttggaactg | gcactctgct | tgctgtccag | ccaaatatcc | agaaccctga ccctgccgtg | 420 |
| taccagctga | gagactctaa | atccagtgac | aagtctgtct | gcctattcac cgattttgat | 480 |
| tctcaaacaa | atgtgtcaca | agtaaggat | tctgatgtgt | atatcacaga caaaactgtg | 540 |
| ctagacatga | ggtctatgga | cttcaagagc | aacagtgctg | tggcctggag caacaaatct | 600 |
| gactttgcat | gtgcaaacgc | cttcaacaac | agcattattc | cagaagacac cttcttcccc | 660 |
| agcccagaaa | gttcctgtga | tgtcaagctg | gtcgagaaaa | gctttgaaac agatacgaac | 720 |
| ctaaactttc | aaaacctgtc | agtgattggg | ttccgaatcc | tcctcctgaa agtggccggg | 780 |
| tttaatctgc | tcatgacgct | gcggctgtgg | tccagctga | | 819 |

<210> SEQ ID NO 28
<211> LENGTH: 930
<212> TYPE: DNA
<213> ORGANISM: Human

<400> SEQUENCE: 28

| | | | | | |
|---|---|---|---|---|---|
| atggttttcca | ggcttctcag | tttagtgtcc | ctttgtctcc | tgggagcaaa gcacatagaa | 60 |
| gctggagtta | ctcagttccc | cagccacagc | gtaatagaga | agggccagac tgtgactctg | 120 |
| agatgtgacc | caatttctgg | acatgataat | ctttattggt | atcgacgtgt tatgggaaaa | 180 |
| gaaataaaat | ttctgttaca | ttttgtgaaa | gagtctaaac | aggatgagtc cggtatgccc | 240 |
| aacaatcgat | tcttagctga | aaggactgga | gggacgtatt | ctactctgaa ggtgcagcct | 300 |
| gcagaactgg | aggattctgg | agtttatttc | tgtgccagca | gccaagcgta cggcactgaa | 360 |
| gctttcttgg | acaaggcac | cagactcaca | gttgtagagg | acctgaacaa ggtgttccca | 420 |
| cccgaggtcg | ctgtgtttga | gccatcagaa | gcagagatct | cccacaccca aaaggccaca | 480 |
| ctggtgtgcc | tggccacagg | cttcttccct | gaccacgtgg | agctgagctg gtgggtgaat | 540 |
| gggaaggagg | tgcacagtgg | ggtcagcacg | gacccgcagc | cctcaaggga gcagcccgcc | 600 |
| ctcaatgact | ccagatactg | cctgagcagc | cgcctgaggg | tctcggccac cttctggcag | 660 |
| aaccccgca | accacttccg | ctgtcaagtc | cagttctacg | gctctcgga gaatgacgag | 720 |
| tggacccagg | ataggccaa | acccgtcacc | cagatcgtca | gcgccgaggc ctggggtaga | 780 |
| gcagactgtg | gctttacctc | ggtgtcctac | cagcaagggg | tcctgtctgc caccatcctc | 840 |
| tatgagatcc | tgctagggaa | ggccacctg | tatgctgtgc | tggtcagcgc ccttgtgttg | 900 |
| atggccatgg | tcaagagaaa | ggatttctga | | | 930 |

<210> SEQ ID NO 29

<211> LENGTH: 272
<212> TYPE: PRT
<213> ORGANISM: Human

<400> SEQUENCE: 29

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Gly Ala Thr Asn Lys Leu Ile Phe Gly Thr Gly Thr Leu Leu Ala
        115                 120                 125

Val Gln Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 30
<211> LENGTH: 309
<212> TYPE: PRT
<213> ORGANISM: Human

<400> SEQUENCE: 30

Met Val Ser Arg Leu Leu Ser Leu Val Ser Leu Cys Leu Leu Gly Ala
1               5                   10                  15

Lys His Ile Glu Ala Gly Val Thr Gln Phe Pro Ser His Ser Val Ile
            20                  25                  30

Glu Lys Gly Gln Thr Val Thr Leu Arg Cys Asp Pro Ile Ser Gly His
        35                  40                  45

Asp Asn Leu Tyr Trp Tyr Arg Arg Val Met Gly Lys Glu Ile Lys Phe
    50                  55                  60

Leu Leu His Phe Val Lys Glu Ser Lys Gln Asp Glu Ser Gly Met Pro
65                  70                  75                  80

Asn Asn Arg Phe Leu Ala Glu Arg Thr Gly Gly Thr Tyr Ser Thr Leu
            85                  90                  95

Lys Val Gln Pro Ala Glu Leu Glu Asp Ser Gly Val Tyr Phe Cys Ala
            100                 105                 110

Ser Ser Gln Ala Tyr Gly Thr Glu Ala Phe Phe Gly Gln Gly Thr Arg
            115                 120                 125

Leu Thr Val Val Glu Asp Leu Asn Lys Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
            165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Phe
305

<210> SEQ ID NO 31
<211> LENGTH: 843
<212> TYPE: DNA
<213> ORGANISM: Human

<400> SEQUENCE: 31
atggccatgc tcctgggggc atcagtgctg attctgtggc ttcagccaga ctgggtaaac    60
agtcaacaga gaatgatga ccagcaagtt aagcaaaatt caccatccct gagcgtccag    120
gaaggaagaa tttctattct gaactgtgac tatactaaca gcatgtttga ttatttccta    180
tggtacaaaa ataccctgc tgaaggtcct acattcctga tatctataag ttccattaag    240
gataaaaatg aagatggaag attcactgtc ttcttaaaca aaagtgccaa gcacctctct    300
ctgcacattg tgccctccca gcctggagac tctgcagtgt acttctgtgc agcaagcccc    360
tctggcaaca caggcaaact aatctttggg caagggacaa ctttacaagt aaaaccagat    420
atccagaagc tgaccctgc cgtgtaccag ctgagagact ctaaatccag tgacaagtct    480
gtctgcctat tcaccgattt tgattctcaa acaaatgtgt cacaaagtaa ggattctgat    540
gtgtatatca cagacaaaac tgtgctagac atgaggtcta tggacttcaa gagcaacagt    600
gctgtggcct ggagcaacaa atctgacttt gcatgtgcaa acgccttcaa caacagcatt    660
attccagaag acaccttctt ccccagccca gaaagttcct gtgatgtcaa gctggtcgag    720
aaaagctttg aaacagatac gaacctaaac tttcaaaacc tgtcagtgat tgggttccga    780

```
atcctcctcc tgaaagtggc cgggtttaat ctgctcatga cgctgcggct gtggtccagc    840
tga                                                                  843

<210> SEQ ID NO 32
<211> LENGTH: 933
<212> TYPE: DNA
<213> ORGANISM: Human

<400> SEQUENCE: 32
atgggctcca ggctgctctg ttgggtgctg ctttgtctcc tgggagcagg cccagtaaag     60
gctggagtca ctcaaactcc aagatatctg atcaaaacga gaggacagca agtgacactg    120
agctgctccc ctatctctgg cataggagt gtatcctggt accaacagac cccaggacag     180
ggccttcagt tcctctttga atacttcagt gagacacaga gaaacaaagg aaacttccct    240
ggtcgattct cagggcgcca gttctctaac tctcgctctg agatgaatgt gagcaccttg    300
gagctggggg actcggccct ttatctttgc gccagcagcc cagacagggc catgaacact    360
gaagctttct ttggacaagg caccagactc acagttgtag aggacctgaa caaggtgttc    420
ccacccgagg tcgctgtgtt tgagccatca gaagcagaga tctcccacac ccaaaaggcc    480
acactggtgt gcctggccac aggcttcttc cctgaccacg tggagctgag ctggtgggtg    540
aatgggaagg aggtgcacag tggggtcagc acggacccgc agcccctcaa ggagcagccc    600
gccctcaatg actccagata ctgcctgagc agccgcctga gggtctcggc caccttctgg    660
cagaaccccc gcaaccactt ccgctgtcaa gtccagttct acgggctctc ggagaatgac    720
gagtggaccc aggatagggc caaacccgtc acccagatcg tcagcgccga ggcctggggt    780
agagcagact gtggctttac ctcggtgtcc taccagcaag ggtcctgtc tgccaccatc    840 ctctatgaga tcctgctagg gaaggccacc ctgtatgctg tgctggtcag cgcccttgtg    900
ttgatggcca tggtcaagag aaaggatttc tga                                 933

<210> SEQ ID NO 33
<211> LENGTH: 280
<212> TYPE: PRT
<213> ORGANISM: Human

<400> SEQUENCE: 33

Met Ala Met Leu Leu Gly Ala Ser Val Leu Ile Leu Trp Leu Gln Pro
  1               5                  10                  15

Asp Trp Val Asn Ser Gln Gln Lys Asn Asp Asp Gln Gln Val Lys Gln
                 20                  25                  30

Asn Ser Pro Ser Leu Ser Val Gln Glu Gly Arg Ile Ser Ile Leu Asn
             35                  40                  45

Cys Asp Tyr Thr Asn Ser Met Phe Asp Tyr Phe Leu Trp Tyr Lys Lys
         50                  55                  60

Tyr Pro Ala Glu Gly Pro Thr Phe Leu Ile Ser Ile Ser Ser Ile Lys
 65                  70                  75                  80

Asp Lys Asn Glu Asp Gly Arg Phe Thr Val Phe Leu Asn Lys Ser Ala
                 85                  90                  95

Lys His Leu Ser Leu His Ile Val Pro Ser Gln Pro Gly Asp Ser Ala
            100                 105                 110

Val Tyr Phe Cys Ala Ala Ser Pro Ser Gly Asn Thr Gly Lys Leu Ile
            115                 120                 125

Phe Gly Gln Gly Thr Thr Leu Gln Val Lys Pro Asp Ile Gln Lys Pro
        130                 135                 140
```

```
Asp Pro Ala Val Tyr Gln Leu Arg Asp Ser Lys Ser Asp Lys Ser
145                 150                 155                 160

Val Cys Leu Phe Thr Asp Phe Asp Ser Gln Thr Asn Val Ser Gln Ser
            165                 170                 175

Lys Asp Ser Asp Val Tyr Ile Thr Asp Lys Thr Val Leu Asp Met Arg
            180                 185                 190

Ser Met Asp Phe Lys Ser Asn Ser Ala Val Ala Trp Ser Asn Lys Ser
            195                 200                 205

Asp Phe Ala Cys Ala Asn Ala Phe Asn Asn Ser Ile Ile Pro Glu Asp
            210                 215                 220

Thr Phe Phe Pro Ser Pro Glu Ser Ser Cys Asp Val Lys Leu Val Glu
225                 230                 235                 240

Lys Ser Phe Glu Thr Asp Thr Asn Leu Asn Phe Gln Asn Leu Ser Val
                245                 250                 255

Ile Gly Phe Arg Ile Leu Leu Leu Lys Val Ala Gly Phe Asn Leu Leu
                260                 265                 270

Met Thr Leu Arg Leu Trp Ser Ser
                275                 280

<210> SEQ ID NO 34
<211> LENGTH: 310
<212> TYPE: PRT
<213> ORGANISM: Human

<400> SEQUENCE: 34

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
                20                  25                  30

Thr Arg Gly Gln Gln Val Thr Leu Ser Cys Ser Pro Ile Ser Gly His
                35                  40                  45

Arg Ser Val Ser Trp Tyr Gln Gln Thr Pro Gly Gln Gly Leu Gln Phe
50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
                100                 105                 110

Ser Pro Asp Arg Ala Met Asn Thr Glu Ala Phe Phe Gly Gln Gly Thr
            115                 120                 125

Arg Leu Thr Val Val Glu Asp Leu Asn Lys Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
```

```
                    225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305             310

<210> SEQ ID NO 35
<211> LENGTH: 825
<212> TYPE: DNA
<213> ORGANISM: Human

<400> SEQUENCE: 35
atggcctctg cacccatctc gatgcttgcg atgctcttca cattgagtgg gctgagagct        60
cagtcagtgg ctcagccgga agatcaggtc aacgttgctg aagggaatcc tctgactgtg       120
aaatgcacct attcagtctc tggaaaccct tatctttttt ggtatgttca ataccccaac       180
cgaggcctcc agttccttct gaaatacatc acagggata acctggttaa aggcagctat        240
ggctttgaag ctgaatttaa caagagccaa acctccttcc acctgaagaa accatctgcc       300
cttgtgagcg actccgcttt gtacttctgt gctgtgagag acaggagag agatgacaag        360 atcatctttg gaaagggac acgacttcat attctcccca atatccagaa gcctgaccct        420
gccgtgtacc agctgagaga ctctaaatcc agtgacaagt ctgtctgcct attcaccgat       480
tttgattctc aaacaaatgt gtcacaaagt aaggattctg atgtgtatat cacagacaaa       540
actgtgctag acatgaggtc tatggacttc aagagcaaca gtgctgtggc ctggagcaac       600
aaatctgact ttgcatgtgc aaacgccttc aacaacagca ttattccaga agacaccttc       660
ttccccagcc cagaaagttc ctgtgatgtc aagctggtcg agaaaagctt tgaaacagat       720
acgaacctaa actttcaaaa cctgtcagtg attgggttcc gaatcctcct cctgaaagtg       780
gccgggttta atctgctcat gacgctgcgg ctgtggtcca gctga                       825

<210> SEQ ID NO 36
<211> LENGTH: 936
<212> TYPE: DNA
<213> ORGANISM: Human

<400> SEQUENCE: 36
atggatacct ggctcgtatg ctgggcaatt tttagtctct tgaaagcagg actcacagaa        60
cctgaagtca cccagactcc cagccatcag gtcacacaga tgggacagga agtgatcttg       120
cgctgtgtcc ccatctctaa tcacttatac ttctattggt acagacaaat cttggggcag       180
aaagtcgagt ttctggtttc cttttataat aatgaaatct cagagaagtc tgaaatattc       240
gatgatcaat tctcagttga aaggcctgat ggatcaaatt tcactctgaa gatccggtcc       300
acaaagctgg aggactcagc catgtacttc tgtgccagca gcggagat acagatacg         360 cagtattttg gcccaggcac ccggctgaca gtgctcgagg acctgaaaaa cgtgttccca       420
cccgaggtcg ctgtgtttga gccatcagaa gcagagatcc ccacacccca aaaggccaca       480
ctggtgtgcc tggccacagg cttctacccc gaccacgtgg agctgagctg gtgggtgaat       540
```

```
gggaaggagg tgcacagtgg ggtcagcaca gacccgcagc ccctcaagga gcagcccgcc       600
ctcaatgact ccagatactg cctgagcagc cgcctgaggg tctcggccac cttctggcag       660 aaccccgca accacttccg ctgtcaagtc cagttctacg ggctctcgga gaatgacgag        720
tggacccagg atagggccaa acctgtcacc cagatcgtca cgccgaggc ctggggtaga        780 gcagactgtg gcttcacctc cgagtcttac cagcaagggg tcctgtctgc caccatcctc      840
tatgagatct tgctagggaa ggccaccttg tatgccgtgc tggtcagtgc cctcgtgctg      900
atggccatgg tcaagagaaa ggattccaga ggctag                                936
```

<210> SEQ ID NO 37
<211> LENGTH: 274
<212> TYPE: PRT
<213> ORGANISM: Human

<400> SEQUENCE: 37

```
Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Arg Glu Arg Asp Lys Ile Ile Phe Gly Lys Gly Thr Arg
        115                 120                 125

Leu His Ile Leu Pro Asn Ile Gln Lys Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 38
<211> LENGTH: 311
<212> TYPE: PRT

<213> ORGANISM: Human

<400> SEQUENCE: 38

Met Asp Thr Trp Leu Val Cys Trp Ala Ile Phe Ser Leu Leu Lys Ala
1               5                   10                  15
Gly Leu Thr Glu Pro Glu Val Thr Gln Thr Pro Ser His Gln Val Thr
            20                  25                  30
Gln Met Gly Gln Glu Val Ile Leu Arg Cys Val Pro Ile Ser Asn His
        35                  40                  45
Leu Tyr Phe Tyr Trp Tyr Arg Gln Ile Leu Gly Gln Lys Val Glu Phe
    50                  55                  60
Leu Val Ser Phe Tyr Asn Asn Glu Ile Ser Glu Lys Ser Glu Ile Phe
65                  70                  75                  80
Asp Asp Gln Phe Ser Val Glu Arg Pro Asp Gly Ser Asn Phe Thr Leu
                85                  90                  95
Lys Ile Arg Ser Thr Lys Leu Glu Asp Ser Ala Met Tyr Phe Cys Ala
            100                 105                 110
Ser Arg Ala Glu Ile Thr Asp Thr Gln Tyr Phe Gly Pro Gly Thr Arg
        115                 120                 125
Leu Thr Val Leu Glu Asp Leu Lys Asn Val Phe Pro Pro Glu Val Ala
    130                 135                 140
Val Phe Glu Pro Ser Glu Ala Glu Ile Ser His Thr Gln Lys Ala Thr
145                 150                 155                 160
Leu Val Cys Leu Ala Thr Gly Phe Tyr Pro Asp His Val Glu Leu Ser
                165                 170                 175
Trp Trp Val Asn Gly Lys Glu Val His Ser Gly Val Ser Thr Asp Pro
            180                 185                 190
Gln Pro Leu Lys Glu Gln Pro Ala Leu Asn Asp Ser Arg Tyr Cys Leu
        195                 200                 205
Ser Ser Arg Leu Arg Val Ser Ala Thr Phe Trp Gln Asn Pro Arg Asn
    210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
            260                 265                 270
Gly Val Leu Ser Ala Thr Ile Leu Tyr Glu Ile Leu Leu Gly Lys Ala
        275                 280                 285
Thr Leu Tyr Ala Val Leu Val Ser Ala Leu Val Leu Met Ala Met Val
    290                 295                 300
Lys Arg Lys Asp Ser Arg Gly
305                 310

<210> SEQ ID NO 39
<211> LENGTH: 843
<212> TYPE: DNA
<213> ORGANISM: Human

<400> SEQUENCE: 39
atggccatgc tcctgggggc atcagtgctg attctgtggc ttcagccaga ctgggtaaac      60
agtcaacaga gaatgatga ccagcaagtt aagcaaaatt caccatccct gagcgtccag     120
gaaggaagaa tttctattct gaactgtgac tatactaaca gcatgtttga ttatttccta     180
tggtacaaaa ataccctgc tgaaggtcct acattcctga tatctataag ttccattaag     240

```
gataaaaatg aagatggaag attcactgtc ttcttaaaca aaagtgccaa gcacctctct    300
ctgcacattg tgccctccca gcctggagac tctgcagtgt acttctgtgc agcaagcgcg    360
ataggaggtg ctgacggact cacctttggc aaagggactc atctaatcat ccagccctat    420
atccagaacc ctgaccctgc cgtgtaccag ctgagagact ctaaatccag tgacaagtct    480
gtctgcctat tcaccgattt tgattctcaa acaaatgtgt cacaaagtaa ggattctgat    540
gtgtatatca cagacaaaac tgtgctagac atgaggtcta tggacttcaa gagcaacagt    600
gctgtggcct ggagcaacaa atctgacttt gcatgtgcaa acgccttcaa caacagcatt    660
attccagaag acaccttctt ccccagccca gaaagttcct gtgatgtcaa gctggtcgag    720
aaaagctttg aaacagatac gaacctaaac tttcaaaacc tgtcagtgat tgggttccga    780
atcctcctcc tgaaagtggc cgggtttaat ctgctcatga cgctgcggct gtggtccagc    840
tga                                                                  843

<210> SEQ ID NO 40
<211> LENGTH: 939
<212> TYPE: DNA
<213> ORGANISM: Human

<400> SEQUENCE: 40
atgagcctcg ggctcctgtg ctgtgggggcc ttttctctcc tgtgggcagg tccagtgaat    60
gctggtgtca ctcagacccc aaaattccgg gtcctgaaga caggacagag catgacactg    120
ctgtgtgccc aggatatgaa ccatgaatac atgtactggt atcgacaaga cccaggcatg    180
gggctgaggc tgattcatta ctcagttggt gagggtacaa ctgccaaagg agaggtccct    240
gatggctaca atgtctccag attaaaaaaa cagaatttcc tgctgggggtt ggagtcggct    300 gctccctccc aaacatctgt gtacttctgt gccagcagta ttcggggaaa aaggtacaat    360
gagcagttct tcgggccagg gacacggctc accgtgctag aggacctgaa aaacgtgttc    420
ccacccgagg tcgctgtgtt tgagccatca gaagcagaga tctcccacac ccaaaaggcc    480
acactggtgt gcctggccac aggcttctac cccgaccacg tggagctgag ctggtgggtg    540
aatgggaagg aggtgcacag tggggtcagc acagacccgc agcccctcaa ggagcagccc    600
gccctcaatg actccagata ctgcctgagc agccgcctga ggtctcggc caccttctgg    660 cagaaccccc gcaaccactt ccgctgtcaa gtccagttct acgggctctc ggagaatgac    720
gagtggaccc aggataggg caaacctgtc acccagatcg tcagcgccga ggcctggggt    780
agagcagact gtggcttcac ctccgagtct taccagcaag ggtcctgtc tgccaccatc    840 ctctatgaga tcttgctagg gaaggccacc ttgtatgccg tgctggtcag tgccctcgtg    900
ctgatggcca tggtcaagag aaaggattcc agaggctag                           939

<210> SEQ ID NO 41
<211> LENGTH: 280
<212> TYPE: PRT
<213> ORGANISM: Human

<400> SEQUENCE: 41

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45
```

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
        100                 105                 110

Val Tyr Phe Cys Ala Ala Ser Ala Ile Gly Gly Ala Asp Gly Leu Thr
            115                 120                 125

Phe Gly Lys Gly Thr His Leu Ile Ile Gln Pro Tyr Ile Gln Asn Pro
    130                 135                 140

Asp Pro Ala Val Tyr Gln Leu Arg Asp Ser Lys Ser Ser Asp Lys Ser
145                 150                 155                 160

Val Cys Leu Phe Thr Asp Phe Asp Ser Gln Thr Asn Val Ser Gln Ser
                165                 170                 175

Lys Asp Ser Asp Val Tyr Ile Thr Asp Lys Thr Val Leu Asp Met Arg
            180                 185                 190

Ser Met Asp Phe Lys Ser Asn Ser Ala Val Ala Trp Ser Asn Lys Ser
    195                 200                 205

Asp Phe Ala Cys Ala Asn Ala Phe Asn Asn Ser Ile Ile Pro Glu Asp
210                 215                 220

Thr Phe Phe Pro Ser Pro Glu Ser Ser Cys Asp Val Lys Leu Val Glu
225                 230                 235                 240

Lys Ser Phe Glu Thr Asp Thr Asn Leu Asn Phe Gln Asn Leu Ser Val
                245                 250                 255

Ile Gly Phe Arg Ile Leu Leu Leu Lys Val Ala Gly Phe Asn Leu Leu
            260                 265                 270

Met Thr Leu Arg Leu Trp Ser Ser
    275                 280

<210> SEQ ID NO 42
<211> LENGTH: 312
<212> TYPE: PRT
<213> ORGANISM: Human

<400> SEQUENCE: 42

Met Ser Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Ser Ile Arg Gly Lys Arg Tyr Asn Glu Gln Phe Phe Gly Pro Gly Thr
        115                 120                 125

Arg Leu Thr Val Leu Glu Asp Leu Lys Asn Val Phe Pro Pro Glu Val

```
                130               135                140
Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
            165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
        210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
290                 295                 300

Val Lys Arg Lys Asp Ser Arg Gly
305                 310

<210> SEQ ID NO 43
<211> LENGTH: 822
<212> TYPE: DNA
<213> ORGANISM: Human

<400> SEQUENCE: 43
atggaaactc tcctgggagt gtctttggtg attctatggc ttcaactggc tagggtgaac     60
agtcaacagg gagaagagga tcctcaggcc ttgagcatcc aggagggtga aaatgccacc    120
atgaactgca gttacaaaac tagtataaac aatttacagt ggtatagaca aaattcaggt    180
agaggccttg tccacctaat tttaatacgt tcaaatgaaa gagagaaaca cagtggaaga    240
ttaagagtca cgcttgacac ttccaagaaa agcagttcct tgttgatcac ggcttcccgg    300
gcagcagaca ctgcttctta cttctgtgct acggacgccg tcgtgggtgc tgacggactc    360
acctttggca aagggactca tctaatcatc cagcctata ccagaaccc tgaccctgcc     420 gtgtaccagc tgagagactc taaatccagt gacaagtctg tctgcctatt caccgatttt    480
gattctcaaa caaatgtgtc acaaagtaag gattctgatg tgtatatcac agacaaaact    540
gtgctagaca tgaggtctat ggacttcaag agcaacagtg ctgtggcctg agcaacaaa     600 tctgactttg catgtgcaaa cgccttcaac aacagcatta ttccagaaga caccttcttc    660
cccagcccag aaagttcctg tgatgtcaag ctggtcgaga aagctttgaa acagatacg     720 aacctaaact ttcaaaacct gtcagtgatt gggttccgaa tcctcctcct gaaagtggcc    780
gggtttaatc tgctcatgac gctgcggctg tggtccagct ga                       822

<210> SEQ ID NO 44
<211> LENGTH: 936
<212> TYPE: DNA
<213> ORGANISM: Human

<400> SEQUENCE: 44
```

```
atgctgctgc ttctgctgct tctggggcca ggctccgggc ttggtgctgt cgtctctcaa    60
catccgagct gggttatctg taagagtgga acctctgtga agatcgagtg ccgttccctg   120
gactttcagg ccacaactat gttttggtat cgtcagttcc cgaaacagag tctcatgctg   180
atggcaactt ccaatgaggg ctccaaggcc acatacgagc aaggcgtcga aaggacaag    240
tttctcatca accatgcaag cctgaccttg tccactctga cagtgaccag tgcccatcct   300
gaagacagca gcttctacat ctgcagtgct agagaccggg acataggacc cttagatacg   360
cagtattttg gcccaggcac ccggctgaca gtgctcgagg acctgaaaaa cgtgttccca   420
cccgaggtcg ctgtgtttga gccatcagaa gcagagatct cccacaccca aaaggccaca   480
ctggtgtgcc tggccacagg cttctacccc gaccacgtgg agctgagctg gtgggtgaat   540
gggaaggagg tgcacagtgg ggtcagcaca gacccgcagc ccctcaagga gcagcccgcc   600
ctcaatgact ccagatactg cctgagcagc cgcctgaggg tctcggccac cttctggcag   660
aaccccccgca accacttccg ctgtcaagtc cagttctacg gctctcgga gaatgacgag    720
tggacccagg atagggccaa acctgtcacc cagatcgtca gcgccgaggc ctggggtaga   780
gcagactgtg gcttcacctc cgagtcttac cagcaagggg tcctgtctgc caccatcctc   840
tatgagatct gctagggaa ggccaccttg tatgccgtgc tggtcagtgc cctcgtgctg    900
atggccatgg tcaagagaaa ggattccaga ggctag                            936
```

<210> SEQ ID NO 45
<211> LENGTH: 273
<212> TYPE: PRT
<213> ORGANISM: Human

<400> SEQUENCE: 45

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
            85                  90                  95

Thr Ala Ser Arg Ala Ala Asp Thr Ala Ser Tyr Phe Cys Ala Thr Asp
            100                 105                 110

Ala Val Val Gly Ala Asp Gly Leu Thr Phe Gly Lys Gly Thr His Leu
            115                 120                 125

Ile Ile Gln Pro Tyr Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

```
Phe Asn Asn Ser Ile Ile Pro Glu Asp Thr Phe Phe Pro Ser Pro Glu
210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
                260                 265                 270

Ser

<210> SEQ ID NO 46
<211> LENGTH: 311
<212> TYPE: PRT
<213> ORGANISM: Human

<400> SEQUENCE: 46

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
                20                  25                  30

Val Lys Ile Glu Cys Arg Ser Leu Asp Phe Gln Ala Thr Thr Met Phe
            35                  40                  45

Trp Tyr Arg Gln Phe Pro Lys Gln Ser Leu Met Leu Met Ala Thr Ser
50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Asp
                100                 105                 110

Arg Asp Ile Gly Pro Leu Asp Thr Gln Tyr Phe Gly Pro Gly Thr Arg
            115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300
```

Lys Arg Lys Asp Ser Arg Gly
305                 310

<210> SEQ ID NO 47
<211> LENGTH: 798
<212> TYPE: DNA
<213> ORGANISM: Human

<400> SEQUENCE: 47

| | | | | | |
|---|---|---|---|---|---|
| atgaagttgg | tgacaagcat | tactgtactc | ctatctttgg | gtattatggg | tgatgctaag | 60 |
| accacacagc | caaattcaat | ggagagtaac | gaagaagagc | ctgttcactt | gccttgtaac | 120 |
| cactccacaa | tcagtggaac | tgattacata | cattggtatc | gacagcttcc | ctcccagggt | 180 |
| ccagagtacg | tgattcatgg | tcttacaagc | aatgtgaaca | acagaatggc | ctctctggca | 240 |
| atcgctgaag | acagaaagtc | cagtaccttg | atcctgcacc | gtgctacctt | gagagatgct | 300 |
| gctgtgtact | actgcatccc | taataacaat | gacatgcgct | ttggagcagg | gaccagactg | 360 |
| acagtaaaac | caaatatcca | gaaccctgac | cctgccgtgt | accagctgag | agactctaaa | 420 |
| tccagtgaca | agtctgtctg | cctattcacc | gattttgatt | ctcaaacaaa | tgtgtcacaa | 480 |
| agtaaggatt | ctgatgtgta | tatcacagac | aaaactgtgc | tagacatgag | gtctatggac | 540 |
| ttcaagagca | acagtgctgt | ggcctggagc | aacaaatctg | actttgcatg | tgcaaacgcc | 600 |
| ttcaacaaca | gcattattcc | agaagacacc | ttcttcccca | gcccagaaag | ttcctgtgat | 660 |
| gtcaagctgg | tcgagaaaag | ctttgaaaca | gatacgaacc | taaactttca | aaacctgtca | 720 |
| gtgattgggt | tccgaatcct | cctcctgaaa | gtggccgggt | taatctgct | catgacgctg | 780 |
| cggctgtggt | ccagctga | | | | | 798 |

<210> SEQ ID NO 48
<211> LENGTH: 933
<212> TYPE: DNA
<213> ORGANISM: Human

<400> SEQUENCE: 48

| | | | | | |
|---|---|---|---|---|---|
| atgggctcca | ggctgctctg | ttgggtgctg | cttttgtctcc | tgggagcagg | cccagtaaag | 60 |
| gctggagtca | ctcaaactcc | aagatatctg | atcaaaacga | gaggacagca | agtgacactg | 120 |
| agctgctccc | ctatctctgg | gcataggagt | gtatcctggt | accaacagac | cccaggacag | 180 |
| ggccttcagt | tcctctttga | atacttcagt | gagacacaga | gaaacaaagg | aaacttccct | 240 |
| ggtcgattct | cagggcgcca | gttctctaac | tctcgctctg | agatgaatgt | gagcaccttg | 300 |
| gagctggggg | actcggccct | ttatctttgc | gccagcagct | tccccaggga | acctaactat | 360 |
| ggctacacct | tcggttcggg | gaccaggtta | accgttgtag | aggacctgaa | caaggtgttc | 420 |
| ccacccgagg | tcgctgtgtt | tgagccatca | gaagcagaga | tctcccacac | ccaaaaggcc | 480 |
| acactggtgt | gcctggccac | aggcttcttc | cctgaccacg | tggagctgag | ctggtgggtg | 540 |
| aatgggaagg | aggtgcacag | tggggtcagc | acggacccgc | agcccctcaa | ggagcagccc | 600 |
| gccctcaatg | actccagata | ctgcctgagc | agccgcctga | gggtctcggc | caccttctgg | 660 |
| cagaaccccc | gcaaccactt | ccgctgtcaa | gtccagttct | acgggctctc | ggagaatgac | 720 |
| gagtggaccc | aggatagggc | caaacccgtc | acccagatcg | tcagcgccga | ggcctggggt | 780 |
| agagcagact | gtggctttac | ctcggtgtcc | taccagcaag | gggtcctgtc | tgccaccatc | 840 |
| ctctatgaga | tcctgctagg | gaaggccacc | ctgtatgctg | tgctggtcag | cgccttgtg | 900 |
| ttgatggcca | tggtcaagag | aaaggatttc | tga | | | 933 |

<210> SEQ ID NO 49
<211> LENGTH: 265
<212> TYPE: PRT
<213> ORGANISM: Human

<400> SEQUENCE: 49

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
        35                  40                  45

Tyr Ile His Trp Tyr Arg Gln Leu Pro Ser Gln Gly Pro Glu Tyr Val
    50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Pro Asn Asn Asn Asp Met
            100                 105                 110

Arg Phe Gly Ala Gly Thr Arg Leu Thr Val Lys Pro Asn Ile Gln Asn
        115                 120                 125

Pro Asp Pro Ala Val Tyr Gln Leu Arg Asp Ser Lys Ser Ser Asp Lys
    130                 135                 140

Ser Val Cys Leu Phe Thr Asp Phe Asp Ser Gln Thr Asn Val Ser Gln
145                 150                 155                 160

Ser Lys Asp Ser Asp Val Tyr Ile Thr Asp Lys Thr Val Leu Asp Met
                165                 170                 175

Arg Ser Met Asp Phe Lys Ser Asn Ser Ala Val Ala Trp Ser Asn Lys
            180                 185                 190

Ser Asp Phe Ala Cys Ala Asn Ala Phe Asn Asn Ser Ile Ile Pro Glu
        195                 200                 205

Asp Thr Phe Phe Pro Ser Pro Glu Ser Ser Cys Asp Val Lys Leu Val
    210                 215                 220

Glu Lys Ser Phe Glu Thr Asp Thr Asn Leu Asn Phe Gln Asn Leu Ser
225                 230                 235                 240

Val Ile Gly Phe Arg Ile Leu Leu Leu Lys Val Ala Gly Phe Asn Leu
                245                 250                 255

Leu Met Thr Leu Arg Leu Trp Ser Ser
            260                 265

<210> SEQ ID NO 50
<211> LENGTH: 310
<212> TYPE: PRT
<213> ORGANISM: Human

<400> SEQUENCE: 50

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
 65                  70                  75                  80

Gly Arg Phe Ser Gly Arg Gln Phe Ser Asn Ser Arg Ser Glu Met Asn
                 85                  90                  95

Val Ser Thr Leu Glu Leu Gly Asp Ser Ala Leu Tyr Leu Cys Ala Ser
            100                 105                 110

Ser Phe Pro Arg Glu Pro Asn Tyr Gly Tyr Thr Phe Gly Ser Gly Thr
        115                 120                 125

Arg Leu Thr Val Val Glu Asp Leu Asn Lys Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
290                 295                 300

Val Lys Arg Lys Asp Phe
305                 310

<210> SEQ ID NO 51
<211> LENGTH: 780
<212> TYPE: DNA
<213> ORGANISM: Human

<400> SEQUENCE: 51
atggcccaga cagtcactca gtctcaacca gagatgtctg tgcaggaggc agagactgtg      60
accctgagtt gcacatatga caccagtgag aataattatt atttgttctg gtacaagcag     120
cctcccagca ggcagatgat tctcgttatt cgccaagaag cttataagca acagaatgca     180
acggagaatc gtttctctgt gaacttccag aaagcagcca atccttcag tctcaagatc     240 tcagactcac agctggggga cactgcgatg tatttctgtg cttcctcgag agggagtgga     300
ggtagcaact ataaactgac atttggaaaa ggaactctct taaccgtgaa tccaaatatc     360
cagaaccctg accctgccgt gtaccagctg agagactcta atccagtga caagtctgtc     420 tgcctattca ccgattttga ttctcaaaca aatgtgtcac aaagtaagga ttctgatgtg     480
tatatcacag acaaaactgt gctagacatg aggtctatgg acttcaagag caacagtgct     540
gtggcctgga gcaacaaatc tgactttgca tgtgcaaacg ccttcaacaa cagcattatt     600
ccagaagaca ccttcttccc cagcccagaa agttcctgtg atgtcaagct ggtcgagaaa     660
agctttgaaa cagatacgaa cctaaacttt caaaacctgt cagtgattgg gttccgaatc     720

```
ctcctcctga aagtggccgg gtttaatctg ctcatgacgc tgcggctgtg gtccagctga    780
```

<210> SEQ ID NO 52
<211> LENGTH: 942
<212> TYPE: DNA
<213> ORGANISM: Human

<400> SEQUENCE: 52

```
atgggcacca ggctcctctt ctgggtggcc ttctgtctcc tgggggcaga tcacacagga     60
gctggagtct cccagtcccc cagtaacaag gtcacagaga agggaaagga tgtagagctc    120
aggtgtgatc caatttcagg tcatactgcc ctttactggt accgacagag cctggggcag    180
ggcctggagt ttttaattta cttccaaggc aacagtgcac cagacaaatc agggctgccc    240
agtgatcgct ctctgcaga gaggactggg ggatccgtct ccactctgac gatccagcgc    300
acacagcagg aggactcggc cgtgtatctc tgtgccagca gcttagtccc cgacagtgcc    360
tacgagcagt acttcgggcc gggcaccagg ctcacggtca cagaggacct gaaaaacgtg    420
ttcccacccg aggtcgctgt gtttgagcca tcagaagcag agatctccca caccaaaag    480 gccacactgg tatgcctggc cacaggcttc taccccgacc acgtggagct gagctggtgg    540
gtgaatggga aggaggtgca cagtggggtc agcacggacc cgcagcccct caaggagcag    600
cccgccctca tgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaacct gtcacccaga tcgtcagcgc cgaggcctgg    780
ggtagagcag actgtggctt cacctccgag tcttaccagc aagggggtcct gtctgccacc    840 atcctctatg agatcttgct agggaaggcc accttgtatg ccgtgctggt cagtgccctc    900
gtgctgatgg ccatggtcaa gagaaaggat tccagaggct ag                       942
```

<210> SEQ ID NO 53
<211> LENGTH: 259
<212> TYPE: PRT
<213> ORGANISM: Human

<400> SEQUENCE: 53

```
Met Ala Gln Thr Val Thr Gln Ser Gln Pro Glu Met Ser Val Gln Glu
1               5                  10                  15

Ala Glu Thr Val Thr Leu Ser Cys Thr Tyr Asp Thr Ser Glu Asn Asn
            20                  25                  30

Tyr Tyr Leu Phe Trp Tyr Lys Gln Pro Ser Arg Gln Met Ile Leu
        35                  40                  45

Val Ile Arg Gln Glu Ala Tyr Lys Gln Gln Asn Ala Thr Glu Asn Arg
    50                  55                  60

Phe Ser Val Asn Phe Gln Lys Ala Ala Lys Ser Phe Ser Leu Lys Ile
65                  70                  75                  80

Ser Asp Ser Gln Leu Gly Asp Thr Ala Met Tyr Phe Cys Ala Phe Ser
                85                  90                  95

Arg Gly Ser Gly Gly Ser Asn Tyr Lys Leu Thr Phe Gly Lys Gly Thr
            100                 105                 110

Leu Leu Thr Val Asn Pro Asn Ile Gln Asn Pro Asp Pro Ala Val Tyr
        115                 120                 125

Gln Leu Arg Asp Ser Lys Ser Ser Asp Lys Ser Val Cys Leu Phe Thr
    130                 135                 140

Asp Phe Asp Ser Gln Thr Asn Val Ser Gln Ser Lys Asp Ser Asp Val
```

```
                145                 150                 155                 160
        Tyr Ile Thr Asp Lys Thr Val Leu Asp Met Arg Ser Met Asp Phe Lys
                        165                 170                 175

Ser Asn Ser Ala Val Ala Trp Ser Asn Lys Ser Asp Phe Ala Cys Ala
                        180                 185                 190

Asn Ala Phe Asn Asn Ser Ile Ile Pro Glu Asp Thr Phe Phe Pro Ser
                        195                 200                 205

Pro Glu Ser Ser Cys Asp Val Lys Leu Val Glu Lys Ser Phe Glu Thr
                        210                 215                 220

Asp Thr Asn Leu Asn Phe Gln Asn Leu Ser Val Ile Gly Phe Arg Ile
        225                 230                 235                 240

Leu Leu Leu Lys Val Ala Gly Phe Asn Leu Leu Met Thr Leu Arg Leu
                        245                 250                 255

Trp Ser Ser

<210> SEQ ID NO 54
<211> LENGTH: 313
<212> TYPE: PRT
<213> ORGANISM: Human

<400> SEQUENCE: 54

Met Gly Thr Arg Leu Leu Phe Trp Val Ala Phe Cys Leu Leu Gly Ala
        1               5                   10                  15

Asp His Thr Gly Ala Gly Val Ser Gln Ser Pro Ser Asn Lys Val Thr
                        20                  25                  30

Glu Lys Gly Lys Asp Val Glu Leu Arg Cys Asp Pro Ile Ser Gly His
                        35                  40                  45

Thr Ala Leu Tyr Trp Tyr Arg Gln Ser Leu Gly Gln Gly Leu Glu Phe
                        50                  55                  60

Leu Ile Tyr Phe Gln Gly Asn Ser Ala Pro Asp Lys Ser Gly Leu Pro
        65                  70                  75                  80

Ser Asp Arg Phe Ser Ala Glu Arg Thr Gly Gly Ser Val Ser Thr Leu
                        85                  90                  95

Thr Ile Gln Arg Thr Gln Gln Glu Asp Ser Ala Val Tyr Leu Cys Ala
                        100                 105                 110

Ser Ser Leu Val Pro Asp Ser Ala Tyr Glu Gln Tyr Phe Gly Pro Gly
                        115                 120                 125

Thr Arg Leu Thr Val Thr Glu Asp Leu Lys Asn Val Phe Pro Pro Glu
                        130                 135                 140

Val Ala Val Phe Glu Pro Ser Glu Ala Glu Ile Ser His Thr Gln Lys
        145                 150                 155                 160

Ala Thr Leu Val Cys Leu Ala Thr Gly Phe Tyr Pro Asp His Val Glu
                        165                 170                 175

Leu Ser Trp Trp Val Asn Gly Lys Glu Val His Ser Gly Val Ser Thr
                        180                 185                 190

Asp Pro Gln Pro Leu Lys Glu Gln Pro Ala Leu Asn Asp Ser Arg Tyr
                        195                 200                 205

Cys Leu Ser Ser Arg Leu Arg Val Ser Ala Thr Phe Trp Gln Asn Pro
                        210                 215                 220

Arg Asn His Phe Arg Cys Gln Val Gln Phe Tyr Gly Leu Ser Glu Asn
        225                 230                 235                 240

Asp Glu Trp Thr Gln Asp Arg Ala Lys Pro Val Thr Gln Ile Val Ser
                        245                 250                 255

Ala Glu Ala Trp Gly Arg Ala Asp Cys Gly Phe Thr Ser Glu Ser Tyr
```

```
          260              265              270
Gln Gln Gly Val Leu Ser Ala Thr Ile Leu Tyr Glu Ile Leu Leu Gly
        275                  280                  285

Lys Ala Thr Leu Tyr Ala Val Leu Val Ser Ala Leu Val Leu Met Ala
        290                  295                  300

Met Val Lys Arg Lys Asp Ser Arg Gly
305                 310
```

<210> SEQ ID NO 55
<211> LENGTH: 828
<212> TYPE: DNA
<213> ORGANISM: Human

<400> SEQUENCE: 55

```
atgctcctgc tgctcgtccc agtgctcgag gtgattttta ccctgggagg aaccagagcc    60
cagtcggtga cccagcttgg cagccacgtc tctgtctctg agggagccct ggttctgctg   120
aggtgcaact actcatcgtc tgttccacca tatctcttct ggtatgtgca ataccccaac   180
caaggactcc agcttctcct gaagcacaca acaggggcca cctggttaa aggcatcaac    240
ggttttgagg ctgaatttaa gaagagtgaa acctccttcc acctgacgaa accctcagcc   300
catatgagcg acgcggctga gtacttctgt gctgtgagtg attctagggc tgcaggcaac   360
aagctaactt ttggaggagg aaccagggtg ctagttaaac aaatatcca gaaccctgac    420
cctgccgtgt accagctgag agactctaaa tccagtgaca gtctgtctg cctattcacc    480
gattttgatt ctcaaacaaa tgtgtcacaa agtaaggatt ctgatgtgta tatcacagac   540
aaaactgtgc tagacatgag gtctatggac ttcaagagca cagtgctgt ggcctggagc    600
aacaaatctg actttgcatg tgcaaacgcc ttcaacaaca gcattattcc agaagacacc   660
ttcttcccca gcccagaaag ttcctgtgat gtcaagctgg tcgagaaaag ctttgaaaca   720
gatacgaacc taaactttca aaacctgtca gtgattgggt tccgaatcct cctcctgaaa   780
gtggccgggt ttaatctgct catgacgctg cggctgtggt ccagctga              828
```

<210> SEQ ID NO 56
<211> LENGTH: 936
<212> TYPE: DNA
<213> ORGANISM: Human

<400> SEQUENCE: 56

```
atgggaatca ggctcctctg tcgtgtggcc ttttgtttcc tggctgtagg cctcgtagat    60
gtgaaagtaa cccagagctc gagatatcta gtcaaaagga cgggagagaa agttttctg   120
gaatgtgtcc aggatatgga ccatgaaaat atgttctggt atcgacaaga cccaggtctg   180
gggctacggc tgatctattt ctcatatgat gttaaaatga agaaaaagg agatattcct   240
gaggggtaca gtgtctctag agagaagaag gagcgcttct ccctgattct ggagtccgcc   300
agcaccaacc agacatctat gtacctctgt gccagcagat tccccgggac agcctataat   360
tcacccctcc actttgggaa tgggaccagg ctcactgtga cagaggacct gaacaaggtg   420
ttcccacccg aggtcgctgt gtttgagcca tcagaagcag atctcccca cacccaaaag   480
gccacactgg tgtgcctggc cacaggcttc ttccctgacc acgtggagct gagctggtgg   540
gtgaatggga aggaggtgca cagtggggtc agcacggacc cgcagcccct caaggagcag   600
cccgccctca tgactccag atactgcctg agcagccgcc tgagggtctc ggccaccttc   660
tggcagaacc cccgcaacca cttccgctgt caagtccagt tctacgggct ctcggagaat   720
```

```
gacgagtgga cccaggatag ggccaaaccc gtcacccaga tcgtcagcgc cgaggcctgg    780
ggtagagcag actgtggctt tacctcggtg tcctaccagc aagggtcct gtctgccacc    840 atcctctatg agatcctgct agggaaggcc accctgtatg ctgtgctggt cagcgccctt    900
gtgttgatgg ccatggtcaa gagaaaggat ttctga                             936
```

<210> SEQ ID NO 57
<211> LENGTH: 275
<212> TYPE: PRT
<213> ORGANISM: Human

<400> SEQUENCE: 57

```
Met Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser
                20                  25                  30

Ser Glu Gly Ala Leu Val Leu Leu Arg Cys Asn Tyr Ser Ser Val
            35                  40                  45

Pro Pro Tyr Leu Phe Trp Tyr Val Gln Tyr Pro Asn Gln Gly Leu Gln
    50                  55                  60

Leu Leu Leu Lys His Thr Thr Gly Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
                100                 105                 110

Ser Asp Ser Arg Ala Ala Gly Asn Lys Leu Thr Phe Gly Gly Gly Thr
            115                 120                 125

Arg Val Leu Val Lys Pro Asn Ile Gln Asn Pro Asp Pro Ala Val Tyr
130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275
```

<210> SEQ ID NO 58
<211> LENGTH: 311
<212> TYPE: PRT
<213> ORGANISM: Human

<400> SEQUENCE: 58

Met Gly Ile Arg Leu Leu Cys Arg Val Ala Phe Cys Phe Leu Ala Val

```
            1               5                  10                 15
            Gly Leu Val Asp Val Lys Val Thr Gln Ser Ser Arg Tyr Leu Val Lys
                        20                  25                  30

Arg Thr Gly Glu Lys Val Phe Leu Glu Cys Val Gln Asp Met Asp His
                        35                  40                  45

Glu Asn Met Phe Trp Tyr Arg Gln Asp Pro Gly Leu Gly Leu Arg Leu
                        50                  55                  60

Ile Tyr Phe Ser Tyr Asp Val Lys Met Lys Glu Lys Gly Asp Ile Pro
            65                  70                  75                  80

Glu Gly Tyr Ser Val Ser Arg Glu Lys Lys Glu Arg Phe Ser Leu Ile
                                85                  90                  95

Leu Glu Ser Ala Ser Thr Asn Gln Thr Ser Met Tyr Leu Cys Ala Ser
                        100                 105                 110

Arg Phe Pro Gly Thr Ala Tyr Asn Ser Pro Leu His Phe Gly Asn Gly
                        115                 120                 125

Thr Arg Leu Thr Val Thr Glu Asp Leu Asn Lys Val Phe Pro Pro Glu
                        130                 135                 140

Val Ala Val Phe Glu Pro Ser Glu Ala Glu Ile Ser His Thr Gln Lys
            145                 150                 155                 160

Ala Thr Leu Val Cys Leu Ala Thr Gly Phe Phe Pro Asp His Val Glu
                        165                 170                 175

Leu Ser Trp Trp Val Asn Gly Lys Glu Val His Ser Gly Val Ser Thr
                        180                 185                 190

Asp Pro Gln Pro Leu Lys Glu Gln Pro Ala Leu Asn Asp Ser Arg Tyr
                        195                 200                 205

Cys Leu Ser Ser Arg Leu Arg Val Ser Ala Thr Phe Trp Gln Asn Pro
            210                 215                 220

Arg Asn His Phe Arg Cys Gln Val Gln Phe Tyr Gly Leu Ser Glu Asn
            225                 230                 235                 240

Asp Glu Trp Thr Gln Asp Arg Ala Lys Pro Val Thr Gln Ile Val Ser
                        245                 250                 255

Ala Glu Ala Trp Gly Arg Ala Asp Cys Gly Phe Thr Ser Val Ser Tyr
                        260                 265                 270

Gln Gln Gly Val Leu Ser Ala Thr Ile Leu Tyr Glu Ile Leu Leu Gly
                        275                 280                 285

Lys Ala Thr Leu Tyr Ala Val Leu Val Ser Ala Leu Val Leu Met Ala
                        290                 295                 300

Met Val Lys Arg Lys Asp Phe
            305                 310

<210> SEQ ID NO 59
<211> LENGTH: 4
<212> TYPE: PRT
<213> ORGANISM: Artificial Sequence
<220> FEATURE:
<223> OTHER INFORMATION: Furin protease recognition site

<400> SEQUENCE: 59

Arg Ala Lys Arg
1

<210> SEQ ID NO 60
<211> LENGTH: 4
<212> TYPE: PRT
<213> ORGANISM: Artificial Sequence
<220> FEATURE:
<223> OTHER INFORMATION: linker sequence
```

<400> SEQUENCE: 60

Ser Gly Ser Gly
1

<210> SEQ ID NO 61
<211> LENGTH: 14
<212> TYPE: PRT
<213> ORGANISM: Artificial Sequence
<220> FEATURE:
<223> OTHER INFORMATION: DP4 peptide sequence

<400> SEQUENCE: 61

Ser Leu Leu Met Trp Ile Thr Gln Cys Phe Leu Pro Val Phe
1               5                   10

<210> SEQ ID NO 62
<211> LENGTH: 6
<212> TYPE: PRT
<213> ORGANISM: Artificial Sequence
<220> FEATURE:
<223> OTHER INFORMATION: modified DP4

<400> SEQUENCE: 62

Leu Leu Met Trp Ile Thr
1               5

<210> SEQ ID NO 63
<211> LENGTH: 14
<212> TYPE: PRT
<213> ORGANISM: Artificial Sequence
<220> FEATURE:
<223> OTHER INFORMATION: NY-ESO-1 sequence 157-170

<400> SEQUENCE: 63

Ser Leu Leu Met Trp Ile Thr Gln Cys Phe Leu Pro Val Phe
1               5                   10

<210> SEQ ID NO 64
<211> LENGTH: 12
<212> TYPE: PRT
<213> ORGANISM: Artificial Sequence
<220> FEATURE:
<223> OTHER INFORMATION: NY-ESO-1 sequence sequence 95-106

<400> SEQUENCE: 64

Pro Phe Ala Thr Pro Met Glu Ala Glu Leu Ala Arg
1               5                   10

<210> SEQ ID NO 65
<211> LENGTH: 834
<212> TYPE: DNA
<213> ORGANISM: Human

<400> SEQUENCE: 65
atgatgaaat ccttgagagt tttactagtg atcctgtggc ttcagttgag ctgggtttgg      60
agccaacaga aggaggtgga gcagaattct ggacccctca gtgttccaga gggagccatt     120
gcctctctca actgcactta cagtgaccga ggttcccagt ccttcttctg gtacagacaa     180
tattctggga aaagccctga gttgataatg tccatatact ccaatggtga caaagaagat     240
ggaaggttta cagcacagct caataaagcc agccagtatg tttctctgct catcagagac     300
tcccagccca gtgattcagc cacctacctc tgtgccgtgg ggggacttac ctctagcaac     360
acaggcaaac taatctttgg gcaagggaca actttacaag taaaaccaga tatccagaac     420

```
cctgaccctg ccgtgtacca gctgagagac tctaaatcca gtgacaagtc tgtctgccta      480
ttcaccgatt ttgattctca aacaaatgtg tcacaaagta aggattctga tgtgtatatc      540
acagacaaaa ctgtgctaga catgaggtct atggacttca agagcaacag tgctgtggcc      600
tggagcaaca aatctgactt tgcatgtgca aacgccttca acaacagcat tattccagaa      660
gacaccttct tccccagccc agaaagttcc tgtgatgtca agctggtcga gaaaagcttt      720
gaaacagata cgaacctaaa cttcaaaac ctgtcagtga ttgggttccg aatcctcctc      780
ctgaaagtgg ccgggtttaa tctgctcatg acgctgcggc tgtggtccag ctga            834

<210> SEQ ID NO 66
<211> LENGTH: 924
<212> TYPE: DNA
<213> ORGANISM: Human

<400> SEQUENCE: 66
atgggaatca ggctcctctg tcgtgtggcc ttttgtttcc tggctgtagg cctcgtagat        60
gtgaaagtaa cccagagctc gagatatcta gtcaaaagga cgggagagaa agttttctg      120 gaatgtgtcc aggatatgga ccatgaaaat atgttctggt atcgacaaga cccaggtctg      180
gggctacggc tgatctattt ctcatatgat gttaaaatga aagaaaaagg agatattcct      240
gaggggtaca gtgtctctag agagaagaag gagcgcttct ccctgattct ggagtccgcc      300
agcaccaacc agacatctat gtacctctgt gccagcagta accagatcta tggctacacc      360
ttcggttcgg ggaccaggtt aaccgttgta gaggacctga acaaggtgtt cccacccgag      420
gtcgctgtgt ttgagccatc agaagcagag atctcccaca cccaaaaggc cacactggtg      480
tgcctggcca caggcttctt ccctgaccac gtggagctga gctggtgggt gaatgggaag      540
gaggtgcaca gtggggtcag cacggacccg cagccctca aggagcagcc cgccctcaat      600
gactccagat actgcctgag cagccgcctg agggtctcgg ccaccttctg gcagaacccc      660
cgcaaccact tccgctgtca agtccagttc tacgggctct cggagaatga cgagtggacc      720
caggataggg ccaaacccgt cacccagatc gtcagcgccg aggcctgggg tagagcagac      780
tgtggcttta cctcggtgtc ctaccagcaa ggggtcctgt ctgccaccat cctctatgag      840
atcctgctag ggaaggccac cctgtatgct gtgctggtca gcgcccttgt gttgatggcc      900
atggtcaaga gaaaggattt ctga                                             924
```